(12) United States Patent
Curtiss, III et al.

(10) Patent No.: US 9,062,297 B2
(45) Date of Patent: Jun. 23, 2015

(54) YERSINIA PESTIS VACCINE

(75) Inventors: Roy Curtiss, III, Paradise Valley, AZ (US); Wei Sun, Tempe, AZ (US)

(73) Assignee: The Arizona Board of Regents for and on Behalf of Arizona State University, Tempe, AZ (US)

(*) Notice: Subject to any disclaimer, the term of this patent is extended or adjusted under 35 U.S.C. 154(b) by 0 days.

(21) Appl. No.: 13/006,072

(22) Filed: Jan. 13, 2011

(65) Prior Publication Data

US 2011/0256177 A1 Oct. 20, 2011

Related U.S. Application Data

(60) Provisional application No. 61/294,727, filed on Jan. 13, 2010.

(51) Int. Cl.
| | | |
|---|---|---|
| A61K 39/00 | (2006.01) |
| A61K 39/02 | (2006.01) |
| A61K 39/385 | (2006.01) |
| A01N 63/00 | (2006.01) |
| C12N 1/36 | (2006.01) |
| C07K 14/24 | (2006.01) |

(52) U.S. Cl.
CPC .............. *C12N 1/36* (2013.01); *A61K 39/0291* (2013.01); *A61K 2039/522* (2013.01); *C07K 14/24* (2013.01)

(58) Field of Classification Search
CPC ................... A61K 2039/52; A61K 2039/522; A61K 2039/552; A61K 39/0291; A61K 35/74; C12N 1/00; C12N 15/00; C12N 15/01; C12N 15/09; C12N 15/74
See application file for complete search history.

(56) References Cited

U.S. PATENT DOCUMENTS

| | | | |
|---|---|---|---|
| 4,190,495 | A | 2/1980 | Curtiss, III |
| 4,888,170 | A | 12/1989 | Curtiss, III |
| 4,968,619 | A | 11/1990 | Curtiss, III |
| 5,210,035 | A | 5/1993 | Stocker |
| 5,294,441 | A | 3/1994 | Curtiss, III |
| 5,387,744 | A | 2/1995 | Curtiss |
| 5,389,368 | A | 2/1995 | Gurtiss, III |
| 5,424,065 | A | 6/1995 | Curtiss, III |
| 5,468,485 | A | 11/1995 | Curtiss, III |
| 5,536,658 | A | 7/1996 | Shotts, Jr. et al. |
| 5,654,184 | A | 8/1997 | Curtiss, III |
| 5,656,488 | A | 8/1997 | Curtiss, III |
| 5,672,345 | A | 9/1997 | Curtiss, III |

(Continued)

FOREIGN PATENT DOCUMENTS

| | | |
|---|---|---|
| EP | 0315682 B1 | 12/1993 |
| EP | 0381706 B1 | 4/1995 |

(Continued)

OTHER PUBLICATIONS

Sun et al., (Applied and Environmental Microbio. Jul. 2008. vol. 74(13):4241-4245).*

(Continued)

*Primary Examiner* — Ja'Na Hines
(74) *Attorney, Agent, or Firm* — Rebecca C. Riley-Vargas; Polsinelli PC

(57) ABSTRACT

The present invention encompasses a recombinant *Yersinia pestis* bacterium and a vaccine comprising a recombinant *Yersinia pestis* bacterium.

13 Claims, 31 Drawing Sheets

(8 of 31 Drawing Sheet(s) Filed in Color)

(56) References Cited

U.S. PATENT DOCUMENTS

| | | | |
|---|---|---|---|
| 5,679,880 A | 10/1997 | Curtiss, III | |
| 5,686,079 A | 11/1997 | Curtiss, III | |
| 5,817,317 A | 10/1998 | Titball | |
| 5,827,705 A | 10/1998 | Dean | |
| 5,840,483 A | 11/1998 | Curtiss, III | |
| 5,855,879 A | 1/1999 | Curtiss, III | |
| 5,855,880 A | 1/1999 | Curtiss, III | |
| 5,961,983 A | 10/1999 | Brey et al. | |
| 6,024,961 A | 2/2000 | Curtiss, III | |
| 6,180,614 B1 | 1/2001 | Davis | |
| 6,248,329 B1 | 6/2001 | Chandrashekar et al. | |
| 6,350,454 B1 | 2/2002 | Thune | |
| 6,383,496 B1 | 5/2002 | Curtiss, III | |
| 6,399,074 B1 | 6/2002 | Roland | |
| 6,403,094 B1 | 6/2002 | Titball | |
| 6,610,529 B1 | 8/2003 | Curtiss, III | |
| 6,780,405 B1 | 8/2004 | Curtiss, III | |
| 6,872,547 B1 | 3/2005 | Curtiss, III | |
| 6,969,513 B2 | 11/2005 | Galen | |
| 7,083,794 B2 | 8/2006 | Curtiss, III | |
| 7,195,757 B2 | 3/2007 | Curtiss, III | |
| 7,205,125 B2 | 4/2007 | Castillo | |
| 7,341,860 B2 | 3/2008 | Curtiss, III | |
| 7,871,604 B1 | 1/2011 | Curtiss, III | |
| 7,968,101 B2 | 6/2011 | Kawaoka | |
| 8,133,493 B2 | 3/2012 | Curtiss, III | |
| 8,445,254 B2 | 5/2013 | Curtiss, III et al. | |
| 8,465,755 B2 | 6/2013 | Curtiss, III et al. | |
| 2003/0031683 A1 | 2/2003 | Curtiss, III | |
| 2003/0175772 A1 | 9/2003 | Wang | |
| 2004/0077556 A1 | 4/2004 | Chinery | |
| 2004/0101531 A1 | 5/2004 | Curtiss, III | |
| 2004/0120962 A1 | 6/2004 | Curtiss, III | |
| 2004/0137003 A1 | 7/2004 | Curtiss, III | |
| 2004/0203039 A1 | 10/2004 | Hensel | |
| 2005/0036987 A1 | 2/2005 | Pawelek | |
| 2005/0106175 A1 | 5/2005 | Montanes | |
| 2005/0106176 A1* | 5/2005 | Curtis et al. | 424/200.1 |
| 2005/0118193 A1 | 6/2005 | Andino-Pavlovsky et al. | |
| 2006/0140975 A1 | 6/2006 | Curtiss, III | |
| 2006/0171917 A1 | 8/2006 | Campbell | |
| 2006/0206961 A1 | 9/2006 | Cirpus | |
| 2006/0233829 A1 | 10/2006 | Curtiss, II | |
| 2006/0234346 A1 | 10/2006 | Retallack | |
| 2006/0275255 A1 | 12/2006 | Gudkov | |
| 2007/0025981 A1 | 2/2007 | Szalay | |
| 2008/0096809 A1 | 4/2008 | Shai | |
| 2008/0248066 A1 | 10/2008 | Dubensky, Jr. | |
| 2009/0175829 A1 | 7/2009 | Forbes | |
| 2010/0124558 A1 | 5/2010 | Curtiss, III | |
| 2010/0154293 A1 | 6/2010 | Hom et al. | |
| 2010/0255022 A1 | 10/2010 | Prescott et al. | |
| 2010/0285592 A1 | 11/2010 | Curtiss, III | |
| 2010/0317084 A1 | 12/2010 | Curtiss, II | |
| 2011/0033501 A1 | 2/2011 | Curtiss, III et al. | |
| 2011/0256181 A1 | 10/2011 | Curtiss, III | |
| 2011/0287052 A1 | 11/2011 | Curtiss, III et al. | |
| 2012/0087946 A1 | 4/2012 | Curtiss, III | |
| 2013/0004537 A1 | 1/2013 | Curtiss, III et al. | |
| 2013/0171190 A1 | 7/2013 | Curtiss, III et al. | |

FOREIGN PATENT DOCUMENTS

| | | | |
|---|---|---|---|
| EP | 0465560 B1 | 6/1996 | |
| EP | 0500699 B1 | 6/1998 | |
| EP | 0558631 B1 | 3/1999 | |
| EP | 0433372 B1 | 6/2002 | |
| EP | 1030690 B1 | 7/2002 | |
| EP | 0556333 B1 | 3/2003 | |
| EP | 1326960 B1 | 12/2004 | |
| EP | 0832255 B1 | 12/2005 | |
| EP | 1537214 B1 | 3/2006 | |
| EP | 1292687 B1 | 8/2006 | |
| WO | 88/09669 A1 | 12/1988 | |
| WO | 89/03427 A1 | 4/1989 | |
| WO | 90/02484 A1 | 3/1990 | |
| WO | 90/11687 A1 | 10/1990 | |
| WO | 90/11688 A1 | 10/1990 | |
| WO | 90/12086 A1 | 10/1990 | |
| WO | 91/06317 A1 | 5/1991 | |
| WO | 92/08486 A1 | 5/1992 | |
| WO | 92/09684 A1 | 6/1992 | |
| WO | 93/04202 A1 | 3/1993 | |
| WO | 94/24291 A2 | 10/1994 | |
| WO | 94/24291 A3 | 12/1994 | |
| WO | 96/40947 A1 | 12/1996 | |
| WO | 99/25387 A1 | 5/1999 | |
| WO | 01/83785 A2 | 11/2001 | |
| WO | 01/83785 A3 | 11/2001 | |
| WO | 02/30457 A2 | 4/2002 | |
| WO | 02/059292 A2 | 8/2002 | |
| WO | 02/059292 A3 | 8/2002 | |
| WO | 02/30457 A3 | 1/2003 | |
| WO | 02/030457 A3 | 7/2003 | |
| WO | 03/079792 A1 | 10/2003 | |
| WO | 03/096812 A1 | 11/2003 | |
| WO | 2004/020643 A2 | 3/2004 | |
| WO | 2004/020643 A3 | 4/2004 | |
| WO | 2005/001069 A1 | 1/2005 | |
| WO | 2008/141226 A2 | 11/2008 | |
| WO | 2009/025888 A2 | 2/2009 | |
| WO | WO 2009/025888 * | 2/2009 | C12N 1/21 |
| WO | 2009/046449 A1 | 4/2009 | |
| WO | 2009/046451 A1 | 4/2009 | |
| WO | 2010/045620 A1 | 4/2010 | |
| WO | 2010/078584 A1 | 8/2010 | |
| WO | 2010/135563 A1 | 11/2010 | |
| WO | 2011/091291 A1 | 7/2011 | |
| WO | 2011/150421 A2 | 12/2011 | |
| WO | 2012087483 A1 | 6/2012 | |

OTHER PUBLICATIONS

Quenee et al. Infect Immun. May 2008; 76(5): 2025-2036.*
CDC, Update: influenza activity—United States, Sep. 30, 2007-Apr. 5, 2008, and composition of the 2008-09 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
Collins et al., Mutations at rfc or pmi attenuate *Salmonella typhimurium* virulence for mice. Infect. Immun., 1991, pp. 1079-1085, vol. 59.
Curtiss et al., Avirulent *Salmonella typhimurium* delta cya delta crp oral vaccine strains expressing a streptococcal colonization and virulence antigen. Vaccine, 1988, pp. 155-160, vol. 6.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella typhimurium* deletion mutants lacking adenylate cyclase and cyclic AMP receptor protein are avirulent and immunogenic. Infect Immun, 1987, pp. 3035-3043, vol. 55.
Curtiss et al., Stabilization of recombinant avirulent vaccine strains in vivo. Res Microbiol, 1990, pp. 797-805, vol. 141.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.
Daigle et al., Identification of *Salmonella typhi* genes expressed within macrophages by selective capture of transcribed sequences (SCOTS). Mol Microbiol, 2001, pp. 1211-1222, vol. 41.
Darzins. Nucleotide-sequence analysis of the phosphomannose isomerase gene (PMI) of *Pseudomonas aeruginosa* and comparison with the corresponding *Escherichia-coli* gene mana. Gene, 1986, pp. 293-302, vol. 42, No. 3.
Dean, 1997. Import of plasmid DNA into the nucleus is sequence specific. Exp. Cell Res., 1997, pp. 293-302, vol. 230.

(56) References Cited

OTHER PUBLICATIONS

Doggett et al., Immune responses to *Streptococcus sobrinus* surface protein antigen A expressed by recombinant *Salmonella typhimurium*. Infect Immun, 1993, pp. 1859-1866, vol. 61.
Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.
Dusek et al., Brown, Systemic and mucosal immune responses in mice orally immunized with avirulent *Salmonella typhimurium* expressing a cloned *Porphyromonas gingivalis* hemagglutinin. Infect Immun, 1994, pp. 1652-1657, vol. 62, No. 5.
Egan et al., A regulatory cascade in the induction of rhaBAD. J Mol Biol, 1993, pp. 97-98, vol. 234.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.
Formal et al., Construction of a potential bivalent vaccine strain: introduction of *Shigella sonnei* form I antigen genes into the galE *Salmonella typhi* Ty21a typhoid vaccine strain. Infect. Immun., 1981, pp. 746-750, vol. 34.
Fraser et al., The amino acid composition of T3 bacteriophage. J Biol Chem, 1953, pp. 291-295, vol. 205, No. 1.
Galan et al., Cloning and molecular characterization of genes whose products allow *Salmonella typhimurium* to penetrate tissue culture cells. Proc Natl Acad Sci U S A, 1989, pp. 6383-6387, vol. 86.
Galen et al., Optimization of Plasmid Maintenance in the Attenuated Live Vector Vaccine Strain *Salmonella typhi* CVD 908-htrA. Infect. Immun., 1999, pp. 6424-6433, vol. 67.
Garmory et al., Antibiotic-free plasmid stabilization by operator-repressor titration for vaccine delivery by using live *Salmonella enterica* serovar Typhimurium. Infect. Immun., 2005, pp. 2005-2011, vol. 73.
Gay et al., Positive selection procedure for entrapment of insertion sequence elements in gram-negative bacteria. J Bacteriol, 1985, pp. 918-921, vol. 164, No. 2.
Gentschev et al., Delivery of the p67 sporozoite antigen of *Theileria parva* by using recombinant *Salmonella dublin*: secretion of the product enhances specific antibody responses in cattle. Infect. Immun., 1998, pp. 2060-2064, vol. 66.
Gerdil, The annual production cycle for influenza vaccine. Vaccine, 2003, pp. 1776-1779, vol. 21.
Ghany et al. Candidate live, attenuated *Salmonella enterica* serotype Typhimurium vaccines with reduced fecal shedding are immunogenic and effective oral vaccines. Infect. Immun., 2007, pp. 1835-1842, vol. 75.
Greenwood, The epidemiology of pneumococcal infection in children in the developing world. Philos. Trans. R. Soc. Lond. B. Biol. Sci., 1999, pp. 777-785, vol. 354.
Gulig et al., Plasmid-associated virulence of *Salmonella typhimurium*. Infect Immun, 1987, pp. 2891-2901, vol. 55.
Guzman et al., Tight regulation, modulation, and high-level expression by vectors containing the arabinose PBAD promoter. J Bacteriol, 1995, pp. 4121-4130, vol. 177.
Hall et al., The role of fur in the acid tolerance response of *Salmonella typhimurium* is physiologically and genetically separable from its role in iron acquisition. J Bacteriol, 1996, pp. 5683-5691, vol. 178.
Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.
Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.

Hitchcock et al., Morphological heteronucleic acid sequenceity among *Salmonella lipopolysaccharide* chemotypes in silver-stained polyacrylamide gels. J Bacteriol, 1983, pp. 269-277, vol. 154, No. 1.
Hoffmann et al., "Ambisense" approach for the generation of influenza A virus: vRNA and mRNA synthesis from one template. Virology, 2000, pp. 310-317, vol. 267.
Hohmann et al., Macrophage-inducible expression of a model antigen in *Salmonella typhimurium* enhances immunogenicity. Proc Natl Acad Sci U S A, 1995, pp. 2904-2908, vol. 92, No. 7.
Hollingshead et al., Diversity of PspA: mosaic genes and evidence for past recombination in *Streptococcus pneumoniae*. Infect. Immun., 2000, pp. 5889-5900, vol. 68.
Hopkins et al., A recombinant *Salmonella typhimurium* vaccine induces local immunity by four different routes of immunization. Infect Immun, 1995, pp. 3279-3286, vol. 63.
Jin et al., Multiple amino acid residues confer temperature sensitivity to human influenza virus vaccine strains (FluMist) derived from cold-adapted A/Ann Arbor/6/60. Virology, 2003, pp. 18-24, vol. 306.
Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.
Kang et al., Immune responses to recombinant pneumococcal PspA antigen delivered by live attenuated *Salmonella enterica* serovar typhimurium vaccine. Infect. Immun., 2002, pp. 1739-1749, vol. 70.
Kang et al., Transduction-mediated transfer of unmarked deletion and point mutations through use of counterselectable suicide vectors. J Bacteriol, 2002, pp. 307-312, vol. 184.
Katzman et al., Invertebrate connective tissue. Isolation of D-arabinose from sponge acidic polysaccharide. Biochem J, 1970, pp. 17-19, vol. 119, No. 1.
Kennedy et al., Attenuation and immunogenicity of Delta cya Delta crp derivatives of *Salmonella choleraesuis* in pigs. Infection and Immunity, 1999, pp. 4628-4636, vol. 67, No. 9.
Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.
Klumpp et al., Roles of the influenza virus polymerase and nucleoprotein in forming a functional RNP structure. EMBO J., 1997, pp. 1248-1257, vol. 16.
Kong et al, Regulated programmed lysis of recombinant *Salmonella* in host tissues to release protective antigens and confer biological containment. PNAS, 2008, pp. 9361-9366, vol. 105, No. 27.
Konjufca et al., A Recombinant Attenuated *Salmonella enterica* Serovar Typhimurium Vaccine Encoding *Eimeria acervulina* Antigen Offers Protection against *E. acervulina* Challenge. Infect. Immun., 2006, pp. 6785-6796, vol. 74.
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of *Yersinia pestis* is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella typhimurium*. Methods Enzymol, 1991, pp. 18-43, vol. 204.
Straley et al., Virulence genes regulated at the transcriptional level by Ca2+ in *Yersinia pestis* include structural genes for outer membrane proteins. Infect Immun, 1986, pp. 445-454, vol. 51.
Sun et al., The role of relA and spoT in *Yersinia pestis* KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of *Salmonella*. J Biol Chem, 2006, pp. 30112-30121, vol. 281.

(56) References Cited

OTHER PUBLICATIONS

Une et al., In vivo comparison of avirulent Vwa- and Pgm- or Pstr phenotypes of Yersiniae. Infect Immun, 1984, pp. 895-900, vol. 43.
Uzzau et al., Epitope tagging of chromosomal genes in *Salmonella.* Proc Natl Acad Sci U S A, 2001, pp. 15264-15269, vol. 98.
Viboud et al., *Yersinia* outer proteins: role in modulation of host cell signaling responses and pathogenesis. Annu Rev Microbiol, 2005, pp. 69-89, vol. 59.
Wasserman et al., Two alanine racemase genes in *Salmonella typhimurium* that differ in structure and function. J. Bacteriol., 1983, pp. 1439-1450, vol. 153.
Whitfield, Biosynthesis and assembly of capsular polysaccharides in *Escherichia coli.* Annu Rev. Biochem., 2006, pp. 39-68, vol. 75.
Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of relA null mutants can be eliminated by spoT null mutations. J Biol Chem, 1991, pp. 5980-5990, vol. 266.
Zahorchak et al., Effect of exogenous nucleotides on Ca2+ dependence and V antigen synthesis in *Yersinia pestis.* Infect Immun, 1982, pp. 953-959, vol. 38.
Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The Ralstonia eutropha H16 phasin PhaP1 is targeted to intracellular triacylglycerol inclusions in *Rhodococcus opacus* PD630 and *Mycobacterium smegmatis* mc2155, and provides an anchor to target other proteins.
Kong et al, Regulated Delayed Expression of rfaH in an Attenuated *Salmonella enterica* Serovar Typhimurium Vaccine Enhances Immunogenicity of Outer Membrane Proteins and Heterologous Antigen. Infec Immun. 2009, pp. 5572-5582, vol. 77, No. 12.
Lefman et al, Three-Dimensional Electron Microscopic Imaging of Membrane Invaginations in *Escherichia coli* Overproducing the Chemotaxis Receptor Tsr. Journal of Bacteriology, 2004, pp. 5052-5061, vol. 186, No. 15.
Morita et al., Antibacterial Activity of *Bacillus amyloliquefaciencs* Phage Endolysin without Holin Conjugation. Journal of Biosciences and Bioengineering, 2001, pp. 469-473, vol. 91, No. 5.
Navasa et al, Temperature has reciprocal effects on colanic acid and polysialic acid biosynthesis in *E. coli* K92. Appl Microbiol Biotechnol, 2009, pp. 721-729, vol. 82.
U.S. Appl. No. 12/759,842, Office Action dated Jun. 7, 2012.
U.S. Appl. No. 12/599,655, Office Action dated Jul. 2, 2012.
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli.* Nucleic acid sequence, 1988. pp. 301-315, vol. 69, No. 2.
Anderson et al., Delivery of the Pertactin/P.69 polypeptide of *Bordetella pertussis* using an attenuated *Salmonella typhimurium* vaccine strain: expression levels and immune response. Vaccine, 1996, pp. 1384-1390, vol. 14, No. 14.
Aravind et al., The HD domain defines a new superfamily of metal-dependent phosphohydrolases. Trends Biochem Sci, 1998, pp. 469-472, vol. 23.
Arricau et al., the RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.
Arulanandam et al., Intranasal vaccination with pneumococcal surface protein A and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from *Yersinia pestis* KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae.* Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, the Vwa+ virulence factor of Yersiniae: the molecular basis of the attendant nutritional requirement for Ca2+. Rev Infect Dis, 1983, pp. S748-S758, vol. 5, Suppl 4.
Brumell et al., (2004) *Salmonella* redirects phagosomal maturation. Curr Opin Microbiol, 2004, pp. 78-84, vol. 7.
Cárdenas et al., Oral immunization using live attenuated *Salmonella* spp. as carriers of foreign antigens. Clin. Microbiol. Rev., 1992, pp. 328-342, vol. 5, No. 3.
Charnetzky et al., RNA synthesis in *Yersinia pestis* during growth restriction in calcium-deficient medium. J Bacteriol, 1982, pp. 108-195, vol. 149.
Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.
Cheng et al., Simultaneous analyses of neutral carbohydrates and amino sugars in freshwaters with HPLC-PAD. J. Chromatogr. Sci., 2003, pp. 434-438, vol. 41.
Chipman et al., The ACT domain family. Curr Opin Struct Biol, 2001, pp. 694-700, vol. 11.
Chromy et al., Proteomic characterization of *Yersinia pestis* virulence. J Bacteriol, 2005, pp. 8172-8180, vol. 187.
Coombes et al., SseL is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.
Cornelis et al., The virulence plasmid of *Yersinia,* an antihost genome. Microbiol Mol Biol Rev, 1998, pp. 1315-1352, vol. 62.
Curtiss et al. Nonrecombinant and recombinant avirulent *Salmonella* vaccines for poultry. Vet Immunol Immunopathol, 1996, pp. 365-372, vol. 54.
Curtiss et al., Live oral avirulent *Salmonella* vaccines. Vet. Microbiol., 1993, pp. 397-405, vol. 37.
Curtiss et al., Recombinant *Salmonella* vectors in vaccine development. Dev Biol Stand., 1994, pp. 23-33, vol. 82.
Datsenko et al., One-step inactivation of chromosomal genes in *Escherichia coli* K-12 using PCR products. Proc Natl Acad Sci U S A, 2000, pp. 6640-6645, vol. 97.
Davison, Towards safer vectors for the field release of recombinant bacteria. Environ. Biosafety Res., 2002, pp. 9-18, vol. 1.
De Groote et al., Homocysteine antagonism of nitric oxide-related cytostasis in *Salmonella typhimurium.* Science, 1996, pp. 414-417, vol. 272.

(56) References Cited

OTHER PUBLICATIONS

Dekruyff et al., Induction of immunoglobulin synthesis by CD4+ T cell clones. Seminars in Immunology, 1993, pp. 421-430, vol. 5.
Del Beccaro et al., Bacteriology of acute otitis media: a new perspective. J Pediatr, 1992, pp. 81-84, vol. 120.
Deng et al., Genome sequence of *Yersinia pestis* KIM. J Bacteriol, 2002, pp. 4601-4611, vol. 184.
Doggett et al., Delivery of antigens by recombinant avirulent *Salmonella* strains. Adv. Exp. Med. Biol., 1992, pp. 165-173, vol. 327.
Doublet et al., The murI gene of *Escherichia coli* is an essential gene that encodes a glutamate racemase activity. J. Bacteriol., 1993, pp. 2970-2979, vol. 175.
Dubnau, DNA uptake in bacteria. Annu. Rev. Microbiol., 1999, pp. 217-244, vol. 53.
Edwards et al., Improved allelic exchange vectors and their use to analyze 987P fimbria nucleic acid sequence expression. Gene, 1998, pp. 149-157, vol. 207, No. 2.
Fooks, Development of oral vaccines for human use. Curr Opin Mol Ther, 2000, pp. 80-86, vol. 2, No. 1.
Foster et al., How *Salmonella* survive against the odds. Annu Rev Microbiol, 1995, pp. 145-174, vol. 49.
Galen et al., Can a 'flawless' live vector vaccine strain be engineered? Trends Microbiol, 2001, pp. 372-376, vol. 9, No. 8.
Garmory et al., The Use of Live Attenuated Bacteria as a Delivery System for Heterologous Antigens. Journal of Drug Targeting, 2003, pp. 471, vol. 11.
Garzon et al., recB recJ mutants of *Salmonella typhimurium* are deficient in transductional recombination, DNA repair and plasmid maintenance. Mol. Gen. Genet., 1996, pp. 570-580, vol. 250.
Gentry et al., Mutational analysis of the *Escherichia coli* spoT gene identifies distinct but overlapping regions involved in ppGpp synthesis and degradation. Mol Microbiol, 1996, pp. 1373-1384, vol. 19.
Gentschev et al., The *E. coli* alpha-hemolysin secretion system and its use in vaccine development. Trends Microbiol, 2002, pp. 39-45, vol. 10, No. 1.
Giannella et al., Gastric acidity and cholera. Ann Intern Med, 1973, p. 780, vol. 78.
Gilbert, The lac repressor and the lac operator. Ciba Found Symp, 1972, pp. 24-59, vol. 7.
Gong et al., Characterization of the *Yersinia pestis* Yfu ABC inorganic iron transport system. Infect Immun, 2001, pp. 2829-2837, vol. 69.
Gor et al., TH1-TH2: a Procrustean paradigm. Nat Immunol, 2003, p. 503-505, vol. 4.
Grillot-Courvalin et al., Functional gene transfer from intracellular bacteria to mammalian cells. Nat. Biotechnol., 1998, pp. 862-866, vol. 16.
Guerrant et al., Magnitude and Impact of Diarrheal Diseases. Arch. Med. Res., 2002, pp. 351-355, vol. 33.
Gunn, Mechanisms of bacterial resistance and response to bile. Microbes Infect, 2000, pp. 907-913, vol. 2.
Hengge-Aronis et al., Identification and molecular analysis of glgS, a novel growth-phase-regulated and rpoS-dependent gene involved in glycogen synthesis in *Escherichia coli*. Mol Microbiol, 1992, pp. 1877-1886, vol. 6.
Hess et al., Secretion of different listeriolysin cognates by recombinant attenuated *Salmonella typhimurium*: superior efficacy of haemolytic over non-haemolytic constructs after oral vaccination. Microbes Infect, 2000, pp. 1799-1806, vol. 2.
Hohmann et al., Evaluation of a phoP/phoQ-deleted, aroA-deleted live oral *Salmonella typhi* vaccine strain in human volunteers. Vaccine, 1996, pp. 19-24, vol. 14.
Hu et al., The inducible lac operator-repressor system is functional in mammalian cells. Cell, 1987, pp. 555-566, vol. 48, No. 4.
Hu et al., The inducible lac operator-repressor system is functional for control of expression of injected DNA in *Xenopus* oocytes. Gene, 1988, pp. 301-313, vol. 62, No. 2.

Huang et al., Genome-wide screen of *Salmonella* nucleic acid sequences expressed during infection in pigs, using in vivo expression technology. Appl Environ Microbiol, 2007, pp. 7522-7530, vol. 73, No. 23.
Iannelli et al., Allelic variation in the highly polymorphic locus pspC of *Streptococcus pneumoniae*. Gene, 2002, pp. 63-71, vol. 284.
In Soo Lee et al., The stationary-phase sigma factor sS (RpoS) is required for a sustained acid tolerance response in virulent *Salmonella typhimurium*. Molecular Microbiology, 1995, pp. 155-167, vol. 17.
!Soda et al., Expression of a *Porphyromonas gingivalis* hemagglutinin on the surface of a *Salmonella* vaccine vector. Vaccine, 2007, pp. 117-126, vol. 25, No. 1.
Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.
Kaufmann et al., Impact of intracellular location of and antigen display by intracellular bacteria: implications for vaccine development. Immunol. Lett., 1999, pp. 81-84, vol. 65.
Khan et al., Immunogenicity and protective efficacy of DnaJ (hsp40) of *Streptococcus pneumoniae* against lethal infection in mice. Vaccine, 2006, pp. 6225-6231, vol. 24.
Kim et al., Direct transcriptional control of the plasminogen activator gene of *Yersinia pestis* by the cyclic AMP receptor protein. J Bacteriol, 2007, pp. 8890-8900, vol. 189.
Kolodrubetz et al., Regulation of the L-arabinose transport operons in *Escherichia coli*. J Mol Biol, 1981, pp. 215-227, vol. 151, No. 2.
Kwon et al., *Salmonella*-based vaccines for infectious diseases. Expert Review of Vaccines, 2007, pp. 147-152, vol. 6.
Lange et al- Identification of a central regulator of stationary-phase gene expression in *Escherichia coli*. Mol Microbiol, 1991, pp. 49-59, vol. 5.
Lee et al., Regulation of L-arabinose transport in *Salmonella typhimurium* LT2. Mol Gen Genet, 1982, pp. 136-141, vol. 185, No. 1.
Lee et al., Surface-displayed viral antigens on *Salmonella* carrier vaccine. Nat Biotechnol, 2000, pp. 645-648, vol. 18, No. 6.
Lewis, The lac repressor. C R Biol, 2005, pp. 521-548, vol. 328, No. 6.
Lobell et al., AraC-DNA looping: orientation and distance-dependent loop breaking by the cyclic AMP receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.
Marshall et al., Use of the stationary phase inducible promoters, spy and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in *Yersinia pestis*. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.

(56) References Cited

OTHER PUBLICATIONS

Muller-Hill, Lac repressor and lac operator. Prog Biophys Mol Biol, 1975, pp. 227-252, vol. 30, No. 2-3.

Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.

Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.

Nedialkov et al., Resistance to lipopolysaccharide mediated by the *Yersinia pestis* V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 351.
Perry et al., Temperature regulation of the hemin storage (Hms+) phenotype of *Yersinia pestis* is posttranscriptional. J Bacteriol, 2004, pp. 1638-1647, vol. 186.
Petersen et al., Essential role for cyclic AMP and its receptor protein in *Yersinia enterocolitica* virulence. Infect Immun, 2004, pp. 3665-3672, vol. 70.
Ramarathinam et al., *Salmonella typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.
Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. for mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.
Kotton et al., Enteric pathogens as vaccine vectors for foreign antigen delivery. Infect. Immun., 2004, pp. 5535-5547, vol. 72.
Lee et al., Characterization of recent H5 subtype avian influenza viruses from US poultry. Avian Pathol., 2004, pp. 288-297, vol. 33.
Lee et al., Mechanism of araC autoregulation and the domains of two overlapping promoters, PC and PBAD, in the L-arabinose regulatory region of *Escherichia coli*. Proc. Natl. Acad. Sci. U S A, 1981, pp. 752-756, vol. 78.
Li et al., A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.
Lee et al., Trigger factor retards protein export in *Escherichia coli*. J Biol Chem, 2002, pp. 43527-43535, vol. 277.
Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.
Loessner et al., Differential effect of auxotrophies on the release of macromolecules by *Salmonella enterica* vaccine strains. FEMS Microbiol. Lett., 2006, pp. 81-88, vol. 265.
Loewen et al., Genetic mapping of katF, a locus that with katE affects the synthesis of a second catalase species in *Escherichia coli*. J Bacteriol, 1984, pp. 668-675, vol. 160.
Luytjes et al., Amplification, expression, and packaging of foreign gene by influenza virus. Cell, 1989, pp. 1107-1113, vol. 59.
Malley et al., CD4+ T cells mediate antibody-independent acquired immunity to pneumococcal colonization. PNAS, 2005, pp. 4848-4853, vol. 102.
Massin et al., Cloning of the chicken RNA polymerase I promoter and use for reverse genetics of influenza A viruses in avian cells. J. Virol., 2005, pp. 13811-13816, vol. 79.
Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.
McClelland et al., Complete genome sequence of *Salmonella enterica* serovar Typhimurium LT2. Nature, 2001, pp. 852-856, vol. 413, No. 6858.
McDaniel et al., Monoclonal antibodies against protease sensitive pneumococcal antigens can protect mice from fatal infection with *Streptococcus pneumoniae*. J. Exp. Med., 1984, pp. 368-397, vol. 160.
McDaniel et al., Use of insertional inactivation to facilitate studies of biological properties of pneumococcal surface protein A (PspA). J. Exp. Med., 1987, pp. 381-394, vol. 165.
Mesika et al., A regulated, NF κB-assisted import of plasmid DNA into mammalian cell nuclei. Mol. Ther., 2001, pp. 653-657, vol. 3.
Miller et al., A novel suicide vector and its use in construction of insertion mutations: osmoregulation of outer membrane proteins and virulence determinants in Vibrio cholerae requires toxR. J Bacteriol, 1988, pp. 2575-2583, vol. 170.
Miller et al., Bacteriophage T4 genome. Microbiol Mol Biol Rev, 2003, pp. 86-156, vol. 67, No. 1.
Molinari et al., The annual impact of seasonal influenza in the US: measuring disease burden and costs. Vaccine, 2007, pp. 5086-5096, vol. 25.
Mulvey et al., Regulation of transcription of katE and katF in *Escherichia coli*. J Bacteriol, 1990, pp. 6713-6720, vol. 172.
Murti et al., Localization of RNA polymerases on influenza viral ribonucleoproteins by immunogold labeling. Virology, 1988, pp. 562-566, vol. 164.
Nardelli-Haefliger et al., Human papillomavirus type 16 virus-like particles expressed in attenuated *Salmonella typhimurium* elicit mucosal and systemic neutralizing antibodies in mice. Infect Immun, 1997, pp. 3328-3336, vol. 65.
Nayak et al., A live recombinant avirulent oral *Salmonella* vaccine expressing pneumococcal surface protein A induces protective responses against *Streptococcus pneumoniae*. Infect Immun., 1998, pp. 3744-3751, vol. 66.
Neumann et al., An improved reverse genetics system for influenza A virus generation and its implications for vaccine production. Proc. Natl. Acad. Sci. USA, 2005, pp. 16825-16829, vol. 102.
Neumann et al., Generation of influenza A viruses entirely from cloned cDNAs. Proc. Natl. Acad. Sci. USA, 1999, pp. 9345-9350, vol. 96.
Neumann et al., RNA polymerase I-mediated expression of influenza viral RNA molecules. Virology, 1994, pp. 477-479, vol. 202.
Nickerson et al., Role of sigma factor RpoS in initial stages of *Salmonella typhimurium* infection. Infect Immun, 1997, pp. 1814-1823, vol. 65.

(56) References Cited

OTHER PUBLICATIONS

Noda et al., Architecture of ribonucleoprotein complexes in influenza A virus particles. Nature, 2006, pp. 490-492, vol. 439.
Oehler et al., The three operators of the lac operon cooperate in repression. EMBO J, 1990, pp. 973-979, vol. 9, No. 4.
Ogunniyi et al., Contributions of Pneumolysin, Pneumococcal Surface Protein A (PspA), and PspC to Pathogenicity of *Streptococcus pneumoniae* D39 in a Mouse Model. Infect. Immun., 2007, pp. 1843-1851, vol. 75.
Osterholm, Preparing for the next pandemic. N. Engl. J. Med., 2005, pp. 1839-1842, vol. 352.
Ozaki et al., Generation of high-yielding influenza A viruses in African green monkey kidney (Vero) cells by reverse genetics. J. Virol., 2004, pp. 1851-1857, vol. 78.
Park et al., Engineered viral vaccine constructs with dual specificity: avian influenza and Newcastle disease. Proc. Natl. Acad. Sci. USA, 2006, pp. 8203-8208, vol. 103.
Pascual et al., Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.
Pashine et al., Th1 dominance in the immune response to live *Salmonella typhimurium* requires bacterial invasiveness but not persistence. Int. Immunol., 1999, pp. 481-489, vol. 11.
Peterson et al., RpoS proteolysis is regulated by a mechanism that does not require the SprE (RssB) response regulator phosphorylation site. J Bacteriol, 2004, pp. 7403-7410, vol. 186.
Pizarro-Cerda et al., The bacterial signal molecule, ppGpp, regulates *Salmonella* virulence nucleic acid sequence expression. Mol Microbiol, 2004, pp. 1827-1844, vol. 52, No. 6.
Prouty et al., *Salmonella enterica* serovar Typhimurium invasion is repressed in the presence of bile. Infect Immun, 2000, pp. 6763-6769, vol. 68.
Quinlivan et al., Attenuation of equine influenza viruses through truncations of the NS1 protein. J. Virol., 2005, pp. 8431-8439, vol. 79.
Rand, Crystal violet can be used to visualize DNA bands during gel electrophoresis and to improve cloning efficiency. Tech. Tips Online, 1996 http://www.science-direct.com/science/journal/13662120.
Roberts et al., Oral vaccination against tetanus: comparison of the immunogenicities of *Salmonella* strains expressing fragment C from the nirB and htrA promoters. Infect. Immun., 1998, pp. 3080-3087, vol. 66.
Romeo et al., Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.
Sadler et al., A perfectly symmetric lac operator binds the lac repressor very tightly. Proc Natl Acad Sci U S A, 1983, pp. 6785-6789, vol. 80, No. 22.
Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-260, vol. 183.
Schodel et al., Hybrid hepatitis B virus core-pre-S proteins synthesized in avirulent *Salmonella typhimurium* and *Salmonella typhi* for oral vaccination. Infect Immun, 1994, pp. 1669-1676, vol. 62, No. 5.
Schodel, Recombinant avirulent *Salmonellae* as oral vaccine carriers. Infection, 1992, pp. 1-8, vol. 20.
Schuchat et al., Bacterial meningitis in the United States in 1995. Active Surveillance Team. N Engl J Med, 1997, pp. 970-976, vol. 337.
Schulman et al., Independent variation in nature of hemagglutinin and neuraminidase antigens of influenza virus: distinctiveness of hemagglutinin antigen of Hong Kong-68 virus. Proc. Natl. Acad. Sci. USA, 1969, pp. 326-333, vol. 63.
Siegele et al., Gene Expression from plasmids containing the araBAD promoter at subsaturating inducer concentrations represents mixed populations. Proc Natl Acad Sci U S A, 1997, pp. 8168-8172, vol. 94, No. 15.
Simonsen et al., The impact of influenza epidemics on hospitalizations. J. Infect. Dis., 2000, pp. 831-837, vol. 181.
PCT/US2008/063303 (WO 2008/141226)—International Search Report and Written Opinion of the International Searching Authority, Nov. 26, 2008.
PCT/US2008/063293 (WO 2009/025888)—International Search Report and Written Opinion of the International Searching Authority, Feb. 12, 2009.
PCT/US2008/078991 (WO 2009/046449)—International Search Report and Written Opinion of the International Searching Authority, Dec. 15, 2008.
PCT/US2008/078993 (WO 2009/046451)—International Search Report and Written Opinion of the International Searching Authority, Dec. 15, 2008.
PCT/US2010/035630 (WO 2010/135563)—International Search Report and Written Opinion of the International Searching Authority, Sep. 29, 2010.
PCT/US2009/061100 (WO 2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO 2011/091291)—International Search Report and Written Opinion of the International Searching Authority, Apr. 11, 2011.
PCT/US2011/038588 (WO 2011/150421)—International Search Report and Written Opinion of the International Searching Authority, Nov. 22, 2011.
PCT/US98/24295—International Preliminary Examination Report, Dec. 26, 2000.
PCT/US2001/013915—International Preliminary Examination Report, Aug. 16, 2002.
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995 by A. Ormerod.
European Patent Application No. 90905859.6 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 7, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.

(56) References Cited

OTHER PUBLICATIONS

European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office action dated Jan. 17, 2007.
European Patent Application No. 03721711.4 (EP1499191), Office action dated Mar. 23, 2009.
European Patent Application No. 03721711.4 (EP1499191), Office action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
Song et al., Organization and regulation of the D-xylose operons in *Escherichia coli* K-12: XylR acts as a transcriptional activator. J Bacteriol, 1997, pp. 7025-7032, vol. 179.
Spellberg et al., Type 1/type 2 immunity in infectious diseases. Clin. Infect. Dis., 2001, pp. 76-102, vol. 32.
Schnaitman et al., Genetics of Lipopolysaccharide Biosynthesis in Enteric Bacteria. Microbiological Reviews, 1993, pp. 655-682, vol. 57, No. 3.
Srinivasan et al., Oral immunization with attenuated *Salmonella* expressing human sperm antigen induces antibodies in serum and the reproductive tract. Biol Reprod, 1995, pp. 462-471, vol. 53.
Steel et al., Live attenuated influenza viruses containing NS1 truncations as vaccine candidates against H5N1 highly pathogenic avian influenza. J. Virol., 2009, pp. 1742-1753, vol. 83.
Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. Infect.Immun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UD-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Servoar Typhimurium. Journal of Bacteriology, 2009, pp. 1278-1292, vol. 191, No. 4.
PCT/US2011/061896—International Search Report and Written Opinion of the International Searching Authority, Apr. 5, 2012.
Byl et al, Sequence of the Genomore of *Salmonella* Bacteriophage P22. Journal of Bacteriology, 2000, pp. 6472-6484, vol. 182, 22.
Houng et al., Expression of Vi antigen in *Escherichia coli* K-12: characterization of ViaB from *Citrobacter freundii* and identity of ViaA with RcsB. J.Bacterio, 1992, pp. 5910-5915, vol. 174, No. 18.
Hori et al, Constructionof selt-disruptive *Bacillus megaterium* in response to substrate exhaustion for polyhydroxybutryrate production. Appl Microbiol Biotechnol, 2002, pp. 211-216, vol. 59.
Hurme et al, A Proteinaceous Gene Regulator Thermameter in *Salmonella*. Cell, 1997, pp. 55-64, vol. 90.
Kong et al., *Salmonelle* synthesizing 1-Monophosphorylated Lipopolysaccharide Exhibits Low Endotoxic while Retaining Its Immunogenicity. J Immunol, 2011, pp. 412-423, vol. 187.
Pickard et al., Characterization of defined ompR mutants of *Salmonella typhi*: ompR is involved in the regulation of Vi polysaccharide expression. Infect Immun, 1994, pp. 3984-3993, vol. 62, No. 9.
Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.
Takaya et al., The ATP-Dependent Lon Protease of *Salmonella enterica* Serovar Typhimurium Regulates Invasion and Expression of Genes Carried on *Salmonella* Pathogenicity Island 1. Journal of Bacteriology, 2002, pp. 224-232, vol. 184, No. 1.
Waltman et al., Biochemical Characteristics of *Edwardsiella ictaluri*. Applied and Enviornmental Microbiology, 1986, pp. 101-104, vol. 51, No. 1.
U.S. Appl. No. 12/681,711, Office Action dated Jan. 31, 2012.
Verjan et al, Genetic Loci of Major Antigenic Protein Genes of *Edwardsiella tarda*. Applied and Environmental Microbiology, 2005, pp. 5654-5658, vol. 71, No. 9.
Nieto et al., Complex Structure of the nuclear translocation signal of influenza virus polymerase PA subunit. Journal of General Nirology, 1994, pp. 29-36, vol. 75.
U.S. Appl. No. 12/681,721, Office Action dated May 24, 2012.
Ellis, New Technologies for Making Vaccines., in Vaccines, 1988, Chapter 29 pp. 568-575, W.B. Saunders Company, Philadelphia.
Houghten et al, Relative Importance of Position and Individual Amino Acid Residues in Peptide Antigen-Antibody Interactions: Implications in the Mechanism of Antigenic Drift and Antigenic Shift, in Vaccines, 1986, pp. 21-25, Cold Spring Harbor Laboratory.
Greenspan et al, Defining Epitopes: It's Not as Easy as it Seems. Nature Biotechnology, 1999, pp. 936-937, vol. 17.
Stevens et al, Immunization with the C-Domain of alpha-Toxin Prevents Lethal Infection, Localizes Tissue Injury, and Promotes Host Response to Challenge with *Clostridium* perfringens. JID, 2004, pp. 767-773, vol. 190.
U.S. Appl. No. 08/761,769, Office Action dated Sep. 25, 2001.
U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.

(56) References Cited

OTHER PUBLICATIONS

U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
UU.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office action dated Feb. 22, 2012.
U.S. Appl. No. 12/615,872, Office Action dated Mar. 14, 2012.
U.S. Appl. No. 12/759,842, Office Action dated Oct. 4, 2011.
U.S. Appl. No. 12/789,869, Office Action dated Mar. 22, 2011.
U.S. Appl. No. 12/789,869, Office Action dated Dec. 7, 2011.
Bang et al, OmpR regulates the stationary-phase acid tolerance response of *Salmonella enterica* serovar Typhimurium. J Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., a low pH-inducible, PhoPQ-dependent acid tolerance response protects *Salmonella typhimurium* against inorganic acid stress. J Bacteriol, 1998, pp. 2409-2417, vol. 180.
Bertani, Studies on lysonucleic acid sequencesis. I. The mode of phage liberation by lysogenic *Escherichia coli*. J Bacteriol, 1951, pp. 293-300, vol. 62, No. 3.
Black et al., Aspartic •-semialdehydedehydrogenase and aspartic •-semialdehydel Biol. Chem., 1955, pp. 39-50, vol. 213.
Briles et al., Immunization of humans with recombinant pneumococcal surface protein A (rPspA) elicits antibodies that passively protect mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun., 1999, pp. 6533-6542, vol. 67.

Brosius et al., Spacing of the -10 and -35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.
Buchanan et al., IL-12 Enhances Antibody Responses to T-Independent Polysaccharide Vaccines in the Absence of T and NK Cells. J Immunol, 1998, pp. 5525-5533, vol. 161.
Buchmeier, et al., DNA repair is more important than catalase for *Salmonella* virulence in mice. J. Clin. Invest., 1995, pp. 1047-1053, vol. 95.
Bumann, Regulated antigen expression in live recombinant *Salmonella enterica* serovar Typhimurium strongly affects colonization capabilities and specific CD4(+)-T-cell responses. Infect Immun, 2001. pp. 7493-7500, vol. 69, No. 12.
U.S. Appl. No. 12/599,655, Office Action dated Mar. 12, 2013.
U.S. Appl. No. 13/088,141, Office Action dated Apr. 24, 2014.
U.S. Appl. No. 12/681,711, Office Action dated Nov. 28, 2012.
U.S. Appl. No. 13/574,718, Office Action dated Sep. 6, 2013.
U.S. Appl. No. 13/574,718, Office Action dated Apr. 28, 2014.
U.S. Appl. No. 13/700,591, Office Action dated Apr. 2, 2014.
U.S. Appl. No. 13/898,241, Office Action dated Apr. 17, 2014.
Bittner et al., RpoS and RpoN are involved in the growth-dependent regulation of rfaH transcription and O antigen expression in *Salmonella enterica* serovar Typhi, Microbial Pathogenisis. vol. 36, 2004 (p. 19).
Liu et al., Nickel-inducible lysis system in *Synechocystis* sp. PCC 6803. PNAS, vol. 106, 2009, pp. 21550-21554.
Liu et al., $CO_2$—limitation-inducible Green Recovery of fatty acids from cyanobacterial biomass. PNAS, vol. 108, 2011 pp. 6905-6908.
Moreno et al., *Salmonella* as Live Trojan Horse for Vaccine Development and Cancer Gene Therapy. Current Gene Therapy, 2010, 10, pp. 56-76.
U.S. Appl. No. 13/302,575, Office Action dated Jun. 18, 2013.
Folkesson et al., Components of the peptidoglycan-recycling pathway modulate invasion and intracellular survival of *Salmonella enterica* serovar Typhimurium. Cellular Microbiology, 2005, vol. 7(1) pp. 147-155.
Whitworth et al., Expression of the *Rickettsia prowazekii* pld or tlyC Gene in *Salmonella enterica*Serovar Typhimurium Mediates Phagosomal Escape, Infection and Immunity, 2005, vol. 73(10), pp. 6668-6673.
U.S. Appl. No. 12/615,872, Office Action dated Oct. 23, 2012.
U.S. Appl. No. 12/789,869, Office Action dated Jun. 3, 2014.
U.S. Appl. No. 13/006,072, Office Action dated Dec. 11, 2012.
U.S. Appl. No. 13/088,141, Office Action dated Dec. 6, 2012.
U.S. Appl. No. 13/302,575, Office Action dated Sep. 25, 2012.
Kong. Improving DNA Vaccine Vector for Efficient Vaccine Delivery using Live Attenuated Bacterial Carrier. American Society for Microbiology, T-010, 2008, vol. 108, p. 668.
Ribeiro et al., The role of Polyadenylation Signal Secondary Structures on the Resistance of Plasmid Vectors to Nucleases. J. Gene Med., vol. 6, 2004 (pp. 565-573).
Rytkonen, PNAS, Rytkonen et al., Ssel, a *Salmonella deubiquitinase* required for macrophase killing and virulence. PNAS, 2007, vol. 104 (pp. 3502-3507).
Wang et al., Hemagglutinin (HA) Proteins from H1 and H3 Serotypes of Influenza A Viruses Require Different Antigen Designs for the Induction of Optimal Protective Antibody Responses as Studied by Codon—Optimized HA DNA Vaccines. Journal of Virology, 2006. vol. 80 (pp. 11628-11637).

* cited by examiner

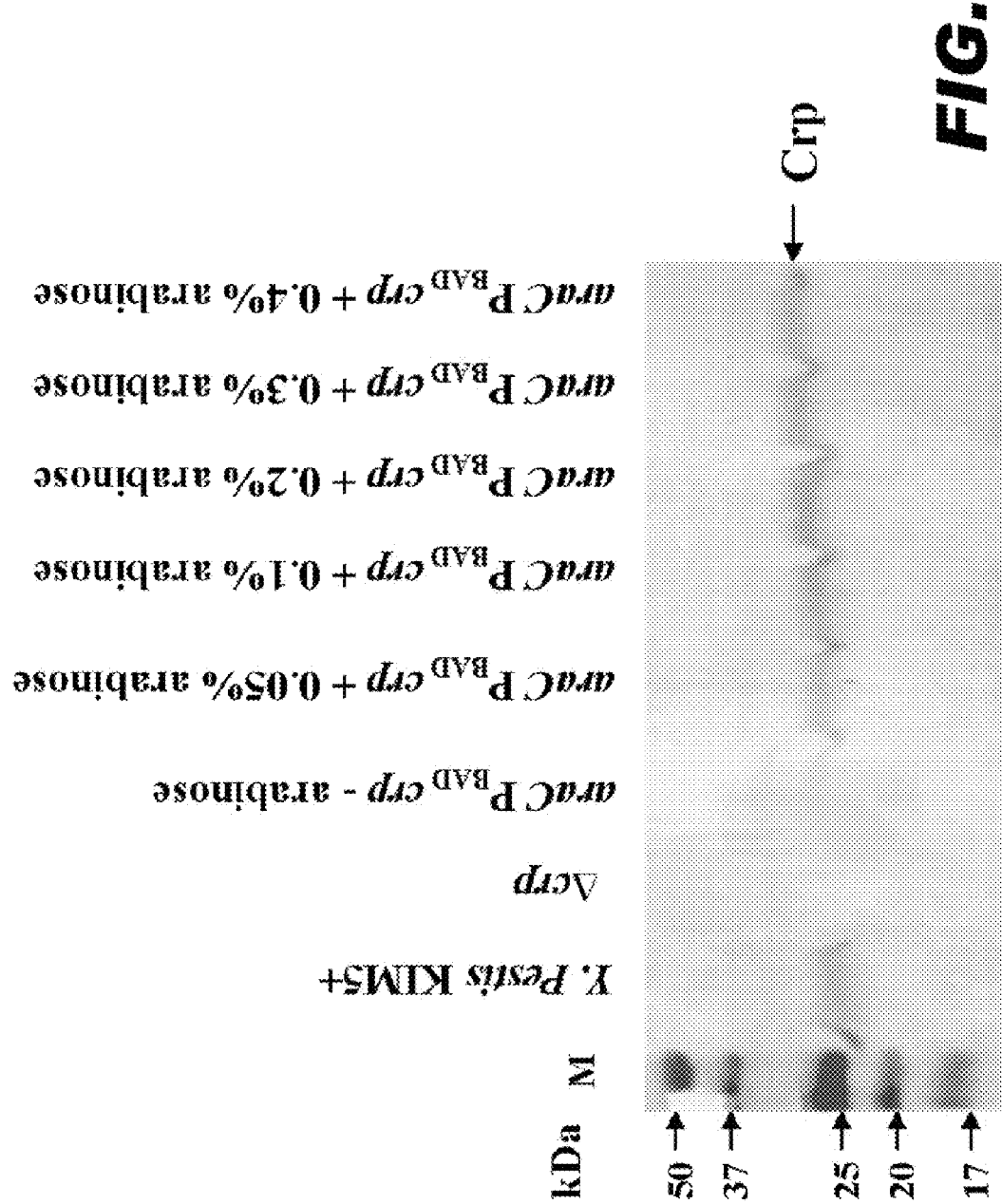

YERSINIA PESTIS VACCINE

CROSS REFERENCE TO RELATED APPLICATIONS

This application claims the priority of U.S. provisional application Ser. No. 61/294,727, filed Jan. 13, 2010, which is hereby incorporated by reference in its entirety.

GOVERNMENTAL RIGHTS

This invention was made with government support under AI057885 awarded by the National Institutes of Health. The government has certain rights in the invention.

FIELD OF THE INVENTION

The invention encompasses a recombinant *Yersinia* bacterium.

BACKGROUND OF THE INVENTION

Plague remains one of the most feared infectious diseases in humans. The etiological agent of the disease, *Yersinia pestis*, is disseminated by fleas and infects both humans and rodents. *Y. pestis* rapidly invades from the infection site into the lymphatic system and circulation, to produce the systemic and often fatal disease. Plague is endemic in many areas of the world, including the western United States. Globally about 2000 cases of plague are reported to the World Health Organization each year. Most of these cases are the bubonic form of the disease, usually a consequence of the transmission of bacteria to humans via bites from fleas that have previously fed on infected rodents. Although the most common mode of transmission is the flea bite, oral transmission can occur, often the result of an animal (polecat, weasel, ferret, cat) feeding on an infected mouse or other small rodent. Although less common, contact with domestic cats that have been exposed to *Y. pestis* is an important transmission mode because of the higher than average incidence of pneumonic plague that occurs in these cases. More rarely, cases of pneumonic plague are reported that are characterized by a short incubation period of 2 to 3 days and a high rate of mortality, even if treated. Pneumonic plague can be transmitted person-to-person or animal-to-person via the inhalation of contaminated air droplets. Pneumonic plague is the most likely form to be encountered if *Y. pestis* is used as a biological weapon.

Recent efforts to create a safe and effective pneumonic plague vaccine have focused on the development of recombinant subunit vaccines that elicit antibodies against two well characterized *Y. pestis* antigens, the F1 capsule and the virulence protein LcrV. In the past, live attenuated vaccine strains were generated by selection, rather than precise genetic manipulation, thus raising concern about their genetic composition and stability. An early live plague vaccine strain, EV76, has been used in some countries. However, EV76 has been known to cause disease in primates, raising questions about its suitability as a human vaccine. There is a need in the art, therefore, for a live plague vaccine using an adequately attenuated, rationally designed *Y. pestis* strain. This will provide the advantage of simultaneous priming against more than one antigen, thereby greatly enhancing the likelihood of broad-based protection.

SUMMARY OF THE INVENTION

One aspect of the present invention encompasses a recombinant *Yersinia* bacterium, wherein the bacterium comprises a regulated attenuation mutation.

Another aspect of the present invention encompasses a vaccine. The vaccine comprises a recombinant *Yersinia* bacterium, wherein the bacterium comprises a regulated attenuation mutation.

Yet another aspect of the present invention encompasses a method for eliciting both a humoral and a cellular immune response to *Yersinia* in a host. The method comprises administering a vaccine to a subject. The vaccine generally comprises a recombinant *Yersinia* bacterium, wherein the bacterium comprises a regulated attenuation mutation.

Still another aspect of the present invention encompasses a method for eliciting a protective immune response against bubonic and pneumonic plaque. The method comprises administering a vaccine to a subject. The vaccine generally comprises a recombinant *Yersinia pestis* bacterium, wherein the bacterium comprises a regulated attenuation mutation.

Other aspects and iterations of the invention are described more thoroughly below.

BRIEF DESCRIPTION OF THE FIGS.

The application file contains at least one photograph executed in color. Copies of this patent application publication with color photographs will be provided by the Office upon request and payment of the necessary fee.

FIG. 1 depicts a schematic chromosome structure of *Y. pestis* KIM6+, χ10003 (ΔrelA233), χ10004 (ΔrelA233ΔspoT85) and χ10019 (ΔrelA233ΔspoT85ΔlacZ::TT araC $P_{BAD}$ spoT).

FIG. 2 depicts TLC analysis of (p)ppGpp synthesis in *Y. pestis* KIM6+ and ΔrelA ΔspoT mutants during amino acid and carbon starvation. Total intracellular nucleotides were extracted from *Y. pestis* cultures uniformly labeled with [$^{32}$P] H$_3$PO$_4$. Cells were grown in modified PMH2 medium lacking L-phenylalanine for amino acid starvation (A) and in modified PMH2 medium without glucose for carbon starvation (B).

FIG. 3 depicts a schematic chromosome structure of *Y. pestis* KIM6+, χ10021 (spoT412:: 3× flag-kan), χ10019 (ΔrelA233 ΔspoT85 ΔlacZ516::TT araC $P_{BAD}$ spoT) and χ10022 (ΔrelA233 ΔspoT85 ΔlacZ516 ΩTT araC $P_{BAD}$ spoT413:: 3×flag-kan).

FIG. 4 depicts measurement of SpoT expression M, protein marker; 1, *Y. pestis* KIM6+; 2, χ10021; 3, χ10022 (without arabinose); 4, χ10022 (with 0.05% arabinose); 5, χ10022 (with 0.1% arabinose); 6, χ10022 (with 0.15% arabinose); 7, χ10022 (with 0.2% arabinose); 8, χ10022 (with 0.3% arabinose).

FIG. 5 depicts growth of *Y. pestis* strains in HIB medium at different temperatures (A) Growth curve at 26° C.; (B) Growth curve at 37° C. ●, *Y. pestis* KIM5+; ■, χ10003 (pCD1Ap) (ΔrelA233) ▲, χ10004(pCD1Ap) (ΔrelA233ΔspoT85); ▼, χ10019(pCD1Ap) (ΔrelA233 ΔspoT85 ΔlacZ::TT araC $P_{BAD}$ spoT) without arabinose; ◆, χ10019(pCD1Ap) (ΔrelA233 ΔspoT85 ΔlacZ::TT araC $P_{BAD}$ spoT) with 0.05% arabinose.

FIG. 6 depicts the analysis of virulence factor expression and secretion in *Y. pestis* KIM5+ and mutants. (A) Evaluation of virulence factor transcription by semi-quantitative RT-PCR. (B) Measurement of secreted virulence factors in culture supernatants by western blotting. Secreted proteins were collected from the culture medium following the removal of bacterial cells. Proteins were separated by SDS-PAGE and detected by western blotting. For each sample, the same amount of total protein was loaded.

Figure 9A:
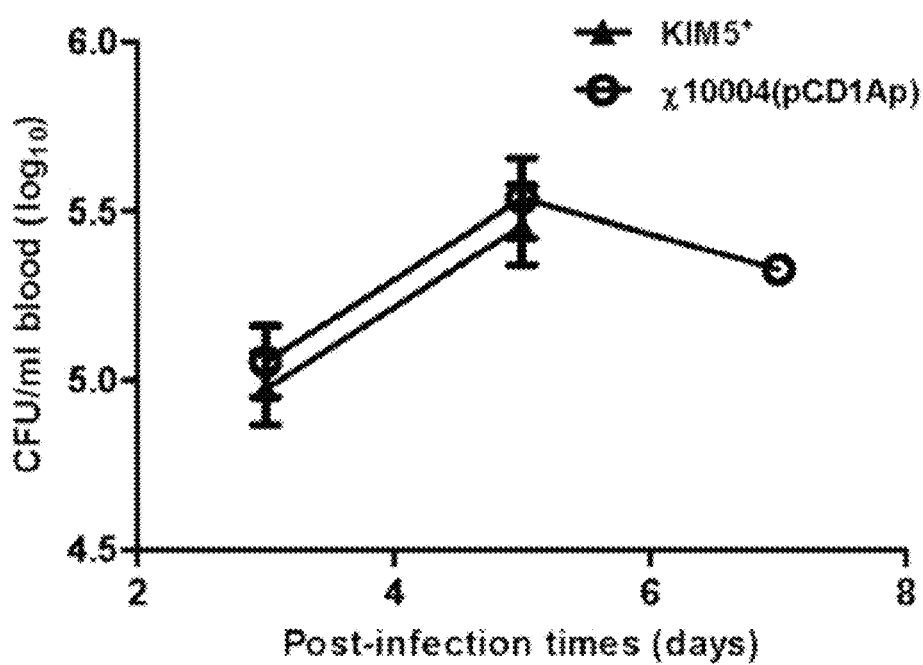
Figure 9:
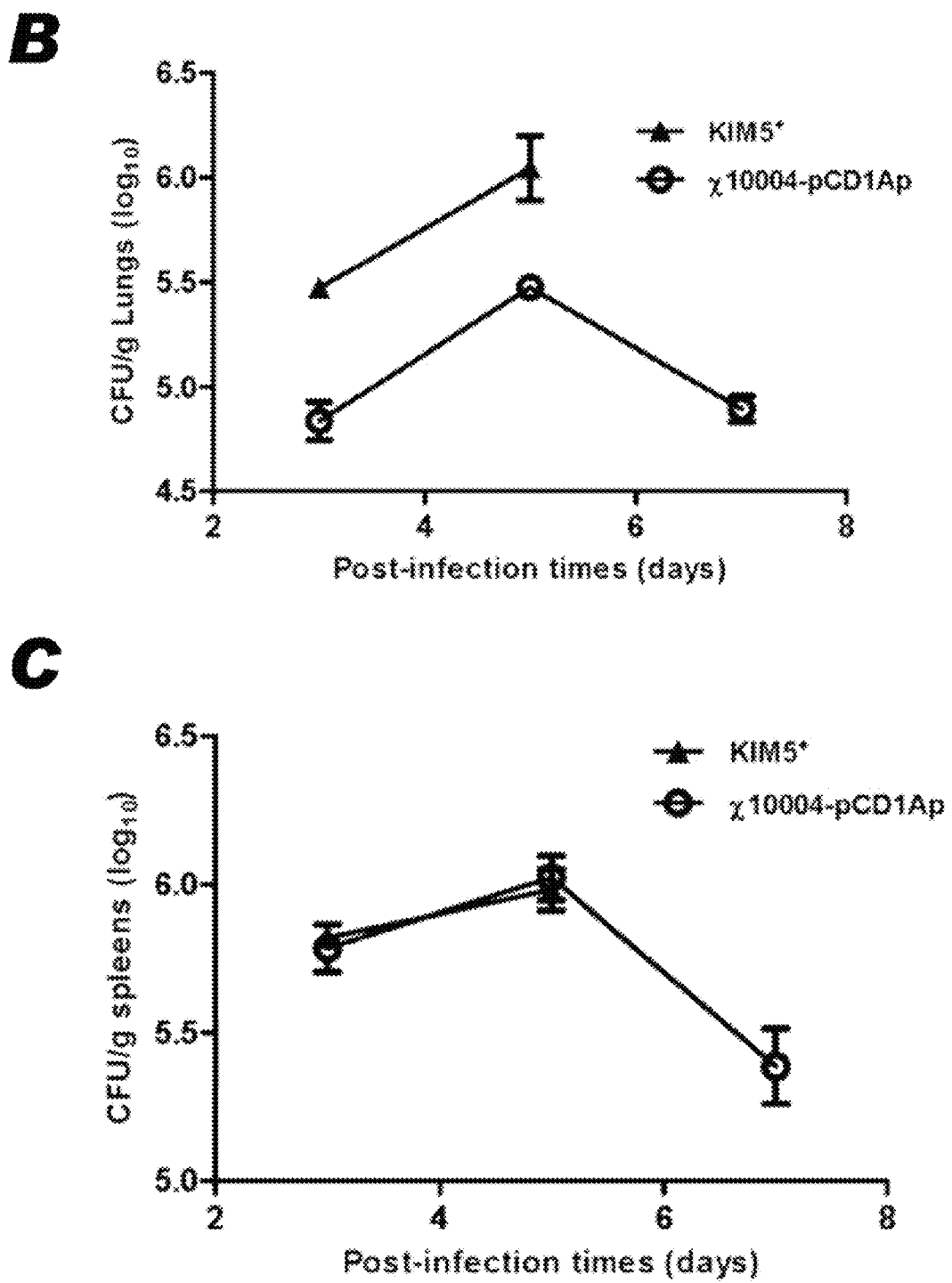
Figure 9D:
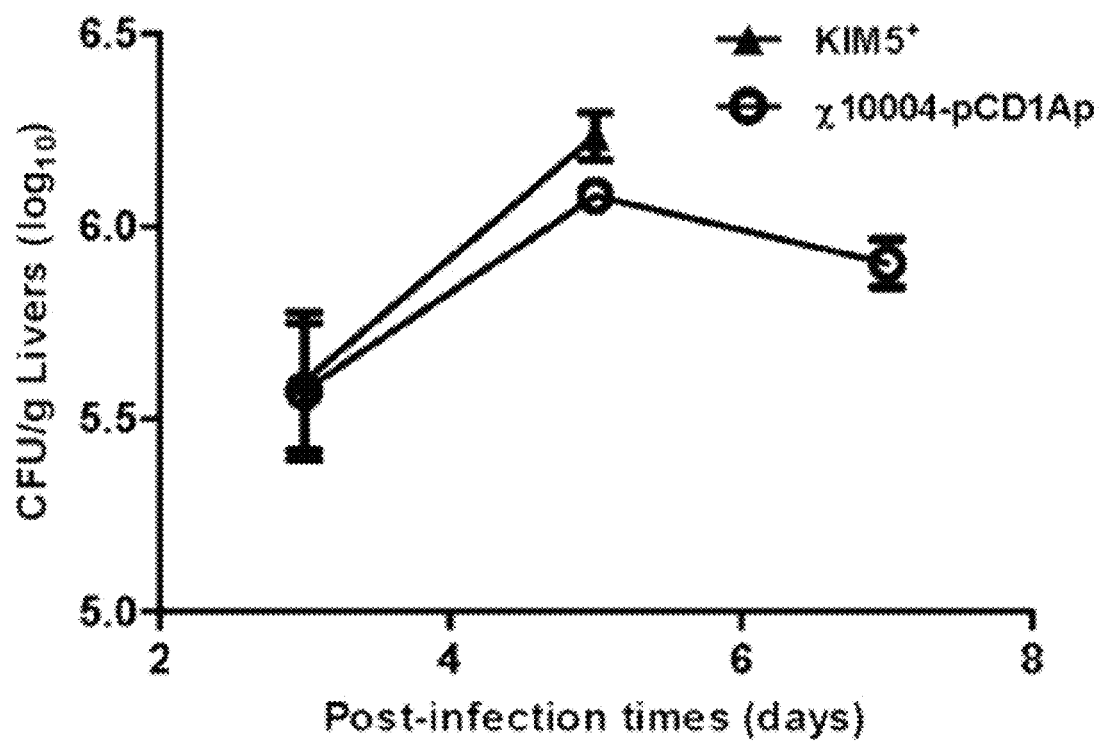

FIG. 9 depicts the kinetics of infection with *Y. pestis* KIM5+ (black) or χ10004(pCD1Ap) (white) in mouse tissues. Groups of nine mice were inoculated s.c., and at various times CFU per organ in the blood (A), lungs (B), spleens (C) and livers (D) were determined for 3 mice per group. Error bars represent standard deviation.

FIG. 10 depicts the antibody response in sera of mice inoculated with *Y. pestis* KIM5+ or χ10004(pCD1Ap). A *Y. pestis* whole cell lysate was used as the coating antigen. (A) Serum IgG responses. (B) Serum IgG1 and IgG2a responses. *, the P value was less than 0.01; **, the P value was less than 0.05.

Figure 11:
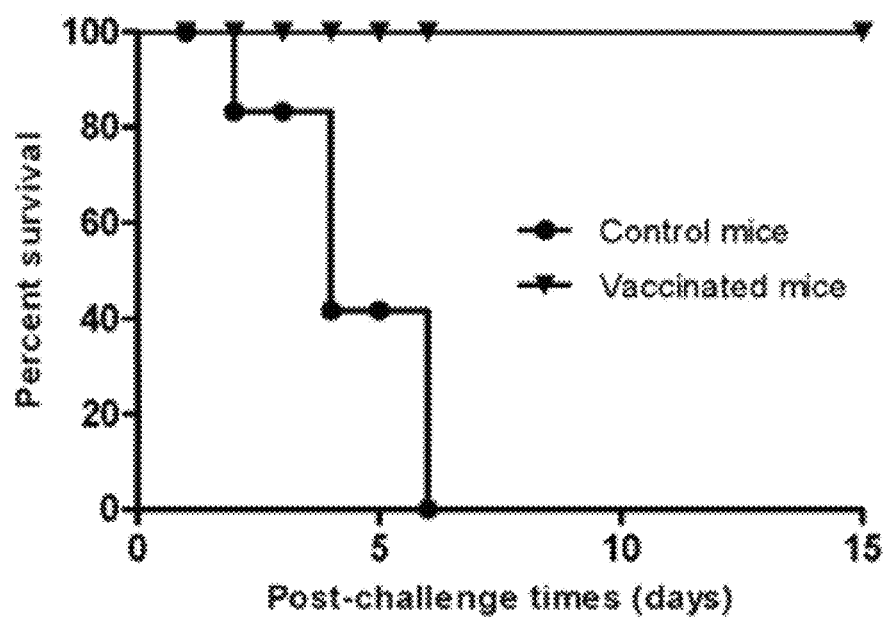
Figure 11:
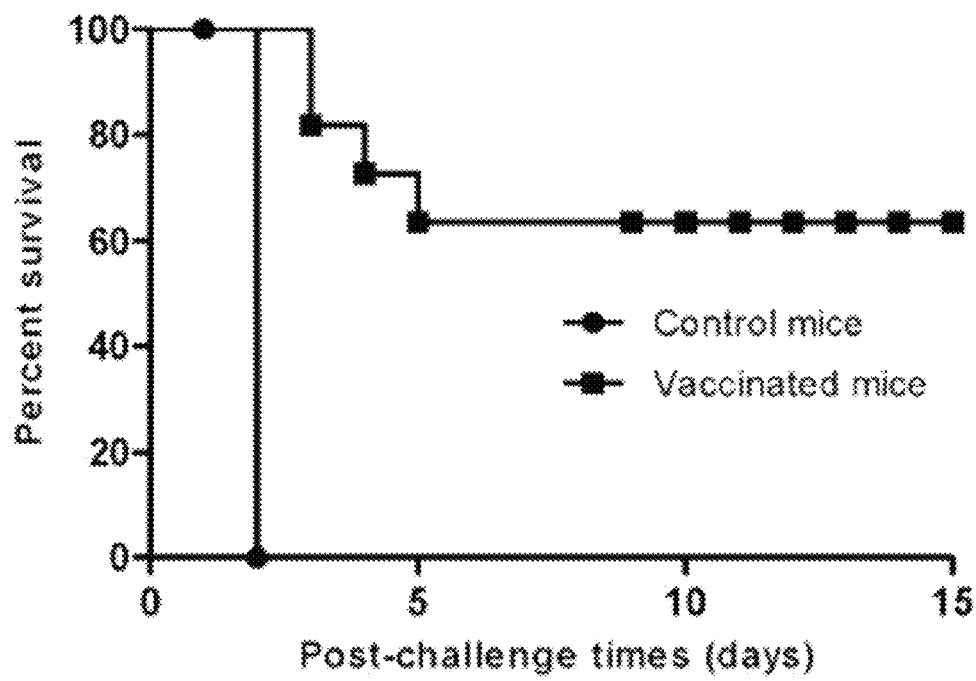

FIG. 11 depicts mouse survival after *Y. pestis* KIM5+ challenge. (A) Swiss Webster mice vaccinated s.c. with $2.5\times10^4$ CFU of χ10004(pCD1Ap) and a were challenged with $1.5\times10^5$ CFU of *Y. pestis* KIM5+ via the s.c. route. (B) Swiss Webster mice vaccinated s.c. with $2.5\times10^4$ CFU of χ10004 (pCD1Ap) were challenged via the i.n. route with $2\times10^4$ CFU of *Y. pestis* KIM5+. Immunization provided significant protection against both challenge routes (P<0.001). For each experiment, there were 10 mice in the vaccinated group and 4 mice in the control group.

Figure 12:
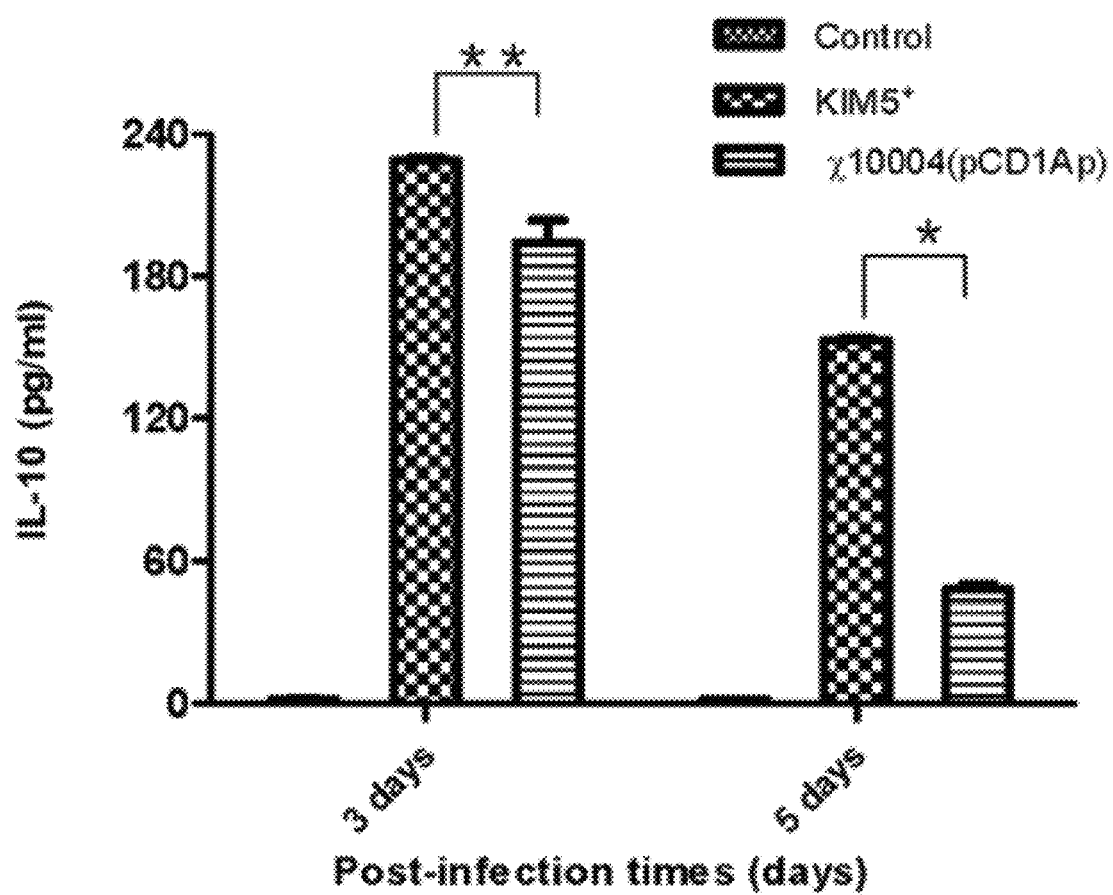

FIG. 12 depicts IL-10 production in sera of mice inoculated with *Y. pestis* KIM5+ or χ10004(pCD1Ap). *, the P value was less than 0.01; **, the P value was less than 0.05.

Figure 13:
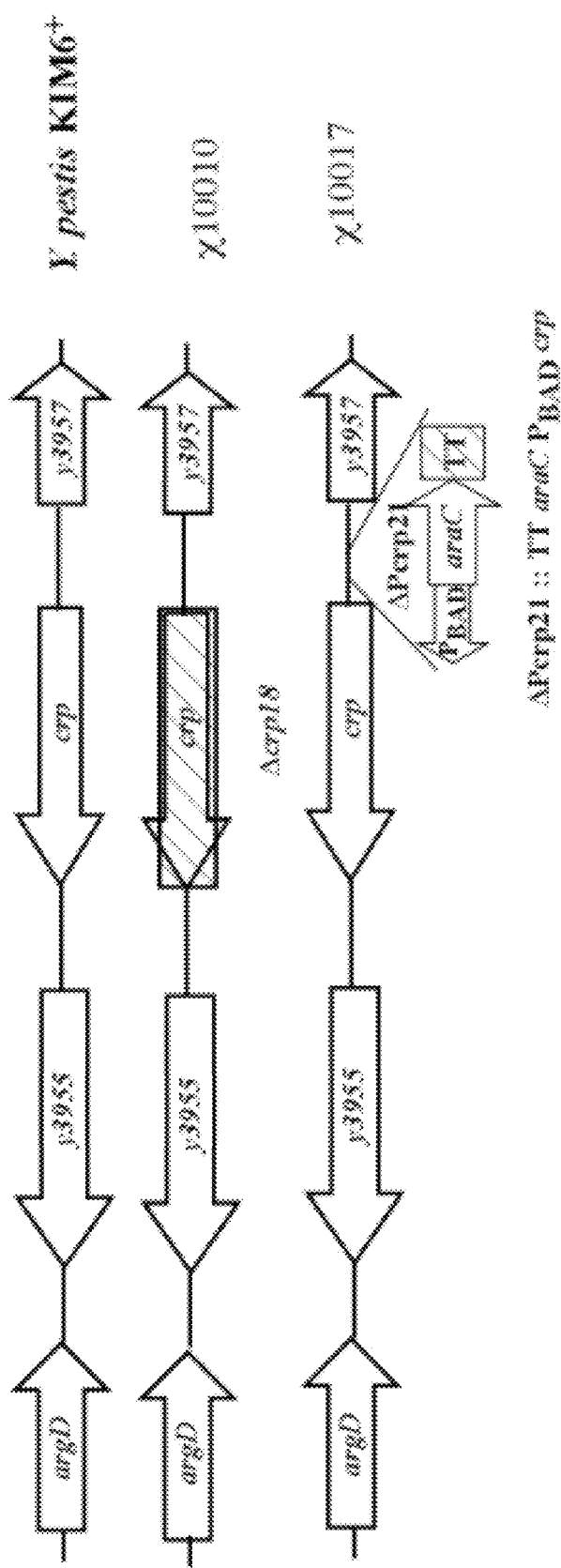

FIG. 13 depicts the structure of chromosomal region of *Y. pestis* strains KIM6+, χ10010, and χ10017.

Figure 14B:
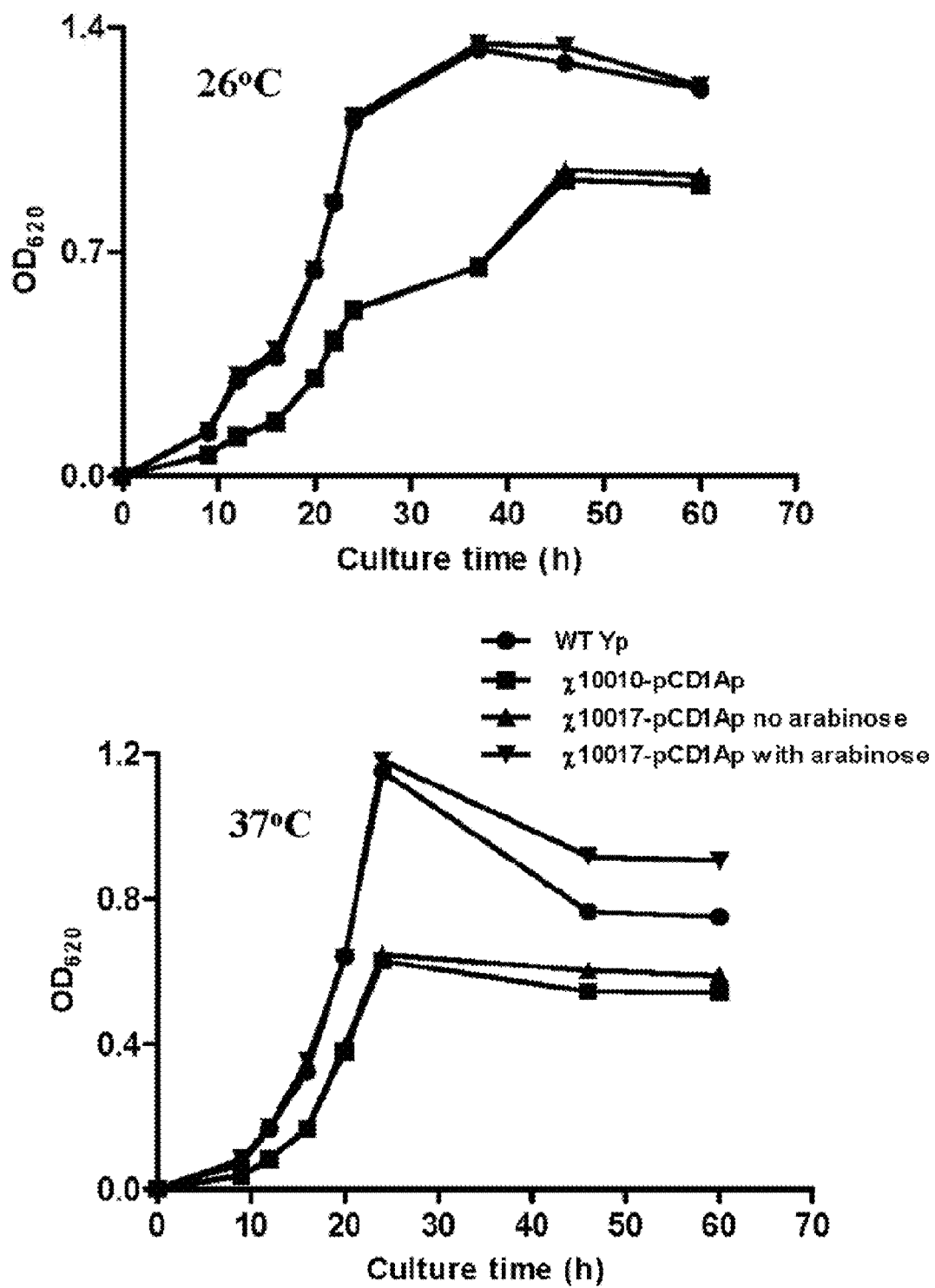

FIG. 14 depicts Crp synthesis and growth of *Y. pestis* mutants. (A) Measurement of Crp synthesis in *Y. pestis* KIM5+, χ10010 (crp18) and χ10017 (araC $P_{BAD}$ crp). Strains were grown in HIB at 37° C. overnight and Crp synthesis was detected by western blot using anti-Crp sera. M, protein marker. (B) Growth of *Y. pestis* strains in HIB medium at 26° C. or 37° C. ●, *Y. pestis* KIM5+; ■, χ10010(pCD1Ap) (Δcrp); ▲χ10017(pCD1Ap) (araC $P_{BAD}$ crp) without arabinose; ▼, χ10017(pCD1Ap) with 0.05% arabinose.

Figure 15:
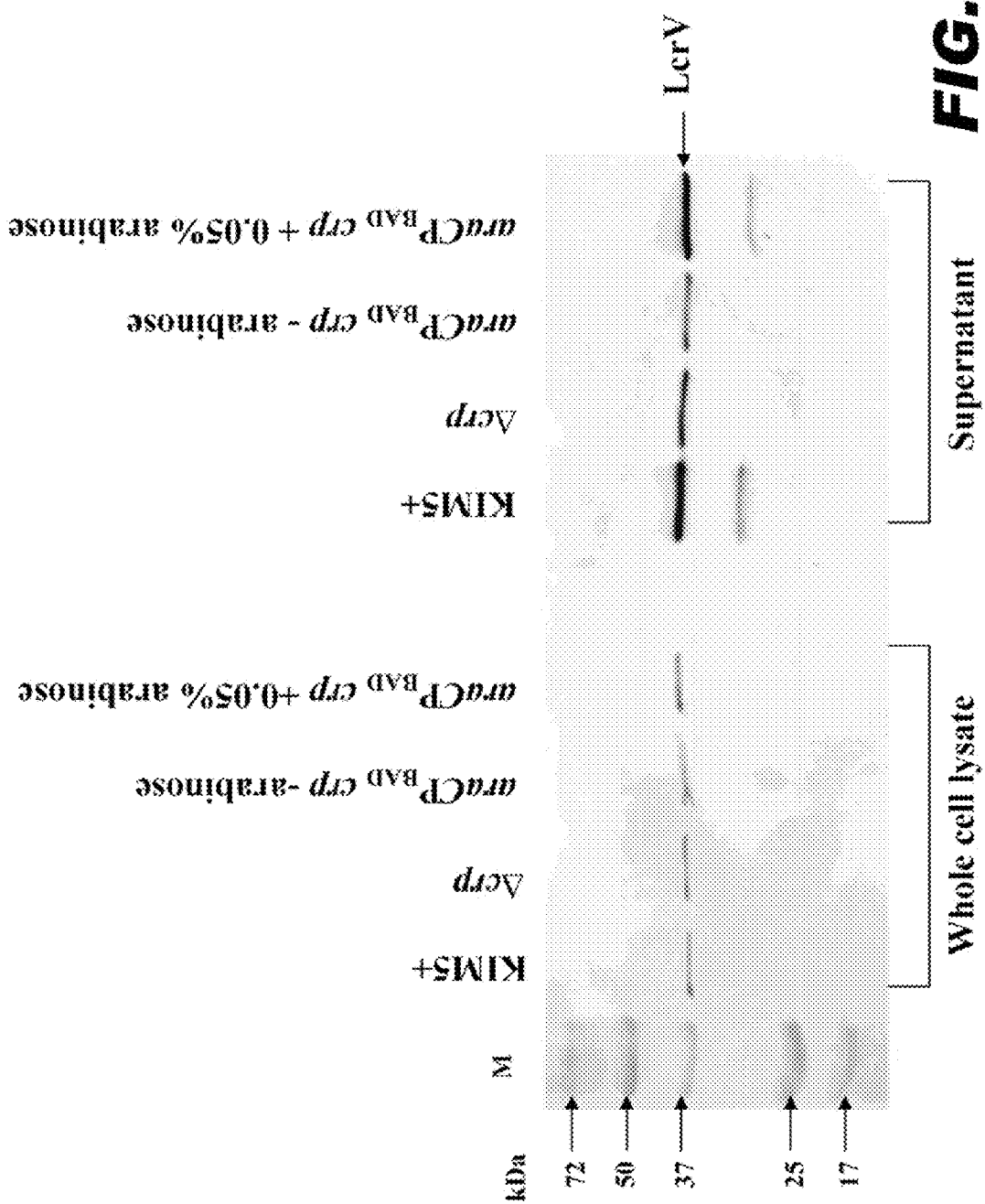

FIG. 15 depicts the measurement of LcrV synthesis and secretion in *Y. pestis* by western blot analysis. Whole cell lysates and supernatant fractions were separated by SDS-PAGE and detected by western blotting. For each sample, equivalent amounts of protein were loaded. The araC $P_{BAD}$ crp strain χ10017(pCD1Ap) was grown with and without 0.05% arabinose.

Figure 16:
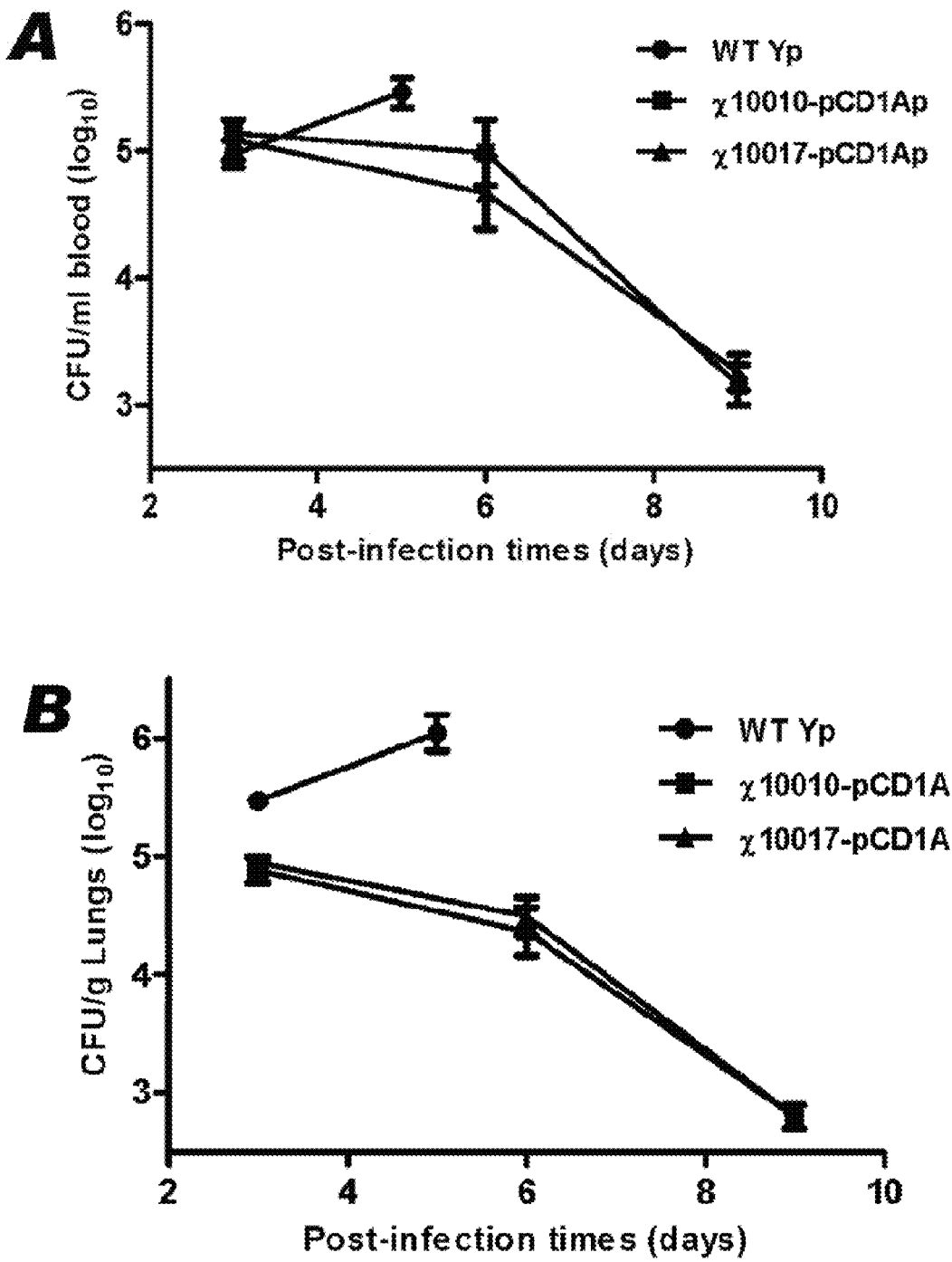
Figure 16:
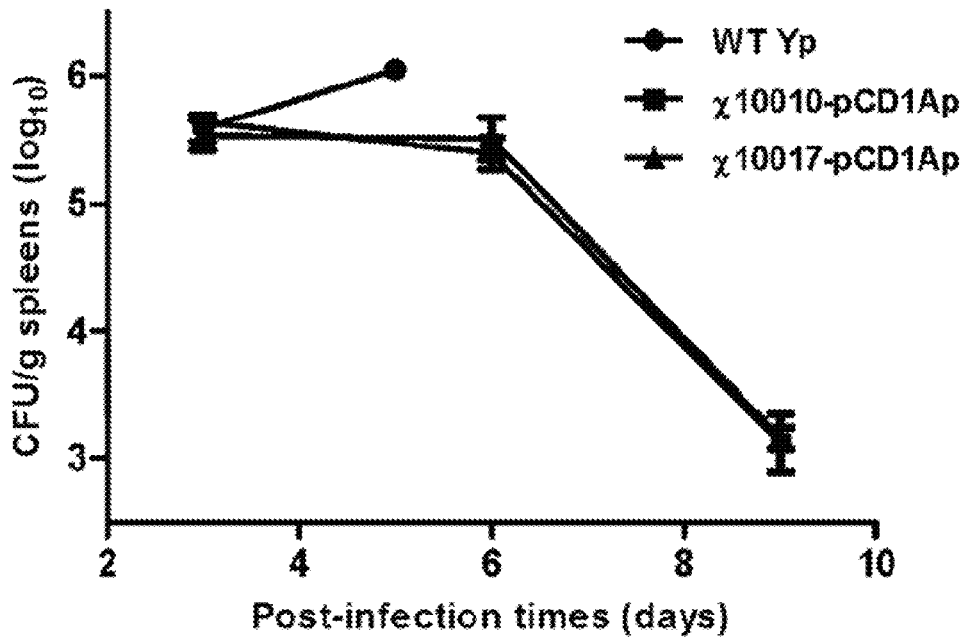
Figure 16:
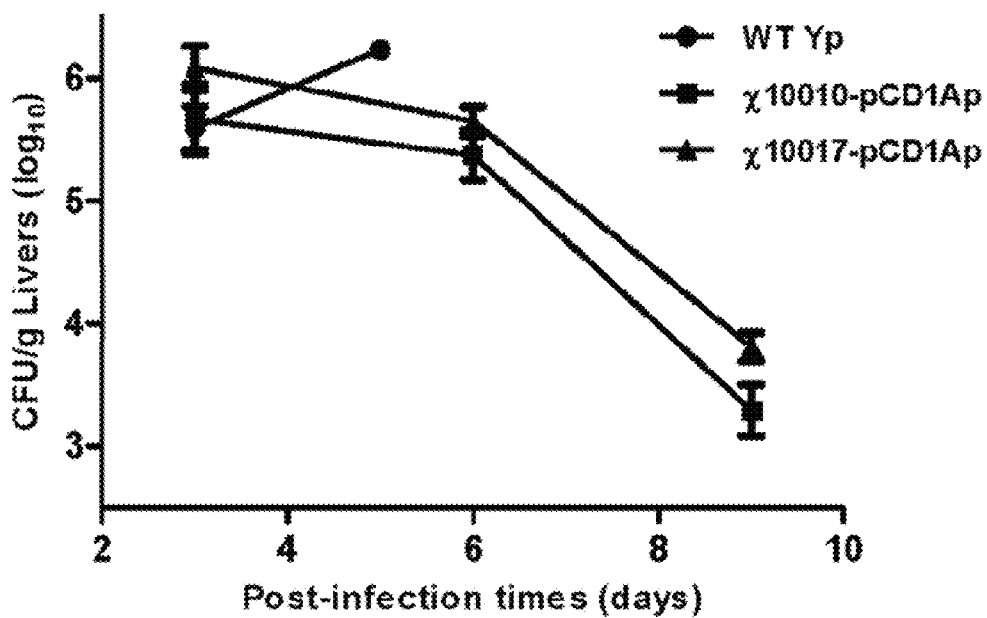

FIG. 16 depicts kinetics of infection with *Y. pestis* KIM5+ and mutant derivatives in mouse tissues. Bacteria were inoculated s.c., with $1.5\times10^3$ CFU of *Y. pestis* KIM5+, $4.2\times10^7$ CFU of χ10010(pCD1Ap) or $3.8\times10^6$ CFU of χ10017 (pCD1Ap) and at various times CFU per organ in the blood (A), lungs (B), spleens (C) and livers (D) were determined. Error bars represent standard deviations. We examined 3 mice/group/time point and the experiment was performed twice with similar results.

Figure 17:
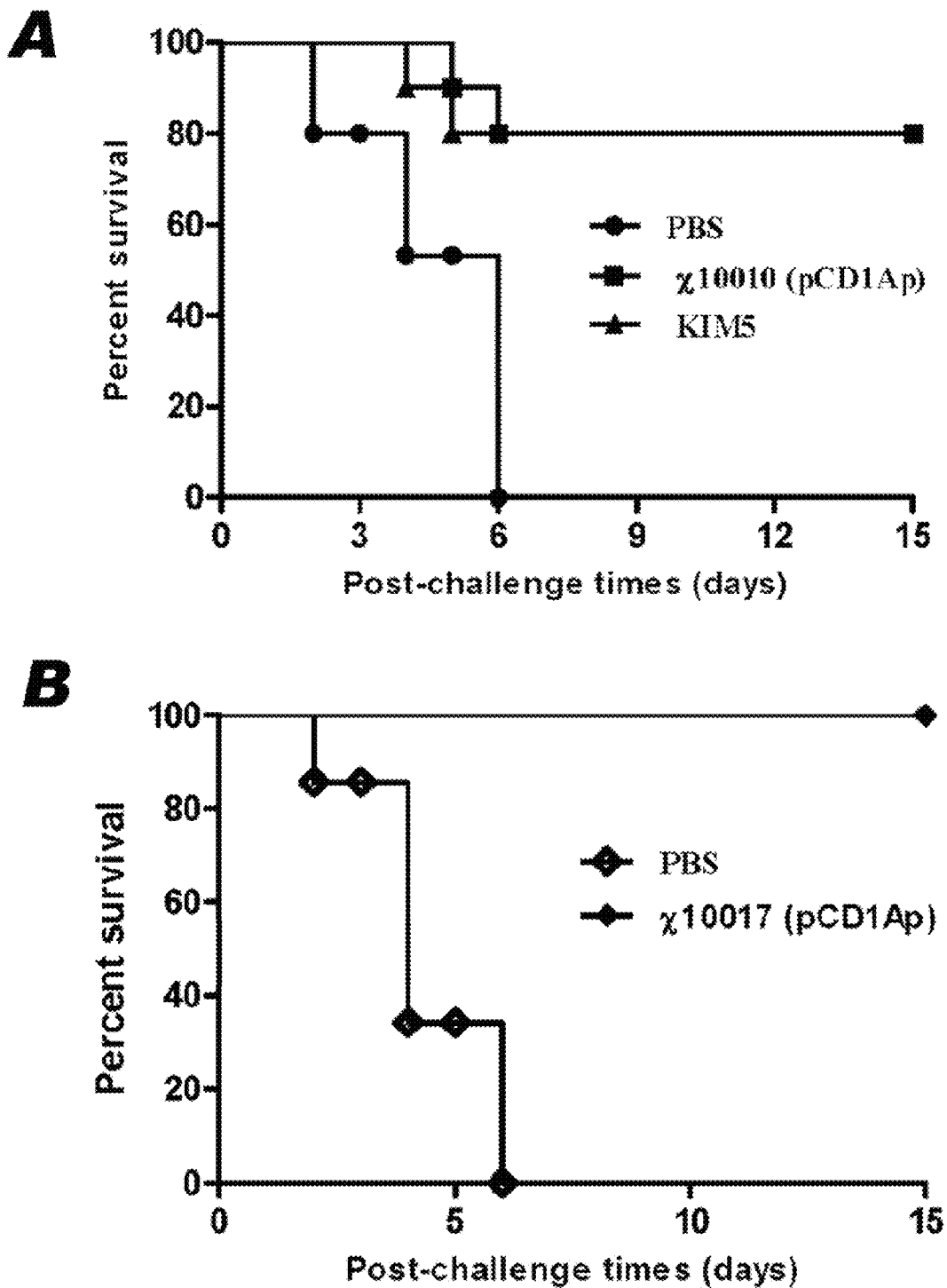
Figure 17C:
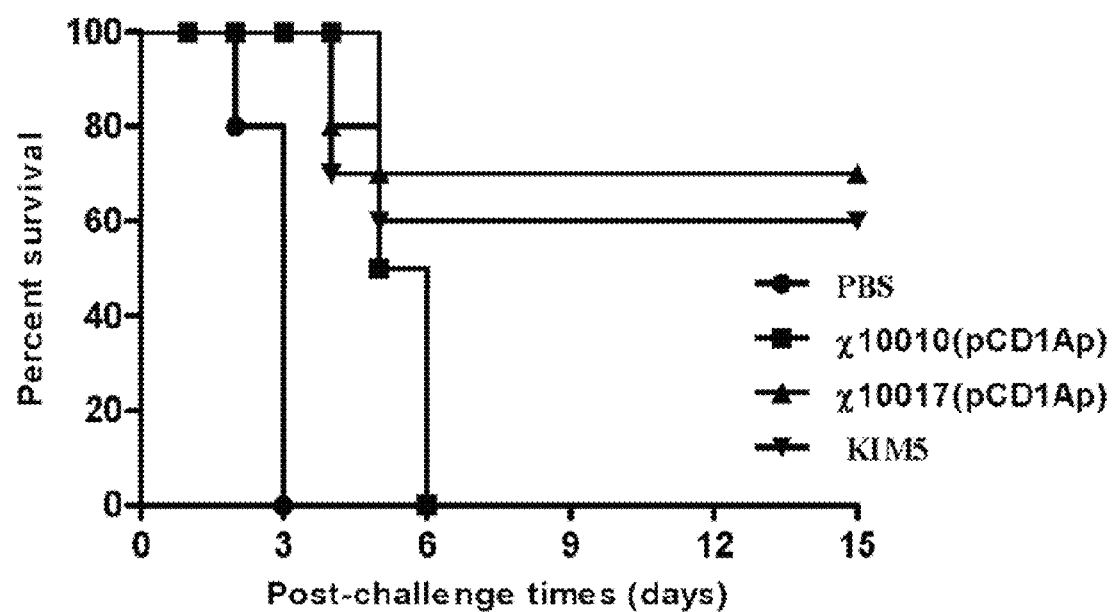

FIG. 17 depicts the survival of immunized and non-immunized mice after *Y. pestis* KIM5+ challenge. (A) Swiss Webster mice vaccinated s.c. with $3.8\times10^7$ CFU of χ10010 (pCD1Ap) or $2.5\times10^7$ CFU of *Y. pestis* KIM5 (Pgm⁻) were challenged with $1.3\times10^7$ CFU of *Y. pestis* KIM5+ via the s.c. route. (B) Swiss Webster mice vaccinated s.c. with $3.0\times10^4$ CFU of χ10017(pCD1Ap) were challenged with $1.4\times10^5$ CFU of *Y. pestis* KIM5+ via the s.c. route. (C) Swiss Webster mice vaccinated s.c. with $3.8\times10^7$ CFU of χ10010(pCD1Ap), $3.0\times10^4$ CFU of χ10017(pCD1Ap) or $3.8\times10^7$ CFU of χ10010(pCD1Ap) were challenged via the i.n. route with $1.4\times10^4$ CFU of *Y. pestis* KIM5+. For panels A and B, survival of immunized mice was significantly greater than PBS controls in all experiments (P<0.001). For panel C, survival of mice immunized with χ10017(pCD1Ap) or KIM5 was significantly greater than mice immunized with strain χ10010 (pCD1Ap) or PBS controls (P<0.001). There were 10 mice per vaccination group and 4 mice per control group for each experiment. The experiment was performed twice.

Figure 18A:
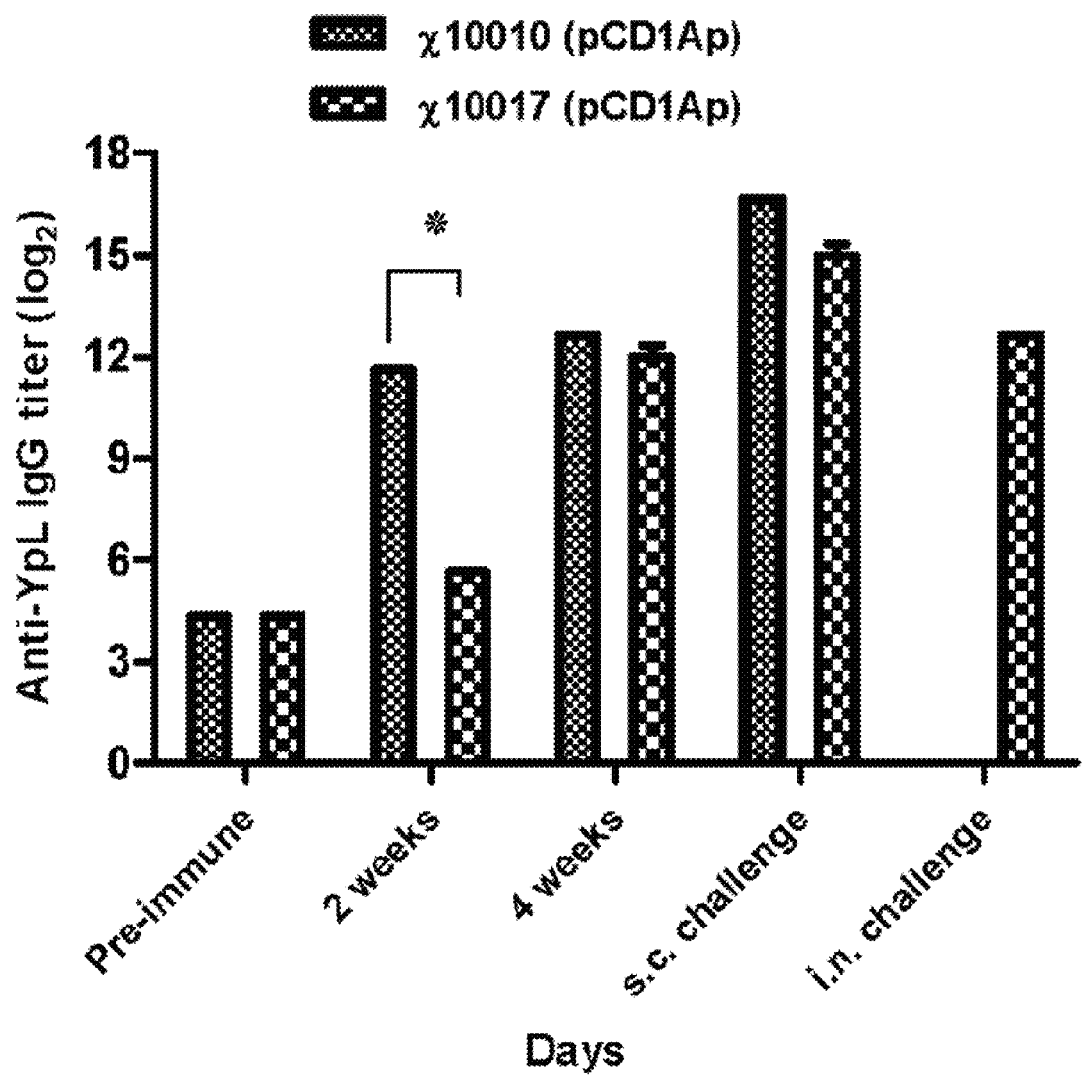
Figure 18B:
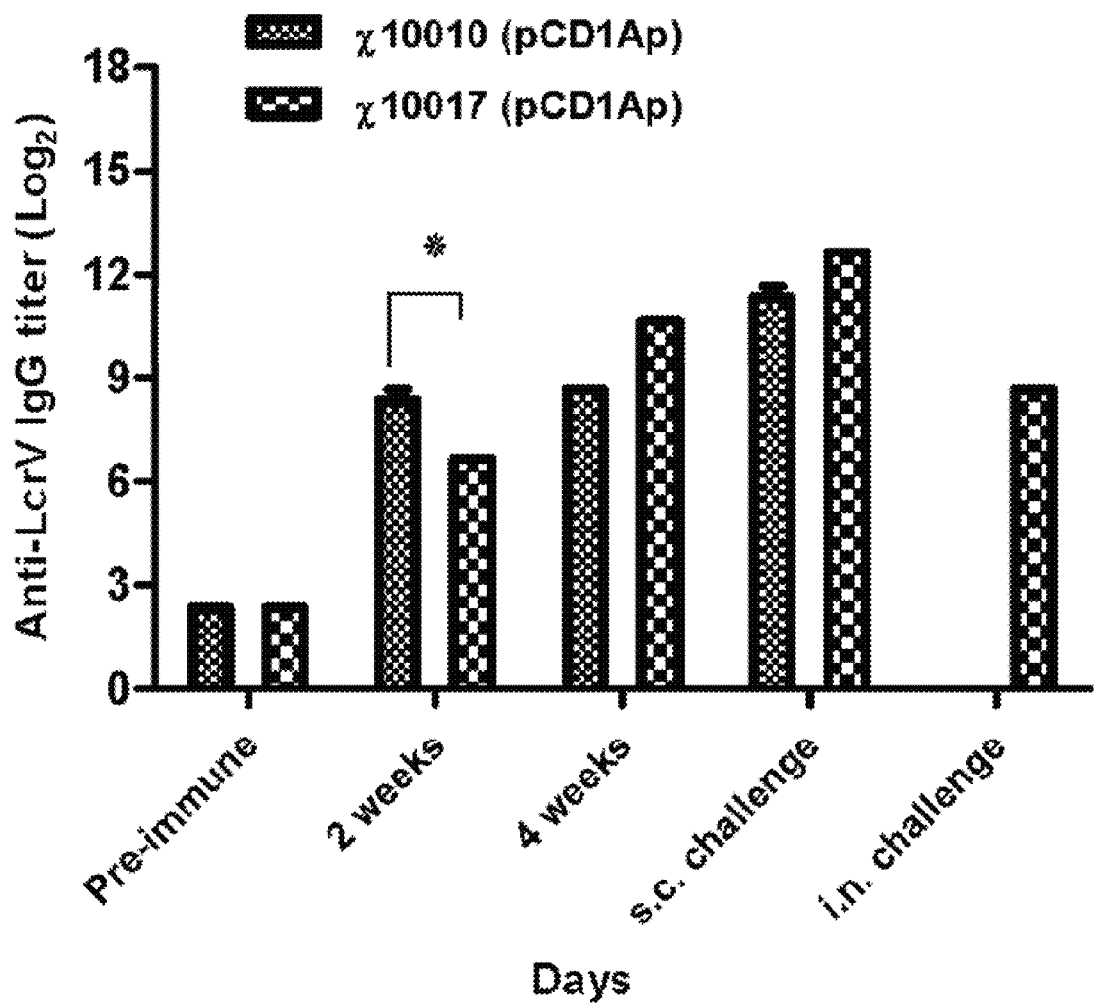
Figure 19A:
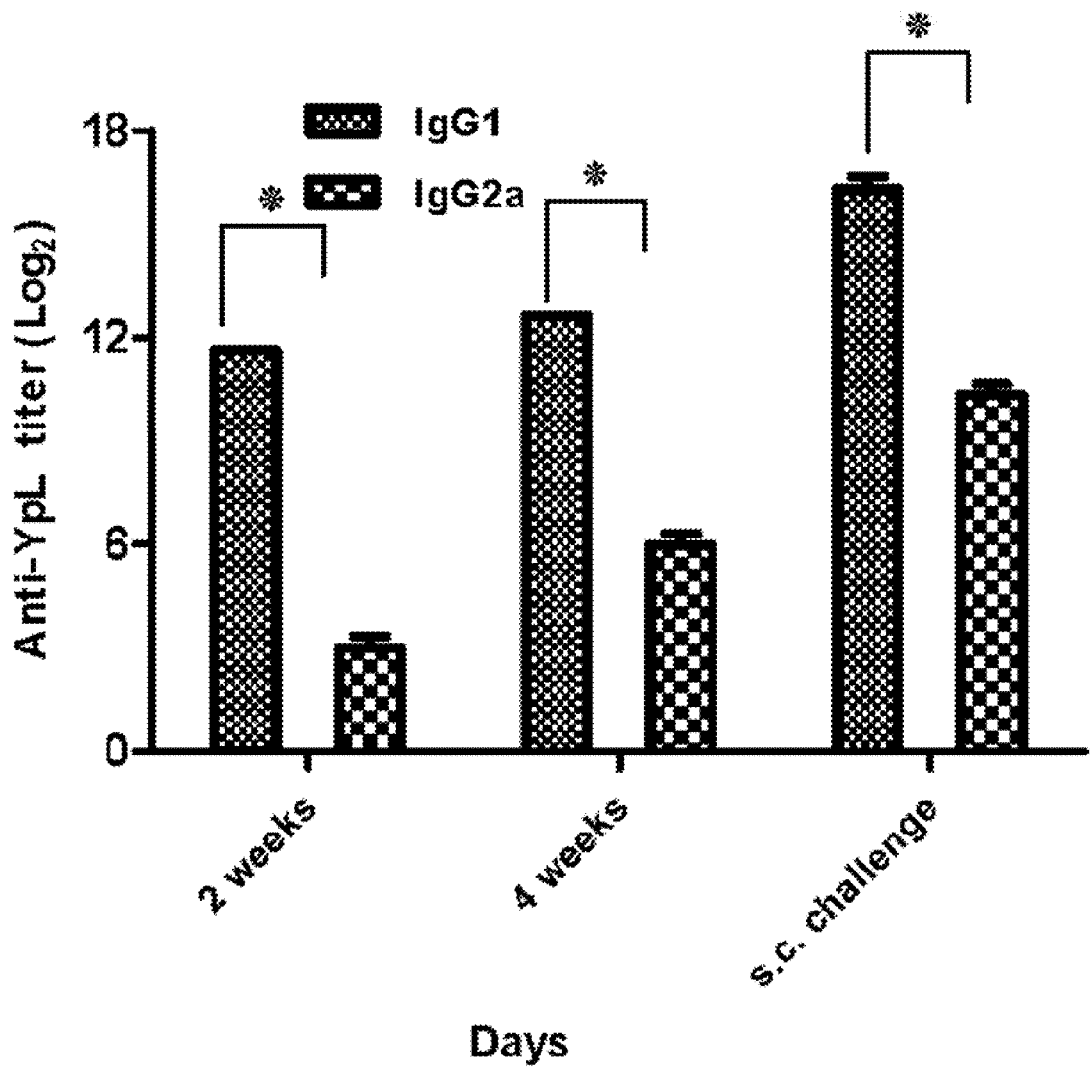
Figure 19B:
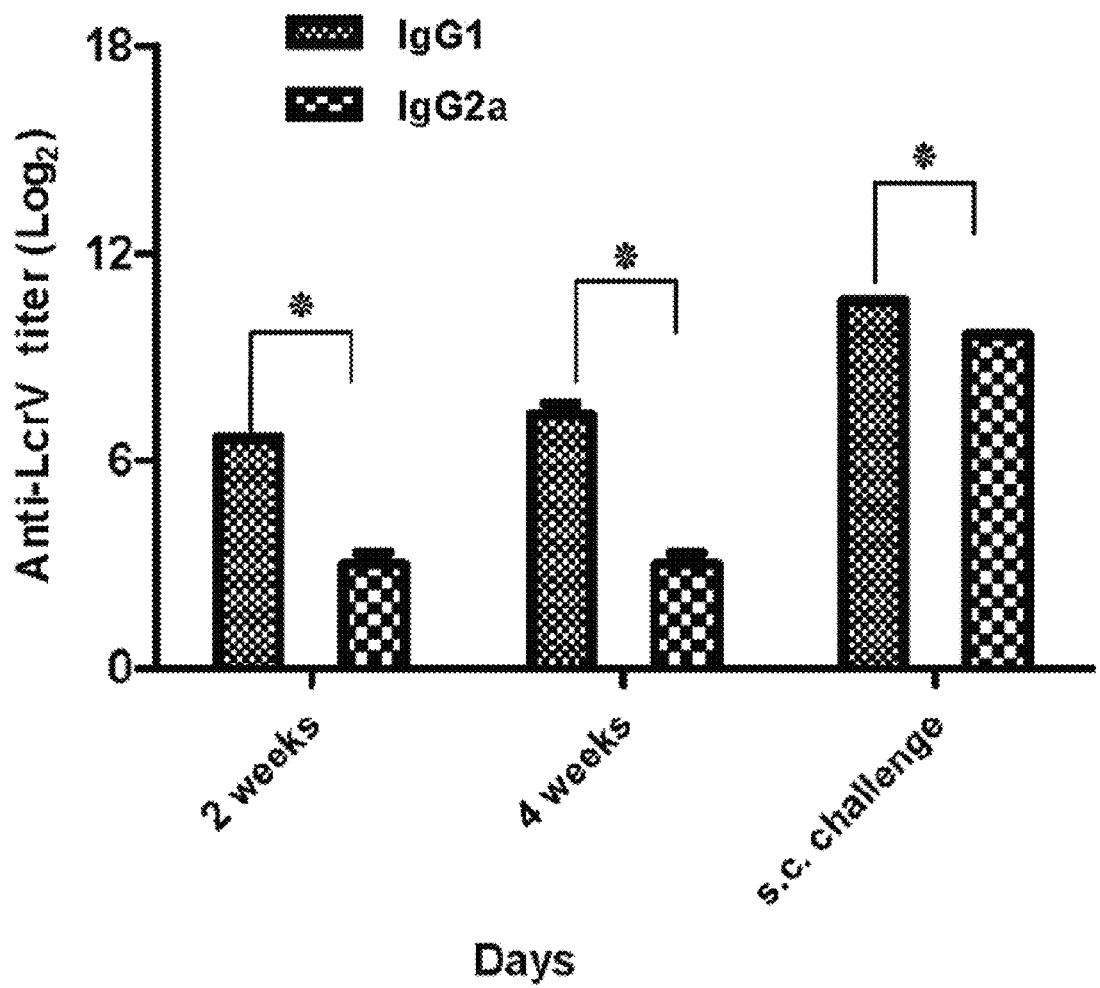
Figure 19C:
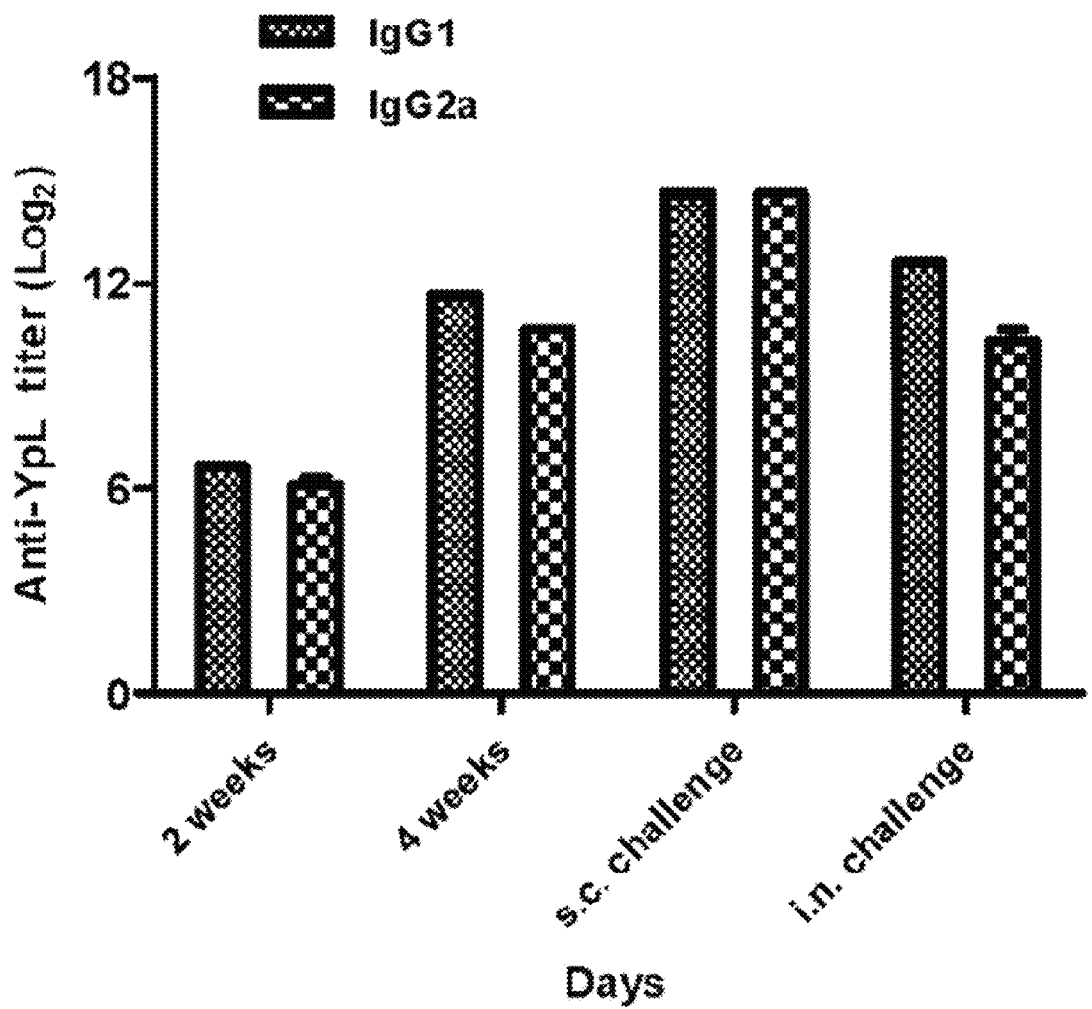
Figure 19D:
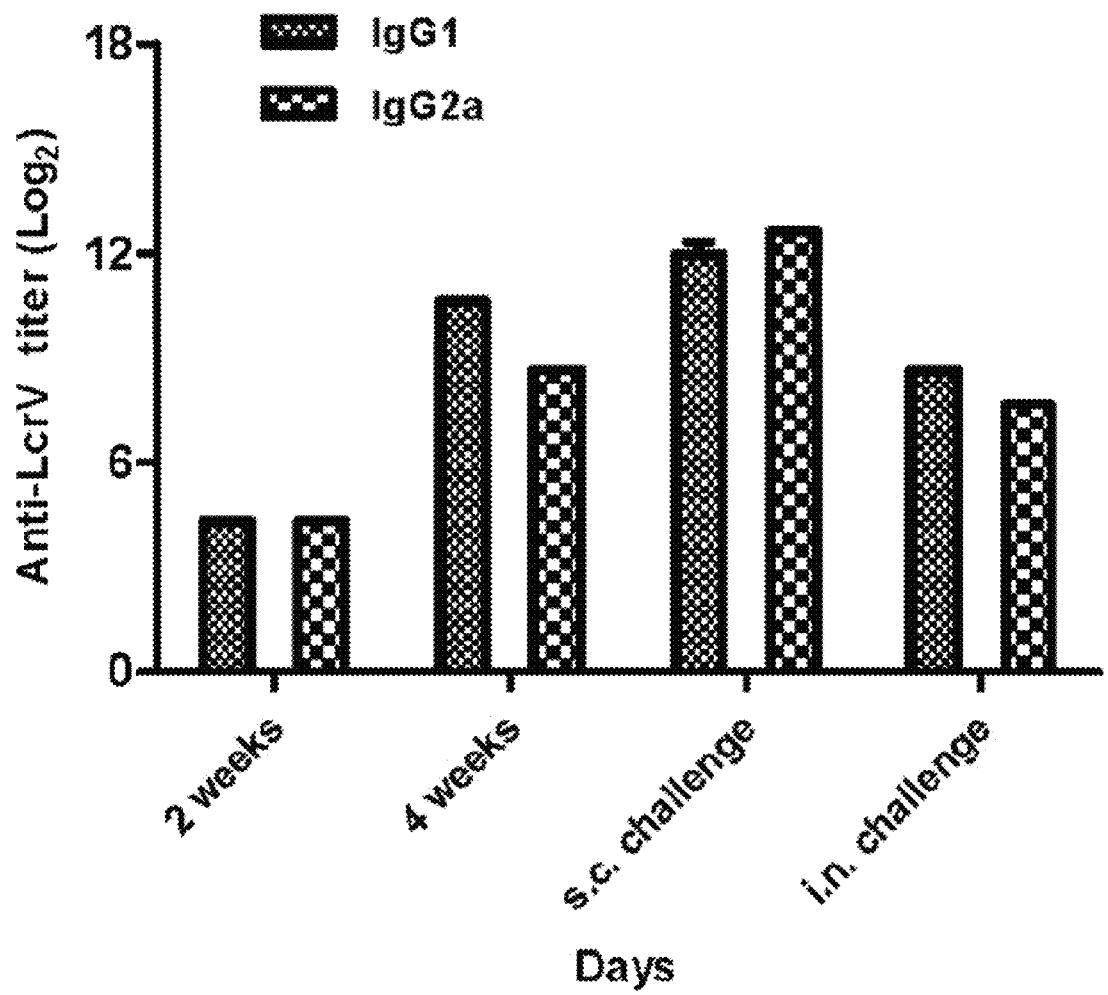

FIG. 18 depicts the IgG response in sera of mice inoculated with χ10010(pCD1Ap) or χ10017(pCD1Ap). (A) *Y. pestis* KIM5+ whole cell lysate (YpL) was used as the coating antigen; (B) recombinant LcrV was used as the coating antigen. *, P<0.01.

FIG. 19 depicts Serum IgG1 and IgG2a responses to YpL and recombinant LcrV. (A) IgG1 and IgG2a antibody levels to YpL in sera of mice immunized s.c. with χ10010(pCD1Ap); (B) IgG1 and IgG2a antibody levels to recombinant LcrV in sera of mice subcutaneously immunized with χ10010 (pCD1Ap); (C) IgG1 and IgG2a antibody levels to YpL in sera of mice subcutaneously immunized with χ10017 (pCD1Ap); (D) IgG1 and IgG2a antibody levels to recombinant LcrV in sera of mice subcutaneously immunized with χ10017(pCD1Ap). *, P<0.01.

DETAILED DESCRIPTION

The present invention encompasses a recombinant *Yersinia* bacterium. The bacterium generally comprises a regulated attenuation mutation. The bacterium may also be capable of the regulated expression of at least one nucleic acid sequence encoding an antigen of interest. The invention further comprises a vaccine comprising a recombinant *Yersinia* bacterium, and a method of eliciting an immune response to *Yersinia* or another pathogen. In exemplary embodiments, a vaccine of the invention elicits a protective immune response to both bubonic and pneumonic plague.

Several *Yersinia* species are suitable for use in the present invention. In one embodiment, a recombinant *Yersinia* bacterium of the invention may be a *Yersinia pestis* bacterium. In another embodiment, a recombinant *Yersinia* bacterium of the invention may be a *Y. enterocolitica* bacterium. In yet another embodiment, a recombinant *Yersinia* bacterium may be a *Y. pseudotuberculosis* bacterium.

I. Regulated Attenuation

The present invention encompasses a recombinant *Yersinia* bacterium capable of regulated attenuation. "Attenuation," as used herein, refers to the state of the bacterium wherein the bacterium has been weakened from its wild-type fitness by some form of recombinant or physical manipulation. This includes altering the genotype of the bacterium to reduce its ability to cause disease. However, the bacterium's ability to colonize the host and induce immune responses is, preferably, not substantially compromised. "Regulated attenuation," as used herein, refers to controlling when and/or where the bacterium is attenuated in a host. Typically, a bacterium initially colonizes the host in a non-attenuated manner, and is attenuated after several replication cycles.

A bacterium capable of regulated attenuation typically comprises a chromosomally integrated regulatable promoter. The promoter replaces the native promoter of, and is operably linked to, at least one nucleic acid sequence encoding an attenuation protein, such that the absence of the function of the protein renders the bacterium attenuated. In some embodiments, the promoter is modified to optimize the regulated attenuation.

In each of the embodiments described herein, more than one method of attenuation may be used. For instance, a recombinant bacterium of the invention may comprise a regulatable promoter chromosomally integrated so as to replace the native promoter of, and be operably linked to, at least one nucleic acid sequence encoding an attenuation protein, such that the absence of the function of the protein renders the bacterium attenuated, and the bacterium may comprise another method of attenuation detailed in section I(f) below.

(a) Attenuation Protein

Herein, "attenuation protein" is meant to be used in its broadest sense to encompass any protein the absence of which attenuates a bacterium. For instance, in some embodiments, an attenuation protein may be a protein that helps protect a bacterium from stresses encountered in the gastrointestinal tract or respiratory tract. Non-limiting examples may be the RelA, SpoT, OmpR, Crp, RpoS, Fur, Asd and MurA proteins. In other embodiments, the protein may be a necessary component of the cell wall of the bacterium. In still other embodiments, the protein may be listed in Section I(f) below.

The native promoter for a nucleic acid encoding at least one, two, three, four, or more than four attenuation proteins may be replaced by a regulatable promoter as described herein. In one embodiment, the promoter for a nucleic acid encoding one of the proteins selected from the group comprising RelA, SpoT, OmpR, and Crp may be replaced. In another embodiment, the promoter for a nucleic acid encoding two, three, or four of the proteins selected from the group comprising RelA, SpoT, OmpR, and Crp may be replaced.

If the promoter of a nucleic acid encoding more than one attenuation protein is replaced, each promoter may be replaced with a regulatable promoter, such that the expression of a nucleic acid encoding each attenuation protein is regulated by the same compound or condition. Alternatively, each promoter may be replaced with a different regulatable promoter, such that the expression of each attenuation protein encoding sequence is regulated by a different compound or condition such as by the sugars arabinose, maltose, rhamnose or xylose.

(b) Regulatable Promoter

Generally speaking, the native promoter of a nucleic acid encoding an attenuation protein may be replaced with a regulatable promoter operably linked to the nucleic acid sequence encoding an attenuation protein. The term "operably linked," as used herein, means that expression of a nucleic acid is under the control of a promoter with which it is spatially connected. A promoter may be positioned 5' (upstream) of the nucleic acid under its control. The distance between the promoter and a nucleic acid to be expressed may be approximately the same as the distance between that promoter and the native nucleic acid sequence it controls. As is known in the art, variation in this distance may be accommodated without loss of promoter function but can also be used to modulate (e.g. to increase or decrease) promoter function.

The regulatable promoter used herein generally allows transcription of the nucleic acid sequence encoding the attenuation protein while in a permissive environment (i.e. in vitro growth), but ceases transcription of the nucleic acid sequence encoding an attenuation protein while in a non-permissive environment (i.e. during growth of the bacterium in an animal or human host). For instance, the promoter may be responsive to a physical or chemical difference between the permissive and non-permissive environment. Suitable examples of such regulatable promoters are known in the art and detailed in Section II below.

In some embodiments, the promoter may be responsive to the level of arabinose in the environment. In other embodiments, the promoter may be responsive to the level of maltose, rhamnose, or xylose in the environment. The promoters detailed herein are known in the art, and methods of operably linking them to a nucleic acid sequence encoding an attenuation protein are known in the art.

In certain embodiments, a recombinant bacterium of the invention may comprise $\Delta P_{spoT}$::TT araC $P_{BAD}$ spoT or $\Delta P_{crp}$::TT araC $P_{BAD}$ crp, or a combination thereof. (P stands for promoter and TT stands for transcription terminator). Growth of such strains in the presence of arabinose leads to transcription of the spoT, and/or crp nucleic acid sequences, but nucleic acid sequence expression ceases in a host because there is no free arabinose. Attenuation develops as the products of the spoT, and/or the crp nucleic acid sequences are diluted at each cell division. Generally speaking, the concentration of arabinose necessary to induce expression is typically less than about 2%. In some embodiments, the concentration is less than about 1.5%, 1%, 0.5%, 0.2%, 0.1%, or 0.05%. In certain embodiments, the concentration may be about 0.04%, 0.03%, 0.02%, or 0.01%. In an exemplary embodiment, the concentration is about 0.05%. Higher concentrations of arabinose or other sugars may lead to acid production during growth that may inhibit desirable cell densities. The inclusion of mutations such as $\Delta araBA$ or mutations that block the uptake and/or breakdown of maltose, rhamnose, or xylose, however, may prevent such acid production and enable use of higher sugar concentrations with no ill effects.

When the regulatable promoter is responsive to arabinose, the onset of attenuation may be delayed by including additional mutations, such as $\Delta araBA$, which prevents use of arabinose retained in the cell cytoplasm at the time of oral immunization, and/or $\Delta araFGH$ that enhances retention of arabinose. Thus, inclusion of these mutations may be beneficial in at least two ways: first, enabling higher culture densities, and second enabling a further delay in the display of the attenuated phenotype that may result in higher densities of the Yersinia vaccine strain in effector lymphoid tissues to further enhance immunogenicity.

(c) Modifications

Attenuation of the recombinant bacterium may be optimized by modifying the nucleic acid sequence encoding an attenuation protein and/or promoter. Methods of modifying a promoter and/or a nucleic acid sequence encoding an attenuation protein are the same as those detailed below with respect to repressors in Section II.

In some embodiments, more than one modification may be performed to optimize the attenuation of the bacterium. For instance, at least one, two, three, four, five, six, seven, eight or nine modifications may be performed to optimize the attenuation of the bacterium.

(d) Crp Cassette

In some embodiments, a recombinant bacterium of the invention may also comprise a $\Delta P_{crp}$::TT araC $P_{BAD}$ crp deletion-insertion mutation, as described above. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional control on the expression of the nucleic acid sequence encoding an attenuation protein also controlled by an araC $P_{BAD}$ crp deletion-insertion cassette.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above (e) Regulated Expression In each of the above embodiments, a bacterium capable of regulated attenuation may also be capable of regulated expression of at least one nucleic acid encoding an antigen as detailed in section II below.

(f) Attenuation

In addition to comprising a regulated attenuation mutation, a bacterium of the invention may be further attenuated. Other methods of attenuation are known in the art. For instance, attenuation may be accomplished by altering (e.g., deleting) native nucleic acid sequences found in the wild-type bacterium. For instance, non-limiting examples of nucleic acid sequences which may be used for attenuation may include: a pab nucleic acid sequence, a pur nucleic acid sequence, an aro nucleic acid sequence, asd, a dap nucleic acid sequence, nadA, pncB, gale (lse), pmi, fur, rpsL, ompR, htrA, hemA, cya, crp, dam, phoP, phoQ, rfc, poxA, galU, mviA (hnr), sodC, recA, rpoE, flgM, tonB, slyA, pla, pabA, pabB, pabC, yopH and any combination thereof. Exemplary attenuating mutations may be designed in aroA, aroC, aroD, cya, crp, phoP, phoQ, ompR, galE (lse), pabA, pabB, pabC and htrA.

In certain embodiments, a nucleic acid sequence listed above may be placed under the control of a sugar regulated promoter wherein the sugar is present during in vitro growth of the recombinant bacterium, but substantially absent within an animal or human host. The cessation in transcription of a nucleic acid sequence listed above would then result in attenuation and the inability of the recombinant bacterium to induce disease symptoms.

In another embodiment, a recombinant bacterium may contain one and in some embodiments, more than one, deletion and/or deletion-insertion mutation present in the strains listed in Table 3. Furthermore, vectors, as listed in Table 3, and described in the Examples below, along with other plasmid vectors, may be used to introduce these deletion and deletion-insertion mutations into strains during their construction. Methods of introducing these mutations into a strain are known in the art and detailed in the Examples.

The bacterium may also be modified to create a balanced-lethal host-vector system, although other types of systems may also be used (e.g., creating complementation heterozygotes). For the balanced-lethal host-vector system, the bacterium may be modified by manipulating its ability to synthesize various essential constituents needed for synthesis of the rigid peptidoglycan layer of its cell wall. In one example, the constituent is diaminopimelic acid (DAP). Various enzymes are involved in the eventual synthesis of DAP. In one example, the bacterium is modified by using a ΔasdA mutation to eliminate the bacterium's ability to produce β-aspartate semialdehyde dehydrogenase, an enzyme essential for the synthesis of DAP. One of skill in the art can also use the teachings of U.S. Pat. No. 6,872,547 for other types of mutations of nucleic acid sequences that result in the abolition of the synthesis of DAP. These nucleic acid sequences may include, but are not limited to, dapA, dapB, dapC, dapD, dapE, dapF, and asd. Other modifications that may be employed include modifications to a bacterium's ability to synthesize D-alanine or to synthesize D-glutamic acid (e.g., ΔmurI mutations), which are both unique constituents of the peptidoglycan layer of the *Yersinia* bacterial cell wall Yet another balanced-lethal host-vector system comprises modifying the bacterium such that the synthesis of an essential constituent of the rigid layer of the bacterial cell wall is dependent on a nutrient (e.g., arabinose) that can be supplied during the growth of the microorganism. For example, a bacterium may be comprise the $\Delta P_{murA}$::TT araC $P_{BAD}$ murA deletion-insertion mutation. This type of mutation makes synthesis of muramic acid (another unique essential constituent of the peptidoglycan layer of the bacterial cell wall) dependent on the presence of arabinose that can be supplied during growth of the bacterium in vitro.

When arabinose is absent, however, as it is in an animal or human host, the essential constituent of the peptidoglycan layer of the cell wall is not synthesized. This mutation represents an arabinose-dependant lethal mutation. In the absence of arabinose, synthesis of muramic acid ceases and lysis of the bacterium occurs because the peptidoglycan layer of the cell wall is not synthesized. It is not possible to generate ΔmurA mutations because they are lethal. The necessary nutrient, a phosphorylated muramic acid, cannot be exogenously supplied because enteric bacteria cannot take the nutrient up from the media. Recombinant bacteria with a $\Delta P_{murA}$::TT araC $P_{BAD}$ murA deletion-insertion mutation grown in the presence of arabinose exhibit effective colonization of effector lymphoid tissues after oral vaccination prior to undergoing lysis due to the inability to synthesize muramic acid.

Similarly, various embodiments may comprise the araC $P_{BAD}$ c2 cassette inserted into the asd nucleic acid sequence that encodes aspartate semialdehyde dehydrogenase. Since the araC nucleic acid sequence is transcribed in a direction that could lead to interference in the expression of adjacent nucleic acid sequences and adversely affect vaccine strain performance, a transcription termination (TT) sequence is generally inserted 3' to the araC nucleic acid sequence. The chromosomal asd nucleic acid sequence is typically inactivated to enable use of plasmid vectors encoding the wild-type asd nucleic acid sequence in the balanced-lethal host-vector system. This allows stable maintenance of plasmids in vivo in the absence of any drug resistance attributes that are not permissible in live bacterial vaccines. In some of these embodiments, the wild-type asd nucleic acid sequence may be encoded by the vector described above. The vector enables the regulated expression of an antigen encoding sequence through the repressible promoter.

In further embodiments, the bacterium may be attenuated by regulating the murA nucleic acid sequence encoding the first enzyme in muramic acid synthesis and the asd nucleic acid sequence essential for DAP synthesis. This host-vector grows in LB broth with 0.1% L-arabinose, but is unable to grow in or on media devoid of arabinose since it undergoes cell wall-less death by lysis. In some embodiments of the invention, the recombinant bacterium may comprise araBA and araFGH mutations to preclude breakdown and leakage of internalized arabinose such that asd and murA nucleic acid sequence expression continues for a cell division or two after oral immunization into an environment that is devoid of external arabinose.

II. Regulated Expression

The present invention encompasses a recombinant bacterium capable of the regulated expression of at least one nucleic acid sequence encoding an antigen of interest. The regulated expression may allow, in certain embodiments, the recombinant bacterium to elicit both a humoral and a cellular immune response to the antigen.

Generally speaking, the bacterium comprises a chromosomally integrated nucleic acid sequence encoding a repressor and a vector. Each is discussed in more detail below.

(a) Chromosomally Integrated Nucleic Acid Sequence Encoding a Repressor

A recombinant bacterium of the invention that is capable of the regulated expression of at least one nucleic acid sequence encoding an antigen comprises, in part, at least one chromosomally integrated nucleic acid sequence encoding a repressor. Typically, the nucleic acid sequence encoding a repressor is operably linked to a regulatable promoter. The nucleic acid sequence encoding a repressor and/or the promoter may be modified from the wild-type nucleic acid sequence so as to optimize the expression level of the nucleic acid sequence encoding the repressor.

Methods of chromosomally integrating a nucleic acid sequence encoding a repressor operably-linked to a regulatable promoter are known in the art and detailed in the examples. Generally speaking, the nucleic acid sequence encoding a repressor should not be integrated into a locus that disrupts colonization of the host by the recombinant bacterium, or attenuates the bacterium.

In some embodiments, at least one nucleic acid sequence encoding a repressor is chromosomally integrated. In other embodiments, at least two, or at least three nucleic acid sequences encoding repressors may be chromosomally integrated into the recombinant bacterium. If there is more than one nucleic acid sequence encoding a repressor, each nucleic acid sequence encoding a repressor may be operably linked to a regulatable promoter, such that each promoter is regulated by the same compound or condition. Alternatively, each nucleic acid sequence encoding a repressor may be operably linked to a regulatable promoter, each of which is regulated by a different compound or condition.

i. Repressor

As used herein, "repressor" refers to a biomolecule that represses transcription from one or more promoters. Generally speaking, a suitable repressor of the invention is synthesized in high enough quantities during the in vitro growth of the bacterial strain to repress the transcription of the nucleic acid encoding an antigen of interest on the vector, as detailed below, and not impede the in vitro growth of the strain. Additionally, a suitable repressor will generally be substantially stable, i.e. not subject to proteolytic breakdown. Furthermore, a suitable repressor will be diluted by about half at every cell division after expression of the repressor ceases, such as in a non-permissive environment (e.g. an animal or human host).

The choice of a repressor depends, in part, on the species of the recombinant bacterium used. For instance, the repressor is usually not derived from the same species of bacteria as the recombinant bacterium. For instance, the repressor may be derived from *E. coli*. Alternatively, the repressor may be from a bacteriophage.

Suitable repressors are known in the art, and may include, for instance, LacI of *E. coli*, C2 encoded by bacteriophage P22, or C1 encoded by bacteriophage λ. Other suitable repressors may be repressors known to regulate the expression of a regulatable nucleic acid sequence, such as nucleic acid sequences involved in the uptake and utilization of sugars. In one embodiment, the repressor is LacI. In another embodiment, the repressor is C2. In yet another embodiment, the repressor is C1.

ii. Regulatable Promoter

The chromosomally integrated nucleic acid sequence encoding a repressor is operably linked to a regulatable promoter. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. The term "operably linked," is defined above.

The regulated promoter used herein generally allows transcription of the nucleic acid sequence encoding a repressor while in a permissive environment (i.e. in vitro growth), but ceases transcription of the nucleic acid sequence encoding a repressor while in a non-permissive environment (i.e. during growth of the bacterium in an animal or human host). For instance, the promoter may be sensitive to a physical or chemical difference between the permissive and non-permissive environment. Suitable examples of such regulatable promoters are known in the art.

In some embodiments, the promoter may be responsive to the level of arabinose in the environment. Generally speaking, arabinose may be present during the in vitro growth of a bacterium, while typically absent from host tissue. In one embodiment, the promoter is derived from an araC-$P_{BAD}$ system. The araC-$P_{BAD}$ system is a tightly regulated expression system that has been shown to work as a strong promoter induced by the addition of low levels of arabinose. The araC-araBAD promoter is a bidirectional promoter controlling expression of the araBAD nucleic acid sequences in one direction, and the araC nucleic acid sequence in the other direction. For convenience, the portion of the araC-araBAD promoter that mediates expression of the araBAD nucleic acid sequences, and which is controlled by the araC nucleic acid sequence product, is referred to herein as $P_{BAD}$. For use as described herein, a cassette with the araC nucleic acid sequence and the araC-araBAD promoter may be used. This cassette is referred to herein as araC-$P_{BAD}$. The AraC protein is both a positive and negative regulator of $P_{BAD}$. In the presence of arabinose, the AraC protein is a positive regulatory element (i.e., is an activator) that allows expression from $P_{BAD}$. In the absence of arabinose, the AraC protein represses expression from $P_{BAD}$. This can lead to a 1,200-fold difference in the level of expression from $P_{BAD}$ (i.e., is a repressor).

Other enteric bacteria contain arabinose regulatory systems homologous to the araC araBAD system from *E. coli*. For example, there is homology at the amino acid sequence level between the *E. coli* and the *S. Typhimurium* AraC proteins, and less homology at the DNA level. However, there is high specificity in the activity of the AraC proteins. For example, the *E. coli* AraC protein activates only *E. coli* $P_{BAD}$ (in the presence of arabinose) and not *S. Typhimurium* $P_{BAD}$. Thus, an arabinose-regulated promoter may be used in a recombinant bacterium that possesses a similar arabinose operon, without substantial interference between the two, if the promoter and the operon are derived from two different species of bacteria.

Generally speaking, the concentration of arabinose necessary to induce expression is typically less than about 2%. In some embodiments, the concentration is less than about 1.5%, 1%, 0.5%, 0.2%, 0.1%, or 0.05%. In other embodiments, the concentration is 0.05% or below, e.g. about 0.04%, 0.03%, 0.02%, or 0.01%. In an exemplary embodiment, the concentration is about 0.05%.

In other embodiments, the promoter may be responsive to the level of maltose in the environment. Generally speaking, maltose may be present during the in vitro growth of a bacterium, while typically absent from host tissue. The malT nucleic acid encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. Unlike the araC-$P_{BAD}$ system, malT is expressed from a promoter ($P_T$) functionally unconnected to the other mal promoters. $P_T$ is not regulated by MalT. The malEFG-malKBM promoter is a bidirectional promoter controlling expression of the malKBM nucleic acid sequences in one direction, and the malEFG nucleic acid sequences in the other direction. For convenience, the portion of the malEFG-malKBM promoter that mediates expression of the malKBM nucleic acid sequence, and which is controlled by the malT nucleic acid sequence product, is referred to herein as $P_{KBM}$, and the portion of the malEFG-malKBM promoter that mediates expression of the malEFG nucleic acid sequence, and that is controlled by the malT nucleic acid sequence product, is referred to herein as $P_{EFG}$. Full induction of $P_{KBM}$ requires the presence of the MalT binding sites of $P_{EFG}$. For use in the vectors and systems described herein, a cassette with the malT nucleic acid sequence and one of the mal promoters may be used. This cassette is referred to herein as malT-$P_{mal}$. In the presence of maltose, the MalT protein is a positive regulatory element that allows expression from $P_{mal}$.

In still other embodiments, the promoter may be sensitive to the level of rhamnose in the environment. Analogous to the araC-$P_{BAD}$ system described above, the rhaRS-$P_{rhaB}$ activator-promoter system is tightly regulated by rhamnose. Expression from the rhamnose promoter ($P_{rha}$) is induced to high levels by the addition of rhamnose, which is common in bacteria but rarely found in host tissues. The nucleic acid sequences rhaBAD are organized in one operon that is controlled by the $P_{rhaBAD}$ promoter. This promoter is regulated by two activators, RhaS and RhaR, and the corresponding nucleic acid sequences belong to one transcription unit that is located in the opposite direction of the rhaBAD nucleic acid sequences. If L-rhamnose is available, RhaR binds to the $P_{rhaRS}$ promoter and activates the production of RhaR and RhaS. RhaS together with L-rhamnose in turn binds to the $P_{rhaBAD}$ and the $P_{rhaT}$ promoter and activates the transcription of the structural nucleic acid sequences. Full induction of rhaBAD transcription also requires binding of the Crp-cAMP complex, which is a key regulator of catabolite repression.

Although both L-arabinose and L-rhamnose act directly as inducers for expression of regulons for their catabolism, important differences exist in regard to the regulatory mechanisms. L-Arabinose acts as an inducer with the activator AraC in the positive control of the arabinose regulon. However, the L-rhamnose regulon is subject to a regulatory cascade; it is therefore subject to even tighter control than the araC $P_{BAD}$ system. L-Rhamnose acts as an inducer with the activator RhaR for synthesis of RhaS, which in turn acts as an activator in the positive control of the rhamnose regulon. In the present invention, rhamnose may be used to interact with the RhaR protein and then the RhaS protein may activate transcription of a nucleic acid sequence operably-linked to the $P_{rhaBAD}$ promoter.

In still other embodiments, the promoter may be sensitive to the level of xylose in the environment. The xylR-$P_{xylA}$ system is another well-established inducible activator-promoter system. Xylose induces xylose-specific operons (xylE, xylFGHR, and xylAB) regulated by XylR and the cyclic AMP-Crp system. The XylR protein serves as a positive regulator by binding to two distinct regions of the xyl nucleic acid sequence promoters. As with the araC-$P_{BAD}$ system described above, the xylR-$P_{xylAB}$ and/or xylR-$P_{xylFGH}$ regulatory systems may be used in the present invention. In these embodiments, xylR $P_{xylAB}$ xylose interacting with the XylR protein activates transcription of nucleic acid sequences operably-linked to either of the two $P_{xyl}$ promoters.

The nucleic acid sequences of the promoters detailed herein are known in the art, and methods of operably-linking them to a chromosomally integrated nucleic acid sequence encoding a repressor are known in the art and detailed in the examples.

iii. Modification to Optimize Expression

A nucleic acid sequence encoding a repressor and regulatable promoter detailed above, for use in the present invention, may be modified so as to optimize the expression level of the nucleic acid sequence encoding the repressor. The optimal level of expression of the nucleic acid sequence encoding the repressor may be estimated, or may be determined by experimentation (see the Examples). Such a determination should take into consideration whether the repressor acts as a monomer, dimer, trimer, tetramer, or higher multiple, and should also take into consideration the copy number of the vector encoding the antigen of interest, as detailed below. In an exemplary embodiment, the level of expression is optimized so that the repressor is synthesized while in the permissive environment (i.e. in vitro growth) at a level that substantially inhibits the expression of the nucleic acid encoding an antigen of interest, and is substantially not synthesized in a non-permissive environment, thereby allowing expression of the nucleic acid encoding an antigen of interest.

As stated above, the level of expression may be optimized by modifying the nucleic acid sequence encoding the activator, repressor and/or promoter. As used herein, "modify" refers to an alteration of the nucleic acid sequence of the repressor and/or promoter that results in a change in the level of transcription of the nucleic acid sequence encoding the repressor, or that results in a change in the level of synthesis of the repressor. For instance, in one embodiment, modify may refer to altering the start codon of the nucleic acid sequence encoding the repressor. Generally speaking, a GTG or TTG start codon, as opposed to an ATG start codon, may decrease translation efficiency ten-fold. In another embodiment, modify may refer to altering the Shine-Dalgarno (SD) sequence of the nucleic acid sequence encoding the repressor. The SD sequence is a ribosomal binding site generally located 6-7 nucleotides upstream of the start codon. The SD consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence encoding the repressor to alter the level of translation of the mRNA encoding the repressor. For instance, non-A rich codons initially after the start codon of the nucleic acid sequence encoding the repressor may not maximize translation of the mRNA encoding the repressor. Similarly, the codons of the nucleic acid sequence encoding the repressor may be altered so as to mimic the codons from highly synthesized proteins of a particular organism. In a further embodiment, modify may refer to altering the GC content of the nucleic acid sequence encoding the repressor to change the level of translation of the mRNA encoding the repressor.

In some embodiments, more than one modification or type of modification may be performed to optimize the expression level of the nucleic acid sequence encoding the repressor. For instance, at least one, two, three, four, five, six, seven, eight, or nine modifications, or types of modifications, may be performed to optimize the expression level of the nucleic acid sequence encoding the repressor.

Methods of modifying the nucleic acid sequence encoding the repressor and/or the regulatable promoter are known in the art and detailed in the examples.

iv. Transcription Termination Sequence

In some embodiments, the chromosomally integrated nucleic acid sequence encoding the repressor further comprises a transcription termination sequence. A transcription termination sequence may be included to prevent inappropriate expression of nucleic acid sequences adjacent to the chromosomally integrated nucleic acid sequence encoding the repressor or activator and regulatable promoter.

(b) Vector

A recombinant bacterium of the invention that is capable of the regulated expression of at least one nucleic acid sequence encoding an antigen comprises, in part, a vector. The vector comprises a nucleic acid sequence encoding at least one antigen of interest operably linked to a promoter. The promoter is regulated by the chromosomally encoded repressor, such that the expression of the nucleic acid sequence encoding an antigen is repressed during in vitro growth of the bacterium, but the bacterium is capable of high level synthesis of the antigen in an animal or human host.

As used herein, "vector" refers to an autonomously replicating nucleic acid unit. The present invention can be practiced with any known type of vector, including viral, cosmid, phasmid, and plasmid vectors. The most preferred type of vector is a plasmid vector.

As is well known in the art, plasmids and other vectors may possess a wide array of promoters, multiple cloning sequences, transcription terminators, etc., and vectors may be selected so as to control the level of expression of the nucleic acid sequence encoding an antigen by controlling the relative copy number of the vector. In some instances in which the vector might encode a surface localized adhesin as the antigen, or an antigen capable of stimulating T-cell immunity, it may be preferable to use a vector with a low copy number such as at least two, three, four, five, six, seven, eight, nine, or ten copies per bacterial cell. A non-limiting example of a low copy number vector may be a vector comprising the pSC101 ori.

In other cases, an intermediate copy number vector might be optimal for inducing desired immune responses. For instance, an intermediate copy number vector may have at least 10, 11, 12, 13, 14, 15, 16, 17, 18, 19, 20, 21, 22, 23, 24, 25, 26, 27, 28, 29, or 30 copies per bacterial cell. A non-limiting example of an intermediate copy number vector may be a vector comprising the p15A ori.

In still other cases, a high copy number vector might be optimal for the induction of maximal antibody responses. A high copy number vector may have at least 31, 35, 40, 45, 50, 55, 60, 65, 70, 75, 80, 85, 90, 95, or 100 copies per bacterial cell. In some embodiments, a high copy number vector may have at least 100, 125, 150, 175, 200, 225, 250, 275, 300, 325, 350, 375, or 400 copies per bacterial cell. Non-limiting examples of high copy number vectors may include a vector comprising the pBR ori or the pUC ori.

Additionally, vector copy number may be increased by selecting for mutations that increase plasmid copy number. These mutations may occur in the bacterial chromosome but are more likely to occur in the plasmid vector.

Preferably, vectors used herein do not comprise antibiotic resistance markers to select for maintenance of the vector.

i. Antigen

As used herein, "antigen" refers to a biomolecule capable of eliciting an immune response in a host. In some embodiments, an antigen may be a protein, or fragment of a protein, or a nucleic acid. In an exemplary embodiment, the antigen elicits a protective immune response. As used herein, "protective" means that the immune response contributes to the lessening of any symptoms associated with infection of a host with the pathogen the antigen was derived from or designed to elicit a response against. For example, a protective antigen from a pathogen, such as *Mycobacterium*, may induce an immune response that helps to ameliorate symptoms associated with *Mycobacterium* infection or reduce the morbidity and mortality associated with infection with the pathogen. The use of the term "protective" in this invention does not necessarily require that the host is completely protected from the effects of the pathogen.

Antigens may be from bacterial, viral, mycotic and parasitic pathogens, and may be designed to protect against bacterial, viral, mycotic, and parasitic infections, respectively. Alternatively, antigens may be derived from gametes, provided they are gamete specific, and may be designed to block fertilization. In another alternative, antigens may be tumor antigens, and may be designed to decrease tumor growth. It is specifically contemplated that antigens from organisms newly identified or newly associated with a disease or pathogenic condition, or new or emerging pathogens of animals or humans, including those now known or identified in the future, may be expressed by a bacterium detailed herein. Furthermore, antigens for use in the invention are not limited to those from pathogenic organisms. Immunogenicity of the bacterium may be augmented and/or modulated by constructing strains that also express sequences for cytokines, adjuvants, and other immunomodulators.

Some examples of microorganisms useful as a source for antigen are listed below. These may include microoganisms for the control of plague caused by *Yersinia pestis* and other *Yersinia* species such as *Y. pseudotuberculosis* and *Y. enterocolitica*, for the control of gonorrhea caused by *Neisseria gonorrhoea*, for the control of syphilis caused by *Treponema pallidum*, and for the control of venereal diseases as well as eye infections caused by *Chlamydia trachomatis*. Species of *Streptococcus* from both group A and group B, such as those species that cause sore throat or heart diseases, *Erysipelothrix rhusiopathiae, Neisseria meningitidis, Mycoplasma pneumoniae* and other *Mycoplasma*-species, *Hemophilus influenza, Bordetella pertussis, Mycobacterium tuberculosis, Mycobacterium leprae*, other *Bordetella* species, *Escherichia coli, Streptococcus equi, Streptococcus pneumoniae, Brucella abortus, Pasteurella hemolytica* and *P. multocida, Vibrio cholera, Shigella* species, *Borrellia* species, *Bartonella* species, *Heliobacter pylori, Campylobacter* species, *Pseudomonas* species, *Moraxella* species, *Brucella* species, *Francisella* species, *Aeromonas* species, *Actinobacillus* species, *Clostridium* species, *Rickettsia* species, *Bacillus* species, *Coxiella* species, *Ehrlichia* species, *Listeria* species, and *Legionella pneumophila* are additional examples of bacteria within the scope of this invention from which antigen nucleic acid sequences could be obtained. Viral antigens may also be used. Viral antigens may be used in antigen delivery microorganisms directed against viruses, either DNA or RNA viruses, for example from the classes Papovavirus, Adenovirus, Herpesvirus, Poxvirus, Parvovirus, Reovirus, Picornavirus, Myxovirus, Paramyxovirus, Flavivirus or Retrovirus. Antigens may also be derived from pathogenic fungi, protozoa and parasites.

Certain embodiments encompass an allergen as an antigen. Allergens are substances that cause allergic reactions in a host that is exposed to them. Allergic reactions, also known as Type I hypersensitivity or immediate hypersensitivity, are vertebrate immune responses characterized by IgE production in conjunction with certain cellular immune reactions. Many different materials may be allergens, such as animal dander and pollen, and the allergic reaction of individual hosts will vary for any particular allergen. It is possible to induce tolerance to an allergen in a host that normally shows an allergic response. The methods of inducing tolerance are well-known and generally comprise administering the allergen to the host in increasing dosages.

It is not necessary that the vector comprise the complete nucleic acid sequence of the antigen. It is only necessary that the antigen sequence used be capable of eliciting an immune response. The antigen may be one that was not found in that exact form in the parent organism. For example, a sequence coding for an antigen comprising 100 amino acid residues may be transferred in part into a recombinant bacterium so that a peptide comprising only 75, 65, 55, 45, 35, 25, 15, or even 10, amino acid residues is produced by the recombinant bacterium. Alternatively, if the amino acid sequence of a particular antigen or fragment thereof is known, it may be possible to chemically synthesize the nucleic acid fragment or analog thereof by means of automated nucleic acid sequence synthesizers, PCR, or the like and introduce said nucleic acid sequence into the appropriate copy number vector.

In another alternative, a vector may comprise a long sequence of nucleic acid encoding several nucleic acid sequence products, one or all of which may be antigenic. In some embodiments, a vector of the invention may comprise a nucleic acid sequence encoding at least one antigen, at least two antigens, at least three antigens, or more than three antigens. These antigens may be encoded by two or more open reading frames operably linked to be expressed coordinately as an operon, wherein each antigen is synthesized independently. Alternatively, the two or more antigens may be encoded by a single open reading frame such that the antigens are synthesized as a fusion protein.

In certain embodiments, an antigen of the invention may comprise a B cell epitope or a T cell epitope. Alternatively, an antigen to which an immune response is desired may be expressed as a fusion to a carrier protein that contains a strong promiscuous T cell epitope and/or serves as an adjuvant and/or facilitates presentation of the antigen to enhance, in all cases, the immune response to the antigen or its component part. This can be accomplished by methods known in the art. Fusion to tenus toxin fragment C, CT-B, LT-B and hepatitis virus B core are particularly useful for these purposes, although other epitope presentation systems are well known in the art.

In further embodiments, a nucleic acid sequence encoding an antigen of the invention may comprise a secretion signal. In other embodiments, an antigen of the invention may be toxic to the recombinant bacterium.

A suitable antigen derived from *Yersinia*, and designed to induce an immune response against *Yersinia* may include LcrV, Psn, PsaA, and Pla.

ii. Promoter Regulated by Repressor

The vector comprises a nucleic acid sequence encoding at least one antigen operably-linked to a promoter regulated by the repressor, encoded by a chromosomally integrated nucleic acid sequence. One of skill in the art would recognize, therefore, that the selection of a repressor dictates, in part, the selection of the promoter operably-linked to a nucleic acid sequence encoding an antigen of interest. For instance, if the repressor is LacI, then the promoter may be selected from the group consisting of LacI responsive promoters, such as $P_{trc}$, $P_{lac}$, $P_{T7lac}$ and $P_{tac}$. If the repressor is C2, then the promoter may be selected from the group consisting of C2 responsive promoters, such as P22 promoters $P_L$ and $P_R$. If the repressor is C1, then the promoter may be selected from the group consisting of C1 responsive promoters, such as X promoters $P_L$ and $P_R$.

In each embodiment herein, the promoter regulates expression of a nucleic acid sequence encoding the antigen, such that expression of the nucleic acid sequence encoding an antigen is repressed when the repressor is synthesized (i.e. during in vitro growth of the bacterium), but expression of the nucleic acid sequence encoding an antigen is high when the repressor is not synthesized (i.e. in an animal or human host). Generally speaking, the concentration of the repressor will decrease with every cell division after expression of the nucleic acid sequence encoding the repressor ceases. In some embodiments, the concentration of the repressor decreases enough to allow high-level expression of the nucleic acid sequence encoding an antigen after about 2, 3, 4, 5, 6, 7, 8, 9, 10, 11, or 12 divisions of the bacterium. In an exemplary embodiment, the concentration of the repressor decreases enough to allow high level expression of the nucleic acid sequence encoding an antigen after about 5 divisions of the bacterium in an animal or human host.

In certain embodiments, the promoter may comprise other regulatory elements. For instance, the promoter may comprise lacO if the repressor is LacI. This is the case with the lipoprotein promoter $P_{lpp}$ that is regulated by LacI since it possesses the LacI binding domain lacO.

In one embodiment, the repressor is a LacI repressor and the promoter is $P_{trc}$.

iii. Expression of the Nucleic Acid Sequence Encoding an Antigen

As detailed above, generally speaking the expression of the nucleic acid sequence encoding the antigen should be repressed when the repressor is synthesized. For instance, if the repressor is synthesized during in vitro growth of the bacterium, expression of the nucleic acid sequence encoding the antigen should be repressed. Expression may be "repressed" or "partially repressed" when it is about 50%, 45%, 40%, 35%, 30%, 25%, 20%, 15%, 10%, 5%, 1%, or even less than 1% of the expression under non-repressed conditions. Thus although the level of expression under conditions of "complete repression" might be exceeding low, it is likely to be detectable using very sensitive methods since repression can never by absolute.

Conversely, the expression of the nucleic acid sequence encoding the antigen should be high when the expression of the nucleic acid sequence encoding the repressor is repressed. For instance, if the nucleic acid sequence encoding the repressor is not expressed during growth of the recombinant bacterium in the host, the expression of the nucleic acid sequence encoding the antigen should be high. As used herein, "high level" expression refers to expression that is strong enough to elicit an immune response to the antigen. Consequently, the copy number correlating with high level expression can and will vary depending on the antigen and the type of immune response desired. Methods of determining whether an antigen elicits an immune response such as by measuring antibody levels or antigen-dependant T cell populations or antigen-dependant cytokine levels are known in the art, and methods of measuring levels of expression of antigen encoding sequences by measuring levels of mRNA transcribed or by quantitating the level of antigen synthesis are also known in the art. For more details, see the examples.

(c) Crp Cassette

In some embodiments, a recombinant bacterium of the invention may also comprise a $\Delta P_{crp}$::TT araC $P_{BAD}$ crp deletion-insertion mutation. Since the araC $P_{BAD}$ cassette is dependent both on the presence of arabinose and the binding of the catabolite repressor protein Crp, a $\Delta P_{crp}$::TT araC $P_{BAD}$ crp deletion-insertion mutation may be included as an additional means to reduce expression of any nucleic acid sequence under the control of the $P_{BAD}$ promoter. This means that when the bacterium is grown in a non-permissive environment (i.e. no arabinose) both the repressor itself and the Crp protein cease to be synthesized, consequently eliminating both regulating signals for the araC $P_{BAD}$ regulated nucleic acid sequence. This double shut off of araC $P_{BAD}$ may constitute an additional safety feature ensuring the genetic stability of the desired phenotypes.

Generally speaking, the activity of the Crp protein requires interaction with cAMP, but the addition of glucose, which may inhibit synthesis of cAMP, decreases the ability of the Crp protein to regulate transcription from the araC $P_{BAD}$ promoter. Consequently, to avoid the effect of glucose on cAMP, glucose may be substantially excluded from the growth media, or variants of crp may be isolated that synthesize a Crp protein that is not dependent on cAMP to regulate transcription from $P_{BAD}$. This strategy may also be used in other systems responsive to Crp, such as the systems responsive to rhamnose and xylose described above.

III. Vaccine Compositions and Administration

A recombinant bacterium of the invention may be administered to a host as a vaccine composition. As used herein, a vaccine composition may be a composition designed to elicit an immune response against *Yersinia*. Additionally, a vaccine composition may be a composition designed to elicit an immune response against *Yersinia* and against one or more additional pathogens. In an exemplary embodiment, the immune response is protective, as described above. In one exemplary embodiment, the immune response is protective against both pneumonic and bubonic plague. Immune responses to antigens are well studied and widely reported. A survey of immunology is given by Paul, W E, Stites D et. al. and Ogra P L. et. al. Mucosal immunity is also described by Ogra P L et. al.

Vaccine compositions of the present invention may be administered to any host capable of mounting an immune response. Such hosts may include all vertebrates, for example, mammals, including domestic animals, agricultural animals, laboratory animals, and humans. Preferably, the host is a warm-blooded animal. The vaccine can be administered as a prophylactic, for treatment purposes, or for possible elimination of *Y. pestis* persistence in wild-animals.

In exemplary embodiments, the recombinant bacterium is alive when administered to a host in a vaccine composition of the invention. Suitable vaccine composition formulations and methods of administration are detailed below.

(a) Vaccine Composition

A vaccine composition comprising a recombinant bacterium of the invention may optionally comprise one or more possible additives, such as carriers, preservatives, stabilizers, adjuvants, and other substances.

In one embodiment, the vaccine comprises an adjuvant. Adjuvants, such as aluminum hydroxide or aluminum phosphate, are optionally added to increase the ability of the vaccine to trigger, enhance, or prolong an immune response.

In exemplary embodiments, the use of a live attenuated recombinant bacterium may act as a natural adjuvant. The vaccine compositions may further comprise additional components known in the art to improve the immune response to a vaccine, such as T cell co-stimulatory molecules or antibodies, such as anti-CTLA4. Additional materials, such as cytokines, chemokines, and bacterial nucleic acid sequences naturally found in bacteria, like CpG, are also potential vaccine adjuvants.

In another embodiment, the vaccine may comprise a pharmaceutical carrier (or excipient). Such a carrier may be any solvent or solid material for encapsulation that is non-toxic to the inoculated host and compatible with the recombinant bacterium. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995). When used for administering via the bronchial tubes, the vaccine is preferably presented in the form of an aerosol.

Care should be taken when using additives so that the live recombinant bacterium is not killed, or have its ability to effectively colonize the host compromised by the use of additives. Stabilizers, such as lactose or monosodium glutamate (MSG), may be added to stabilize the vaccine formulation against a variety of conditions, such as temperature variations or a freeze-drying process.

The dosages of a vaccine composition of the invention can and will vary depending on the recombinant bacterium, the regulated antigen, and the intended host, as will be appreciated by one of skill in the art. Generally speaking, the dosage need only be sufficient to elicit a protective immune response in a majority of hosts. Routine experimentation may readily establish the required dosage. Typical initial dosages of vaccine for oral administration could be about $1 \times 10^7$ to $1 \times 10^{10}$ CFU depending upon the age of the host to be immunized. Administering multiple dosages may also be used as needed to provide the desired level of protective immunity.

(b) Methods of Administration

A vaccine of the invention may be administered via any suitable route, such as by oral administration, intranasal administration, gastric intubation or in the form of aerosols. Additionally, other methods of administering the recombinant bacterium, such as intravenous, intramuscular, subcutaneous injection or other parenteral routes, are possible.

In some embodiments, these compositions are formulated for administration by injection (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like.

IV. Kits

The invention also encompasses kits comprising any one of the compositions above in a suitable aliquot for vaccinating a host in need thereof. In one embodiment, the kit further comprises instructions for use. In other embodiments, the composition is lyophilized such that addition of a hydrating agent (e.g., buffered saline) reconstitutes the composition to generate a vaccine composition ready to administer, preferably orally.

V. Methods of Use

A further aspect of the invention encompasses methods of using a recombinant bacterium of the invention. For instance, in one embodiment the invention provides a method for modulating a host's immune system. The method comprises administering to the host an effective amount of a composition comprising a recombinant bacterium of the invention. One of skill in the art will appreciate that an effective amount of a composition is an amount that will generate the desired immune response (e.g., mucosal, humoral or cellular). Methods of monitoring a host's immune response are well-known to physicians and other skilled practitioners. For instance, assays such as ELISA, and ELISPOT may be used. Effectiveness may be determined by monitoring the amount of the antigen of interest remaining in the host, or by measuring a decrease in disease incidence caused by *Yersinia* and/or another pathogen in a host. For certain pathogens, cultures or swabs taken as biological samples from a host may be used to monitor the existence or amount of pathogen in the individual.

In another embodiment, the invention provides a method for eliciting an immune response against *Yersinia* in a host. The method comprises administering to the host an effective amount of a composition comprising a recombinant bacterium of the invention In still another embodiment, a recombinant bacterium of the invention may be used in a method for eliciting an immune response against *Yersinia* and one or more additional pathogens in an individual in need thereof. The method comprises administrating to the host an effective amount of a composition comprising a recombinant bacterium as described herein.

In a further embodiment, a recombinant bacterium described herein may be used in a method for ameliorating one or more symptoms of bubonic or pneumonic plague in a host in need thereof. The method comprises administering an effective amount of a composition comprising a recombinant bacterium as described herein.

EXAMPLES

The following examples illustrate various iterations of the invention.

Introduction for Examples 1-7

The Examples below determine what role relA and spoT play in *Y. pestis* physiology and virulence by constructing ΔrelA and ΔrelA ΔspoT mutants and characterizing them for both in vitro and in vivo characteristics. We examined the effect of these mutations on transcription and protein levels at 26° C. (flea temperature) and at 37° C. (human temperature) and the effect on host colonization, immune responses and virulence. We also evaluated the double mutant for its capacity to induce protective immunity.

Example 1

Sequence Analysis of the RelA and SpoT Genes

Analysis of the *Y. pestis* KIM5+ database revealed the presence of relA and spoT genes homologous to *E. coli* K-12 and *S. Typhimurium* LT-2 [15, 16, 17]. The *Y. pestis* RelA protein shares 84.7% identity with *E. coli* K-12 and 83.9% identity with *S. Typhimurium* LT-2 RelA proteins. The *Y. pestis* SpoT protein has 91.3% identity with *E. coli* K-12 and 91.8% identity with *S. Typhimurium* LT-2 SpoT proteins.

Our analysis indicated that *Y. pestis* SpoT, but not RelA, possesses the HD domain that is conserved in a superfamily of metal-dependent phosphohydrolases [18]. Histidine (H) and aspartate (D) residues in the HD domain are thought to be involved in (p)ppGpp degradation [18]. Both *Y. pestis* RelA and SpoT proteins possess the conserved ATP/GTP-binding and GTP binding domains, TGS [19] and ACT [20,21], respectively, that are present in the *E. coli* RelA and SpoT proteins [22]. The presence of these conserved motifs in the *Y. pestis* proteins is in agreement with their biochemical functions because ATP and GTP are substrates of the reaction catalyzed by (p)ppGpp synthetase.

Example 2

The RelA and SpoT Genes are Involved in Synthesis of ppGpp and Physiological Differentiation To evaluate the linkage between relA and spoT and the production of ppGpp, we constructed ΔrelA, ΔrelA ΔspoT [5] and ΔrelA ΔspoT ΔlacZ::TT araC $P_{BAD}$ spoT mutants of *Y. pestis* KIM6+ strain (FIG. 1). To construct a strain with arabinose-regulated spoT expression, a TT araC $P_{BAD}$ promoter cassette was inserted in front of the spoT gene. The spoT gene is located in the middle of an operon. To avoid affecting the transcription of nearby genes, the TT araC $P_{BA}$D spoT construct was inserted at another location, lacZ (FIG. 1).

Because of the high degree of similarity between *Y. pestis* RelA and SpoT proteins and their *E. coli* and *Salmonella* counterparts, it is likely that the function of RelA and SpoT in *Y. pestis* will be the same. To evaluate the effect of relA and spoT on ppGpp synthesis during amino acid starvation, *Y. pestis* was grown in PHM2 media [2] without L-phenylalanine. ppGpp accumulation was observed in wild-type *Y. pestis,* but not in the relA null strains (FIG. 2A), illustrating that *Y. pestis* is indeed capable of ppGpp biosynthesis in response to amino acid starvation. We also evaluated the effect of carbon starvation. When glucose was exhausted in the medium, ppGpp accumulated in the wild type and ΔrelA spoT+ strains, but not in ΔrelA ΔspoT strains (FIG. 2B). These results indicate that *Y. pestis* has a RelA-dependent response to amino acid starvation and a SpoT-dependent response to glucose starvation, comparable to what is observed in *E. coli* [23]. The SpoT deficiency could be complemented in strain χ10019 (ΔrelA233 ΔspoT85 ΔlacZ516::TT araC $P_{BAD}$ spoT) by the addition of arabinose. Synthesis of SpoT in strain χ10019 in the presence of 0.05% arabinose was nearly identical to wild-type SpoT synthesis (FIGS. 3 and 4). The addition of arabinose to strain χ10019 also restored ppGpp synthesis when cells were starved for carbon (FIG. 2B).

A cursory examination of the *Y. pestis* ΔrelA ΔspoT double mutant after growth on solid rich medium indicated that the ΔrelA ΔspoT double mutants grew more slowly than wild-type or ΔrelA mutants. When growth was assessed in liquid medium, the ΔrelA ΔspoT mutants exhibited a longer lag phase and did not reach as high a final $OD_{600}$ than the wild-type and ΔrelA mutant strains at both 26° C. and 37° C. (FIGS. 5A and B). The ΔrelA ΔspoT strains were prone to autoaggregate and precipitate to the bottom of the culture tube at 26° C., but not at 37° C. The addition of 0.05% arabinose restored wild-type growth characteristics to strain χ10019 (ΔrelA233 ΔspoT85 ΔlacZ516::TT araC $P_{BAD}$ spoT) (FIG. 5), but it continued to autoaggregate and precipitate at 26° C. However, the addition of higher concentrations of arabinose reduced autoaggregation in a concentration-dependent manner. The addition of 0.4% arabinose resulted in the complete absence of detectable autoaggregation at 26° C.

Example 3

The Effect of ppGpp on Production of Virulence Factors of *Y. pestis*

Figure 1:
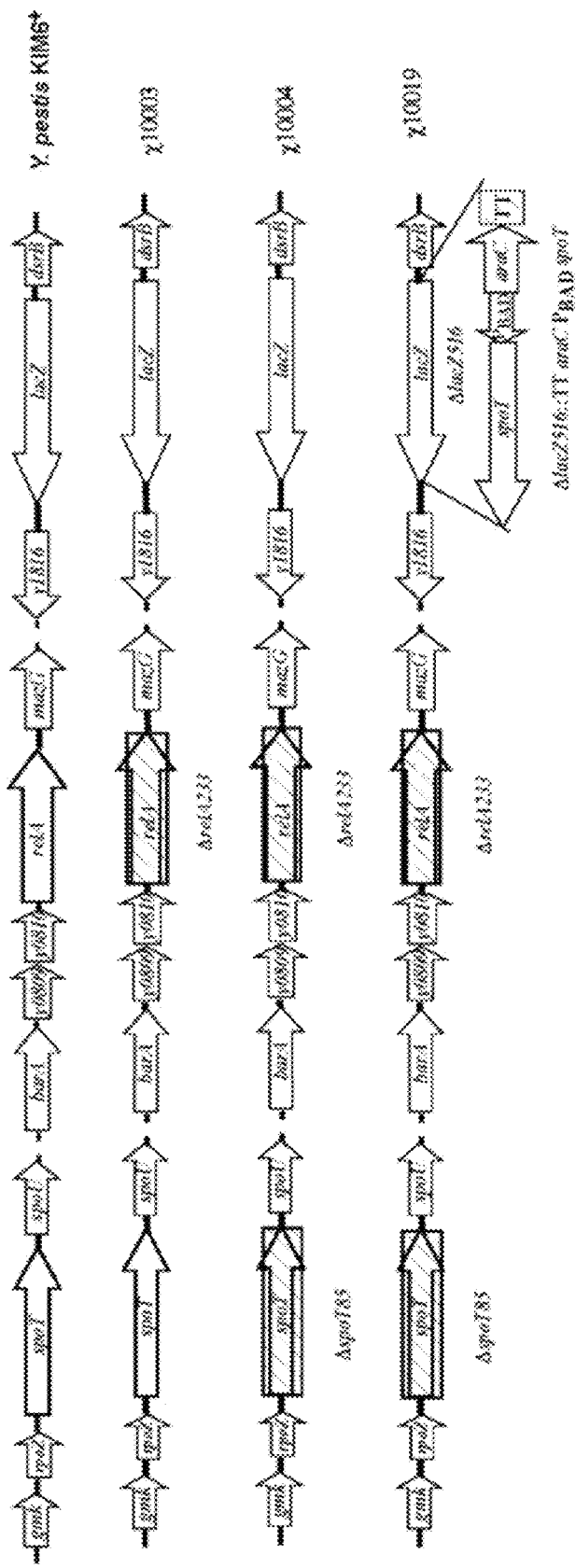
Figure 2A:
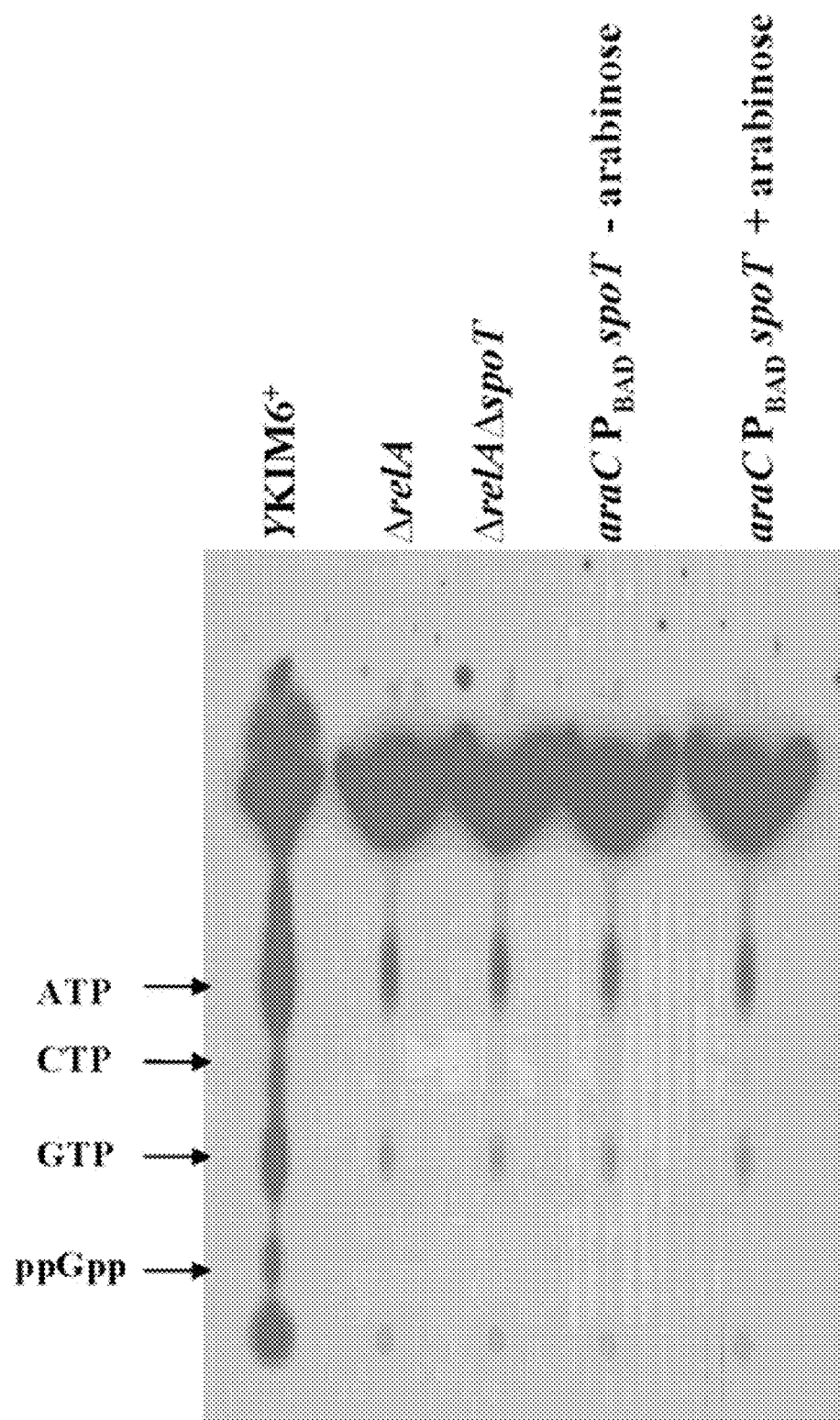
Figure 2B:
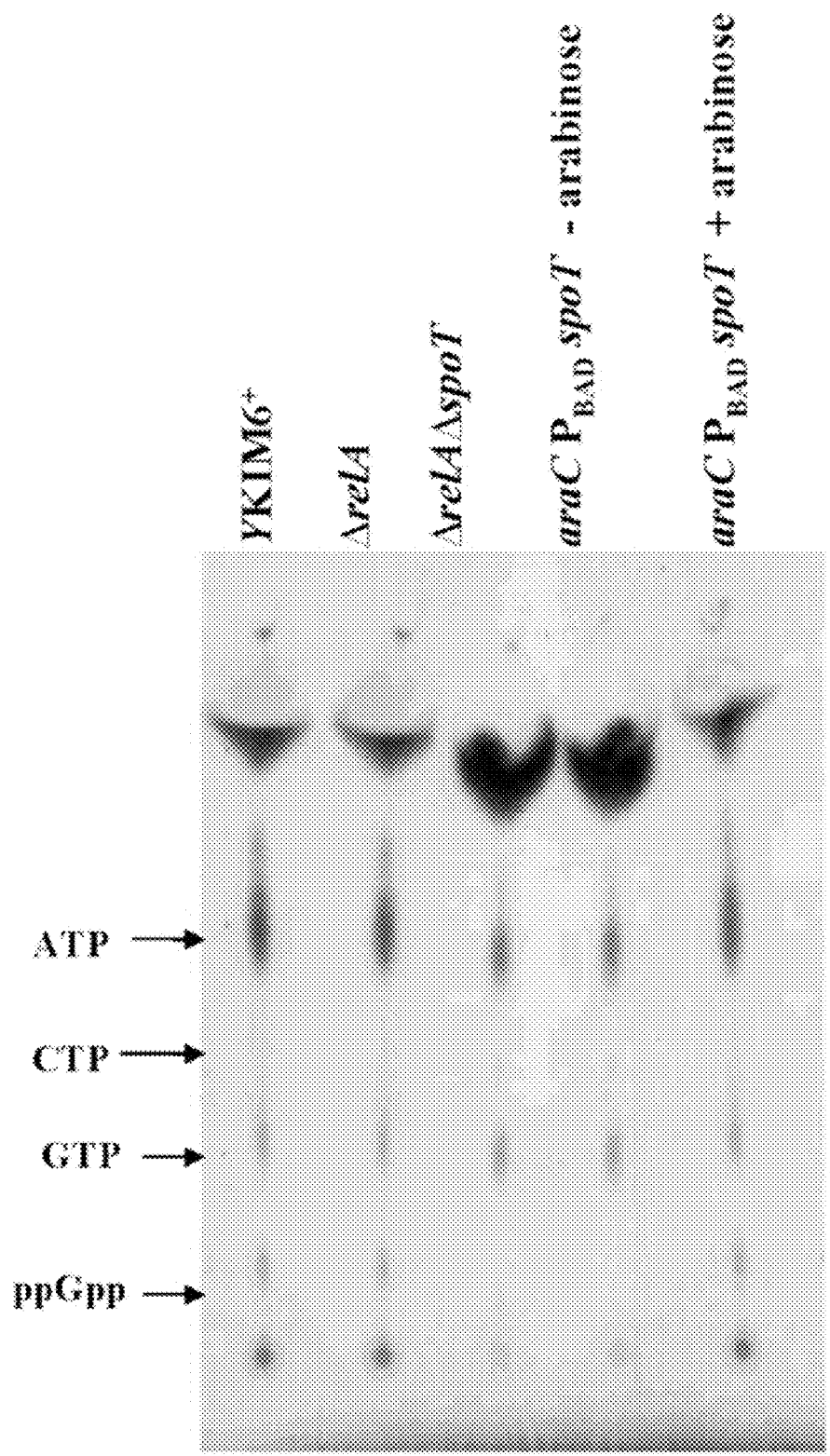
Figure 3:
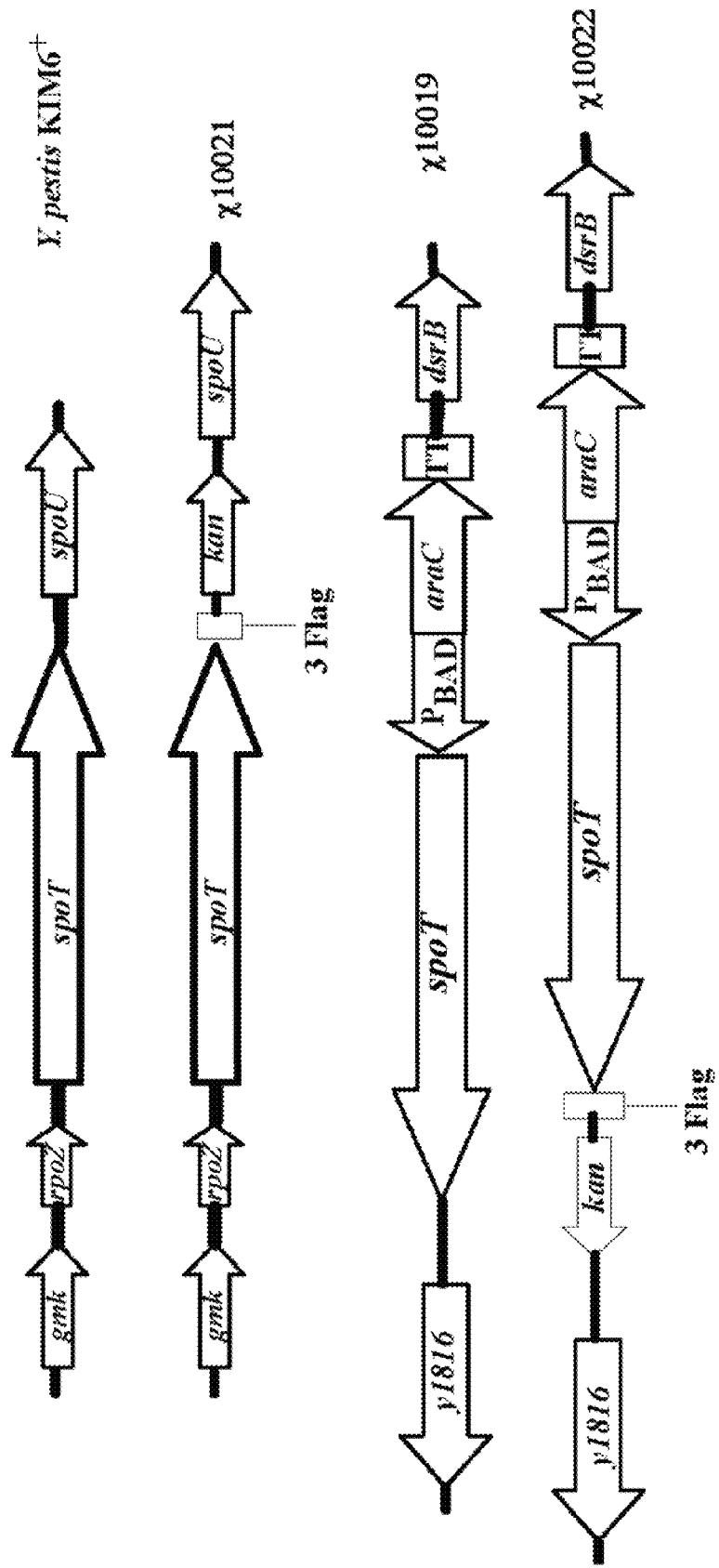
Figure 4:
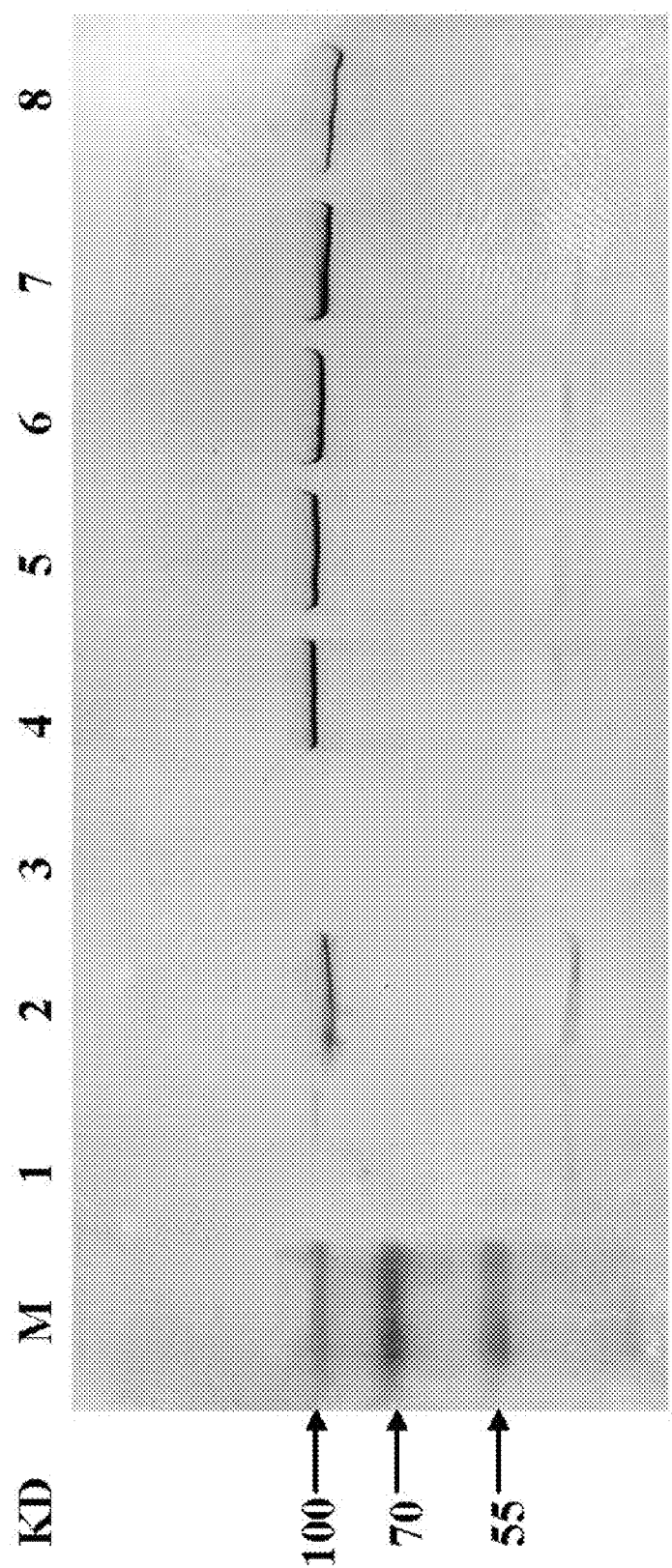
Figure 5:
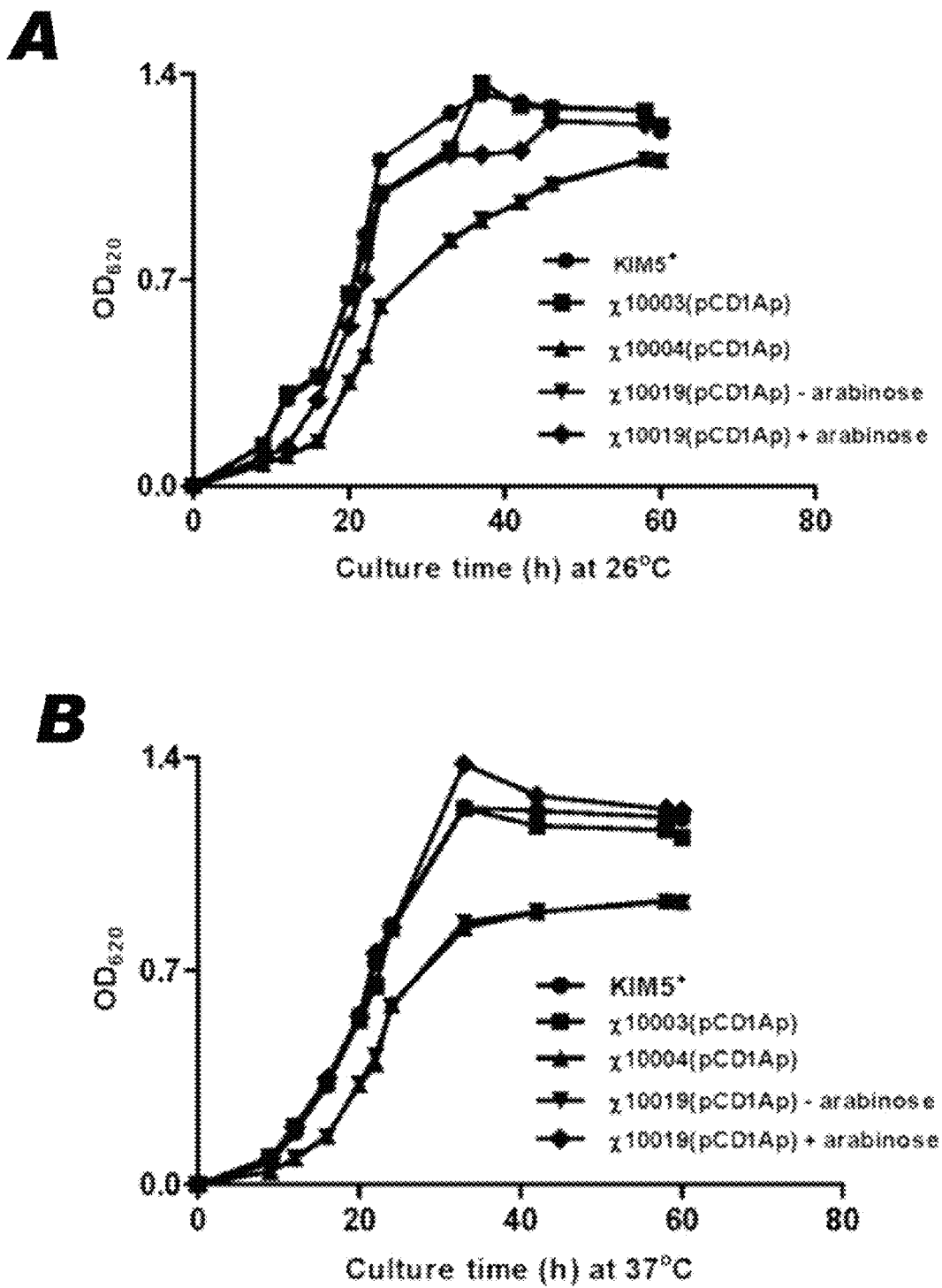
Figure 6A:
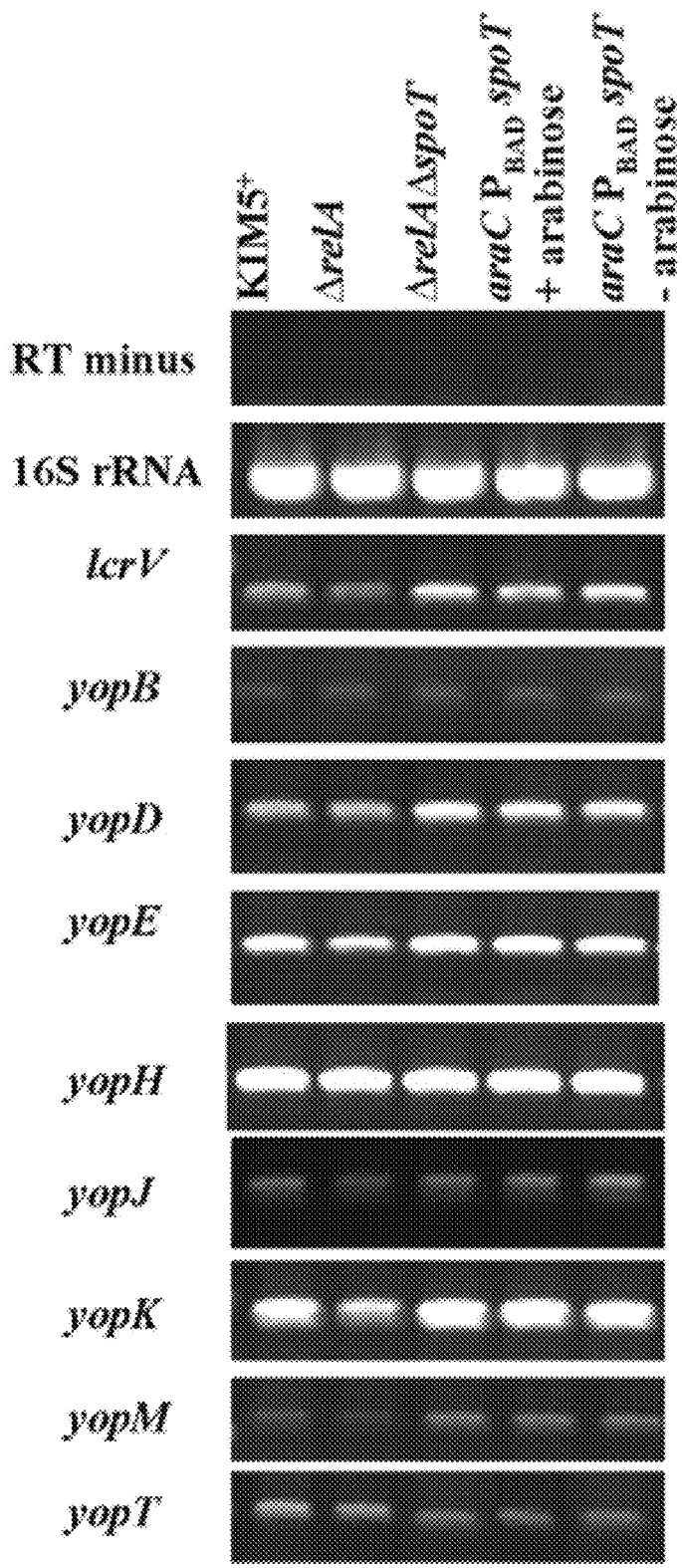

The virulence of the pathogenic *Yersinia* species depends on a plasmid-encoded type III secretion system (T3SS) that transfers effector proteins called Yops (*Yersinia* outer proteins) into host cells, interfering with mammalian cell signaling pathways, inhibiting phagocytosis, modulating cytokine production, and inducing apoptosis [24]. In *S. Typhimurium*, pathogenicity islands 1 and 2 (SPI1 and SPI2) encode T3SSs required for invasion and replication within host cells, respectively [25]. SPI1 and SPI2 gene transcription and expression are severely reduced in the absence of ppGpp [26]. To determine if ppGpp had a similar effect on *Y. pestis*, transcription of the genes encoding T3SS substrates LcrV and Yop proteins was analyzed using RT-PCR. Our results indicated that relA or relA spoT status did not have a significant effect on the transcription of lcrV and or the yop genes (FIG. 6A).

Figure 7A:
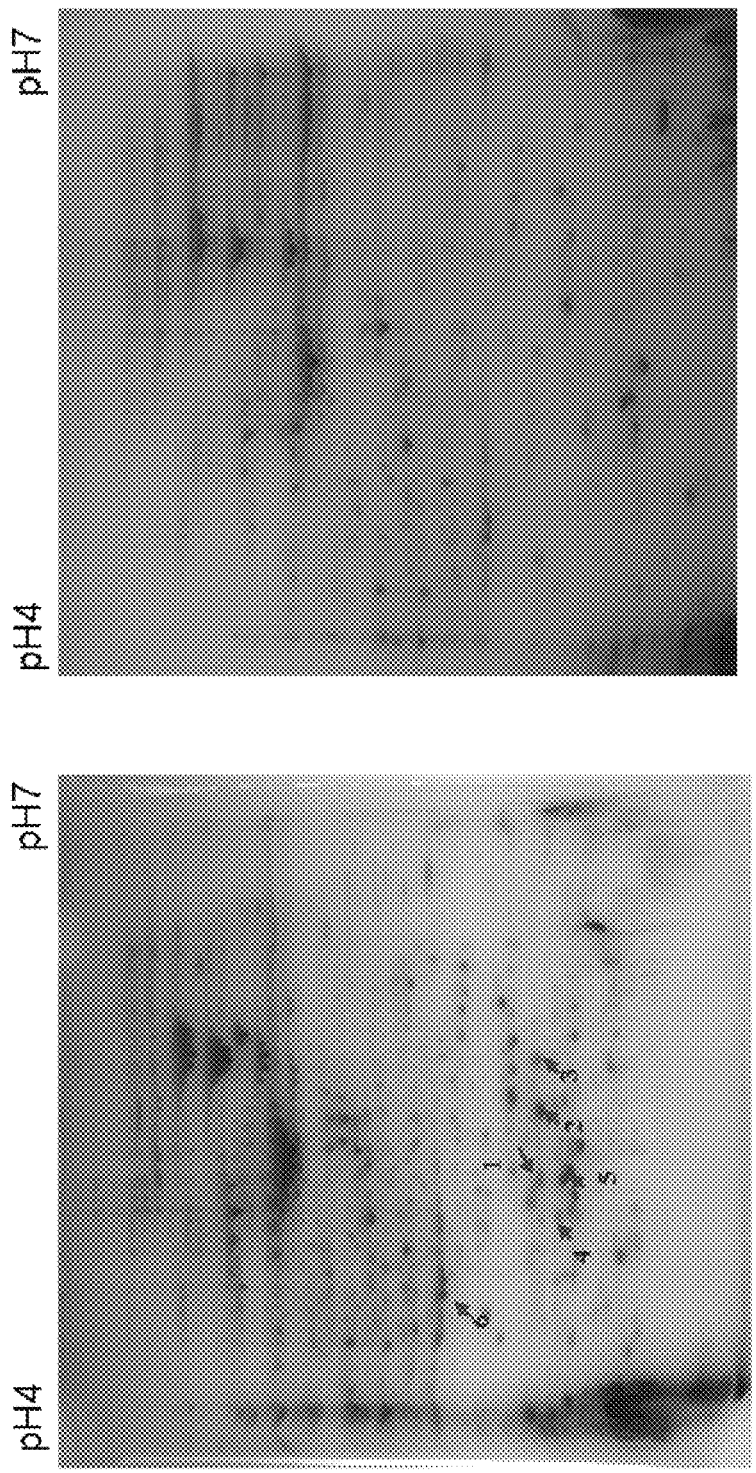
FIG. 7 depicts 2-DE gels (A) Comparing differential protein expression between KIM5+ (wild-type *Y. pestis*) and χ10004-pCD1Ap (ΔrelA233 ΔspoT85) at 26° C. (B) Comparing differential protein expression between KIM5+ (wild-type *Y. pestis*) and χ10004-pCD1Ap (ΔrelA233 ΔspoT85) at 37° C.
Figure 7B:
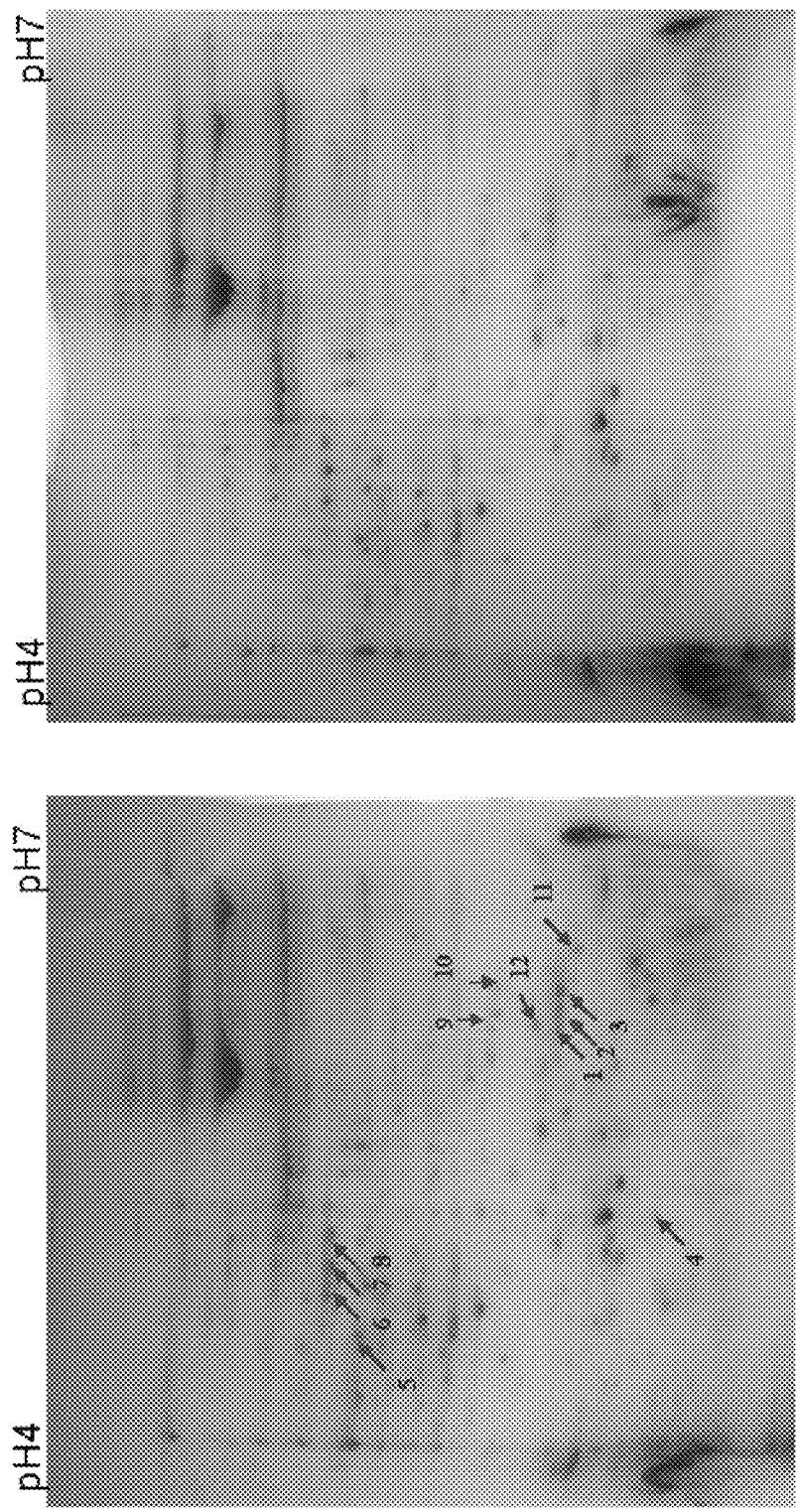

To examine the effect of ppGpp on protein synthesis, the proteome of wild-type and ΔrelA ΔspoT mutant *Y. pestis* strains was compared at different temperatures using two-dimensional electrophoresis (FIG. 7). Our results indicate that deletion of relA and spoT led to reduced synthesis of some metabolic enzymes at flea (26° C.) and human (37° C.) temperatures, and also reduced synthesis of virulence factors such as Pla, LcrH and LcrV at 37° C. (Table 1 and Table 2).

TABLE 1

Differentially expressed proteins identified from *Y. pestis* at 26° C.

| Protein number | Protein name | Accession No. | Function | Method | Fold change WT/ΔrelAΔspoT |
|---|---|---|---|---|---|
| 1 | PanC (pantoate-beta-alanine ligase) | y0785 | biosynthesis of cofactors, carriers: pantothenate | MALDI | 7.3 |
| 2 | hypothetical protein | y2262 | putative | MALDI | 15.2 |
| 3 | S-ribosylhomocysteinase | y0888 | catalyzes the hydrolysis of S-ribosylhomocysteine to homocysteine and autoinducer-2 | MALDI | 8.6 |
| 4 | MetG (methionyl-tRNA synthetase) | y2648 | aminoacyl tRNA synthetases, tRNA modification | MALDI | 2.7 |
| 5 | PyrE (orotate phosphoribosyltransferase) | y0096 | pyrimidine ribonucleotide biosynthesis | MALDI | 2.5 |
| 6 | PyrB (aspartate carbamoyltransferase catalytic Subunit) | y0161 | pyrimidine ribonucleotide biosynthesis | MALDI | 3.6 |

TABLE 2

Differentially expressed proteins identified from *Y. pestis* at 37° C.

| Protein number | Protein name | Accession No. | Function | Method | Fold change WT/ΔrelAΔspoT |
|---|---|---|---|---|---|
| 1 | LcrH (SycD) secretion chaperone | YPCD1.30c | chaperone for YopBD | MALDI | 2.3 |
| 2 | FrsA (fermentation/respiration switch protein) | y0964 | FrsA may promote fermentation | MALDI | 2.8 |
| 3 | MetK (S-adenosylmethionine synthetase) | y3314 | catalyzes the formation of S-adenosylmethionine from methionine and ATP; methionine adenosyltransferase | MALDI | 4.2 |
| 4 | CodA (cytosine deaminase) | y3946 | salvage of nucleosides and nucleotides | MALDI | 1.5 |
| 5 | Pla (outer membrane protease) | YPPCP1.07 | outer membrane protease; involved in virulence in many organisms | MALDI | 2.6 |
| 6, 7, 8 | LcrV (secreted effector protein) | YPCD1.31c | functions in needle complex protein export; Yop secretion and targeting control protein; important for translocation pore formation | MALDI | 7.3 |
| 9 | TrpA (tryptophan synthase subunit alpha) | y2047 | amino acid biosynthesis: Tryptophan | MALDI | 1.6 |
| 10 | TyrS (tyrosyl-tRNA synthetase) | y1966 | aminoacyl tRNA synthetases, tRNA modification | MALDI | 1.6 |
| 11 | hypothetical protein | y2786 | putative membrane protein | MALDI | 2.3 |
| 12 | Kbl (2-amino-3-ketobutyrate coenzyme A ligase) | y0081 | Central intermediary metabolism: pool, multipurpose conversions | MALDI | 1.7 |

Figure 6B:
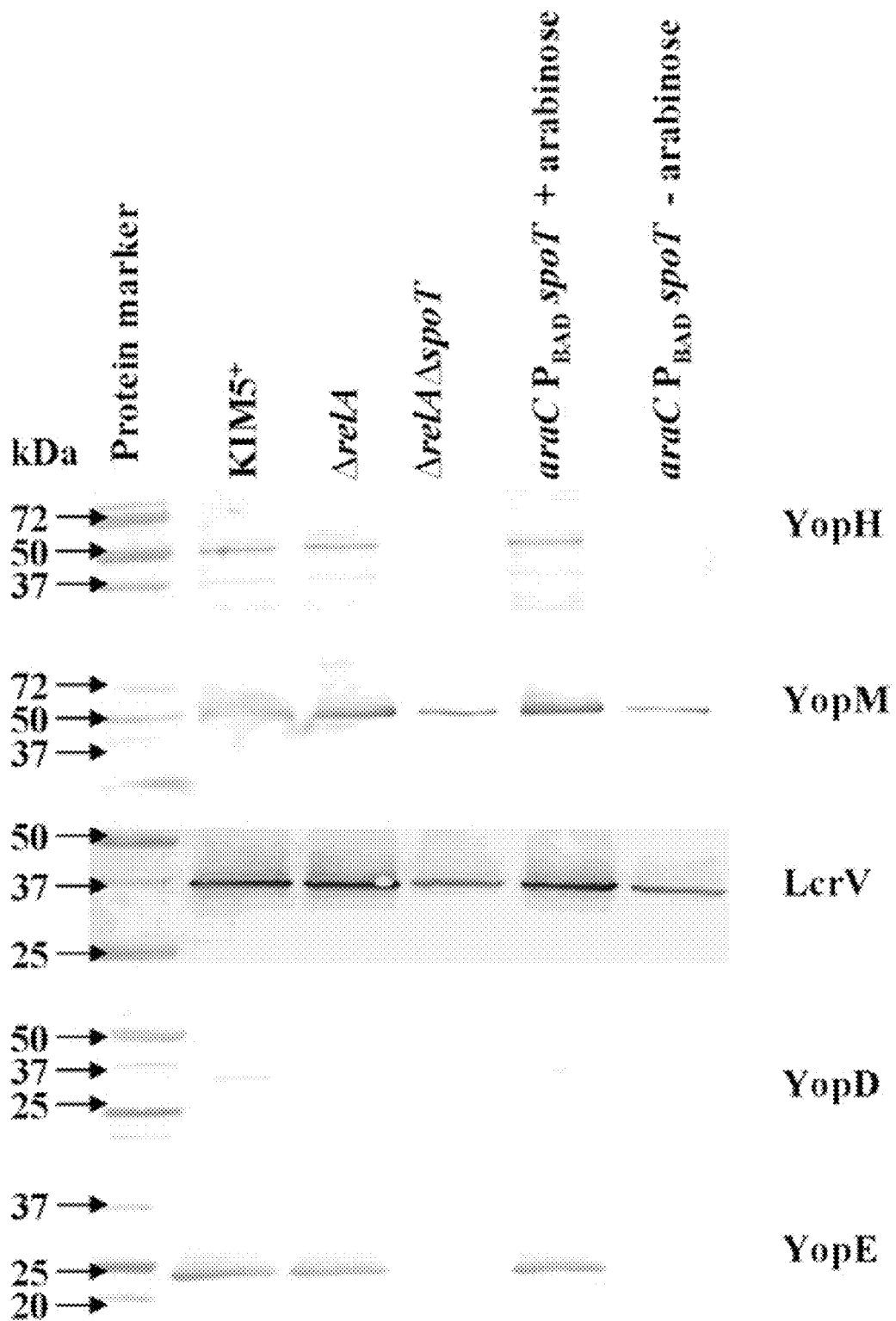

We also evaluated secretion of LcrV and some of the Yops. Recovery of secreted Yop proteins is hampered by degradation due to Pla activity [27]. Therefore, secretion of virulence factors was evaluated in Δpla derivatives, χ10023(pCD1Ap) (Δpla), χ10024(pCD1Ap) (Δpla ΔrelA), χ10025(pCD1Ap) (Δpla ΔrelA ΔspoT) and χ10026(pCD1Ap) (Δpla ΔrelA ΔspoT araC $P_{BAD}$ spoT). The results indicate that LcrV and YopM secretion was reduced slightly in absence of ppGpp (ΔrelA ΔspoT), but secretion of YopH, YopD and YopE were significantly decreased (FIG. 6B).

Example 4

A ΔRelA ΔSpoT Mutant is Attenuated in Mice

Figure 8:
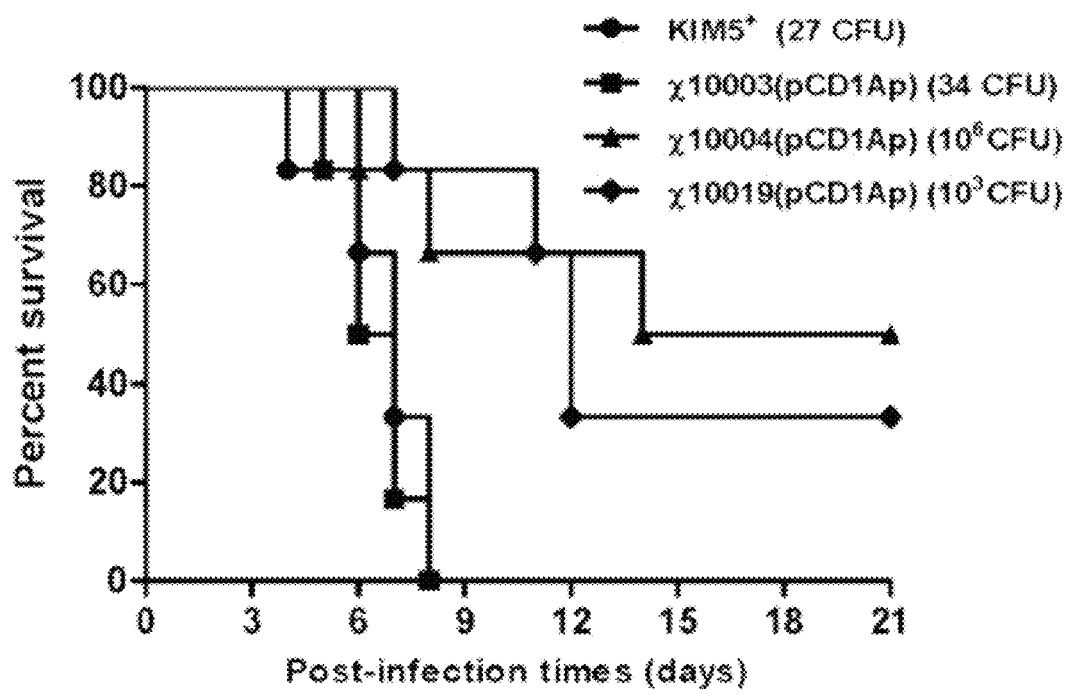
FIG. 8 depicts the survival of Swiss Webster mice (3 mice per strain) infected s.c. with *Y. pestis* KIM5+ (black circles), χ10003(pCD1Ap) (black squares), χ10004 (pCD1Ap) (black triangles) and χ10019(pCD1Ap) cultured with 0.05% arabinose in vitro (black diamonds). The experiment was performed twice with similar results.

To investigate the contribution of ppGpp to the virulence of *Y. pestis*, we infected groups of three Swiss Webster mice subcutaneously with wild-type, χ10003(pCD1Ap) (ΔrelA233), χ10004(pCD1Ap) (ΔrelA233 ΔspoT85) and χ10019(pCD1Ap) (ΔrelA233 ΔspoT85 ΔlacZ516::TT araC $P_{BAD}$ spoT), in which spoT expression is regulated by arabinose availability. Strain χ10019(pCD1Ap) was grown in the presence of arabinose prior to inoculation of mice. Once this strain colonizes host tissues where there is no free arabinose [4], it will become phenotypically SpoT⁻. In preliminary experiments we determined that the $LD_{50}$ of the wild-type strain in mice is, <10 CFU, consistent with previous results [28,29]. Mice given wild-type *Y. pestis* KIM5+ and χ10003 (pCD1Ap) (ΔrelA) succumbed to the infection in a highly synchronous manner (FIG. 8). Only 50% of the mice infected with $5.8 \times 10^5$ CFU of ΔrelA ΔspoT strain χ10004 developed plague after 6 days, and the rate at which the mice died was slower than the rate of those infected with the wild-type strain. The LD50 of χ10004(pCD1Ap) was $5.8 \times 10^5$ CFU. Thus, the lack of ppGpp resulted in a ~100,000-fold increase in the $LD_{50}$ obtained by subcutaneous (s.c.) infection. The $LD_{50}$ of χ10019(pCD1Ap) strain, administered after growth in arabinose was intermediate, at $3.3 \times 10^2$ CFU (~100-fold increase). The $LD_{50}$ of χ10019 (pCD1Ap) was the same as KIM5+ (LD50<10) when inoculated mice were injected with arabinose, indicating full complementation of the attenuation phenotype.

To further evaluate the ability of *Y. pestis* to disseminate to the bloodstream and internal organs, we monitored the growth of both *Y. pestis* KIM5⁺ and χ10004(pCD1Ap) in the lungs, spleens, livers and blood of infected mice over a 7-day period after s.c. injection. Because of the difference in $LD_{50}$ between the two strains, we inoculated mice with different doses of each, $1.5 \times 10^3$ CFU of *Y. pestis* KIM5+ or $1.6 \times 10^6$ CFU of χ10004(pCD1Ap). The kinetics of colonization was similar for both strains (FIG. 9). Despite the difference in dose, the levels of bacteria in blood, spleen and liver were similar for both strains on days 3 and 5. There was an approximate 1.5 log difference in bacteria isolated from lung tissue, indicating that the ΔrelA ΔspoT mutant was less efficient than KIM5+ at reaching the lungs. By day 7, the number of the ΔrelA ΔspoT mutant began to decline in all tissues, indicating clearance by the host, while all of the mice inoculated with wild-type *Y. pestis* had succumbed to the infection.

Example 5

The Immune Responses to ΔrelA ΔspoT *Y. pestis* Strain χ10004(pCD1Ap)

Figure 10A:
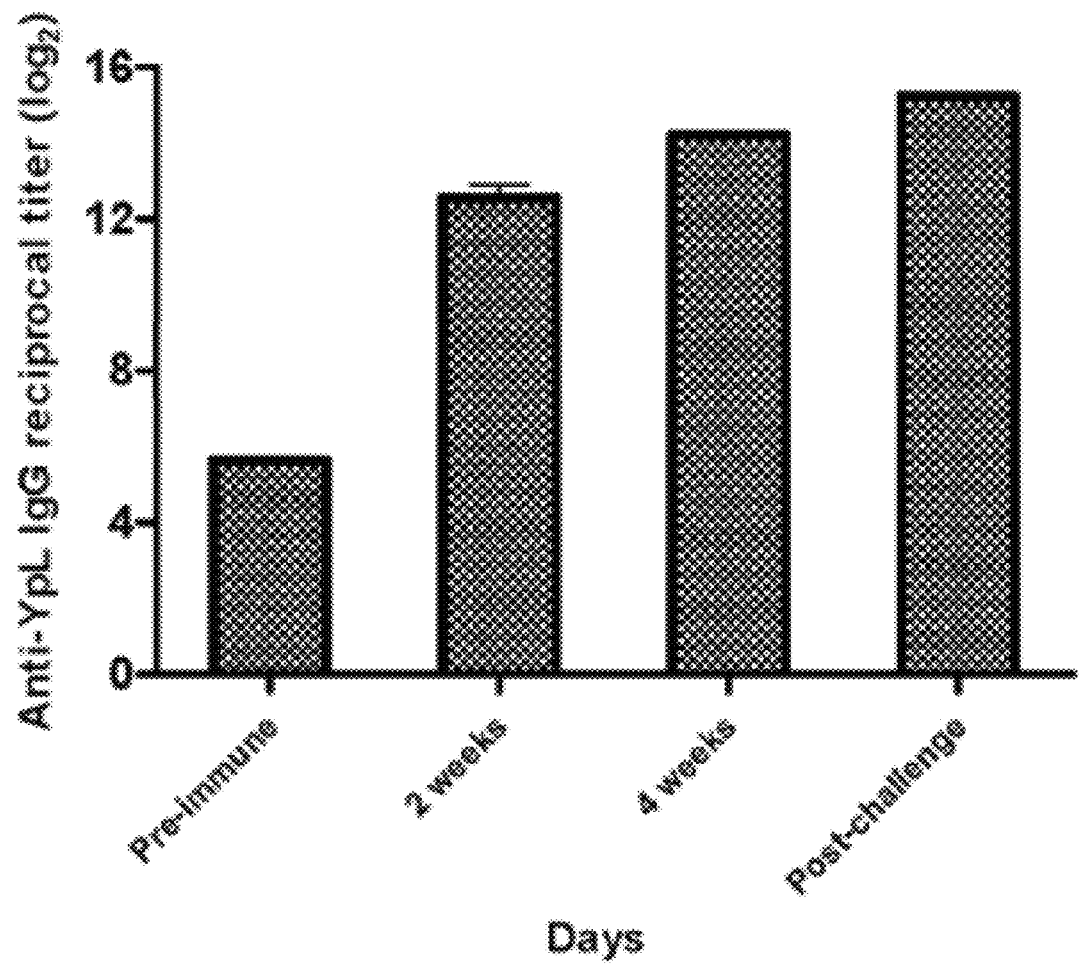

Because χ10004 was attenuated, we explored its potential as a vaccine. To evaluate the immune responses to ΔrelA ΔspoT *Y. pestis* strain χ10004(pCD1Ap), two groups of 10 mice each were immunized s.c. with $2.5 \times 10^4$ CFU on day 0. Two groups of 4 mice each were injected with PBS as controls. Mice were challenged on day 35 with either $1.5 \times 10^5$ (s.c.) or $2.0 \times 10^4$ (i.n.) CFU of *Y. pestis* KIM5+. Blood was taken at 2 and 4 weeks post immunization and 2 weeks after challenge. Serum IgG responses to *Y. pestis* whole cell lysates (YpL) from immunized mice were measured by ELISA (FIG. 10A). At two weeks after immunization, the reciprocal anti-*Y. pestis* serum IgG titers were greater than 1,000 and increased at 4 weeks and after challenge.

Figure 10B:
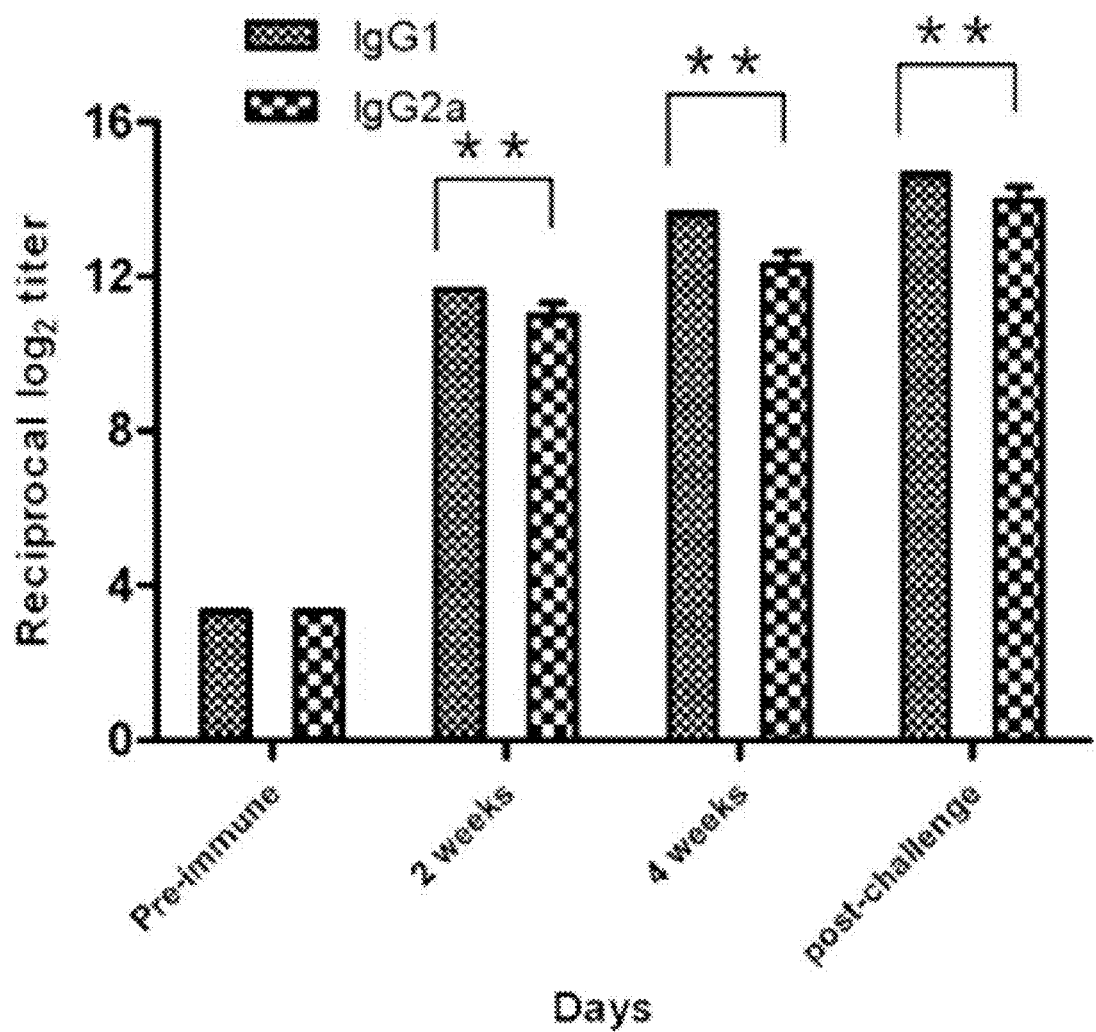

The serum immune responses to YpL were further examined by measuring the levels of IgG isotype subclasses IgG1 and IgG2a. Th1 cells direct cell-mediated immunity and promote class switching to IgG2a, and Th2 cells provide potent help for B-cell antibody production and promote class switching to IgG1 [30]. The level of anti-YpL IgG1 and IgG2a isotype antibodies rapidly increased after vaccination and gradually increased at 2 weeks, 4 weeks and post-challenge (FIG. 10B). At 2 and 4 weeks post-immunization, the ratio of IgG1 to IgG2a was 1.06:1 and 1.2:1 respectively, indicating an initial mixed Th1/Th2 response, which developed into a slight Th2 bias by week 4. This Th2 bias continued after challenge as well.

Example 6

Immunization with a ΔRelA ΔSpoT *Y. Pestis* Strain χ10004(pCD1Ap) can Protect Against Plague Challenge To evaluate the protective efficacy of ΔrelA ΔspoT *Y. pestis* strain χ10004(pCD1Ap) against the bubonic and pneumonic forms of plague, immunized mice were challenged on day 35 with either $1.5 \times 10^5$ (s.c.) or $2.0 \times 10^4$ (i.n.) CFU of *Y. pestis* KIM5+. Post-challenge survival was monitored for 14 days. A single s.c. vaccination could provide complete protection against s.c. challenge without any symptoms (FIG. 11A) and 60% protection against pulmonary challenge (FIG. 11B). None of the mice immunized with PBS survived either challenge (FIG. 11).

Example 7

Induction of Cytokines by *Y. Pestis* KIM5+ and ΔRelA ΔSpoT Strain χ10004(pCD1Ap)

Cytokines are critical to the development and functioning of both the innate and adaptive immune responses. They are often secreted by immune cells that have encountered pathogens, thereby activating and recruiting additional immune cells to increase the system's response to the pathogen. Previously, LcrV has been demonstrated to be an immunomodulator (TNF-α and IFN-γ down-regulation and IL-10 induction) both in vivo and in vitro [31,32,33]. Since the synthesis and secretion of LcrV is reduced in the ΔrelA ΔspoT mutant, we compared production of three cytokines (IL-10, INF-γ and TNF-α) in mice infected with *Y. pestis* KIM5+ and χ10004 (pCD1Ap). For this experiment, groups of three Swiss-Webster mice were inoculated via the s.c. route with $1.5 \times 10^3$ CFU of *Y. pestis* KIM5+ or $1.6 \times 10^6$ CFU of χ10004(pCD1Ap). A group of uninfected mice served as controls. Blood was collected via cardiac puncture 3 and 5 days later for cytokine analysis. Measurements indicated that levels of IL-10 were higher in the sera of animals infected with *Y. pestis* KIM5+ than that of χ10004(pCD1Ap) (FIG. 12). The pro-inflammatory cytokines IFN-γ and TNF-α were not detected in sera from mice inoculated with either strain (data not shown)

Materials and Methods for Examples 1-7

Bacterial Strains, Culture Conditions and Plasmids

All bacterial strains and plasmids used in this study are listed in Table 3. All strains were stored at −70° C. in phosphate-buffered glycerol. *Y. pestis* cells were grown routinely at 28° C. on Congo red agar from glycerol stocks and then grown in heart infusion broth (HIB) or on tryptose-blood agar base (TBA) [1]. The chemically defined medium PMH2 was used routinely [2]. All *E. coli* strains were grown routinely at 37° C. in LB broth [3] or LB solidified with 1.2% Bacto Agar (Difco).

TABLE 3

Bacterial strains and plasmids used in this study.

| Strains | Relevant genotype or Annotation | Source or derivation |
|---|---|---|
| *E. coli* TOP10 | F⁻mcrA Δ (mrr-hsdRMS-mcrBC) φ80lacZΔM15 ΔlacX74 recA1 araD139 Δ (ara-leu)7697 galU galK rpsL endA1 nupG | Invitrogen |
| *Y. pestis* KIM6⁺ | Pgm⁺, pMT1, pPCP1, cured of pCD1 | [2] |
| *Y. pestis* KIM5⁺ | *Y. pestis* KIM6+ pCD1Ap | [2] |
| χ10003 | ΔrelA233 *Y. pestis* KIM6+ | [5] |
| χ10004 | ΔrelA233 ΔspoT85 *Y. pestis* KIM6+ | [5] |
| χ10019 | ΔrelA233 ΔspoT85 ΔlacZ516::TT araC $P_{BAD}$ spoT *Y. pestis* KIM6+ | This study |
| χ10021 | spoT412:: 3xFlag-Kan *Y. pestis* KIM6+ | This study |
| χ10022 | ΔrelA233 ΔspoT85 ΔlacZΩTT araC $P_{BAD}$ spoT413:: 3xFlag-Kan *Y. pestis* KIM6+ | This study |
| χ10023 | Δpla-525 *Y. pestis* KIM6+ | This study |
| χ10024 | ΔrelA233 Δpla-525 *Y. pestis* KIM6+ | This study |
| χ10025 | ΔrelA233 ΔspoT85 Δpla-525 *Y. pestis* KIM6+ | This study |
| χ10026 | ΔrelA233 ΔspoT85 Δpla-525 ΔlacZ516::TT araC $P_{BAD}$ spoT *Y. pestis* KIM6+ | This study |
| χ10003(pCD1Ap) | ΔrelA233 *Y. pestis* KIM6+ pCD1Ap | This study |
| χ10004(pCD1Ap) | ΔrelA233 ΔspoT85 *Y. pestis* KIM6+ pCD1Ap | This study |
| χ10019(pCD1Ap) | ΔrelA233 ΔspoT85 ΔlacZ::TT araC $P_{BAD}$spoT *Y. pestis* KIM6+ pCD1Ap | This study |
| χ10023(pCD1Ap) | Δpla-525 *Y. pestis* KIM6+ pCD1Ap | This study |
| χ10024(pCD1Ap) | ΔrelA233 Δpla-525 *Y. pestis* KIM6+ pCD1Ap | This study |
| χ10025(pCD1Ap) | ΔrelA233 ΔspoT85 Δpla-525 *Y. pestis* KIM6+ pCD1Ap | This study |
| χ10026(pCD1Ap) | ΔrelA233 ΔspoT85 Δpla-525 ΔlacZ516::TT araC $P_{BAD}$ spoT *Y. pestis* KIM6+ pCD1Ap | This study |

| Plasmids | | Source |
|---|---|---|
| pUC18 | For cloning and sequencing | Invitrogen |
| pCD1Ap | 70.5-kb pCD1 with bla cassette inserted into 'yadA; 71.7-kb Lcr⁺ Apʳ | [2] |
| pCP20 | Apʳ Cmʳ, FLP recombinase expression | [7] |
| pKD3 | Apʳ Cmʳ, cat cassette template | [7] |
| pKD46 | Apʳ, λ Red recombinase expression | [7] |
| pYA3700 | TT araC $P_{BAD}$ cassette plasmid, Apʳ | US Patent. Publ. 2006-0140975 |
| pSUB11 | Knʳ, 3xFlag-tagged | [6] |
| pYA4373 | The cat-sacB cassette in the PstI and SacI sites of pUC18. | pUC18 |
| pYA4573 | The lacZ-U (upstream gene sequence of lacZ), and lacZ-D (downstream gene sequence of lacZ) fragment were cloned into the SphI/PstI sites and SacI/EcoRI sites of pYA3700 respectively. | pYA3700 |
| pYA4574 | The spoT gene with new SD sequence was cloned into the XhoI and SacI sites of pYA4573. | pYA4573 |
| pYA4575 | The cat-sacB cassette from pYA4373 was ligated into PstI site of pYA4574. | pYA4574 |
| pYA4642 | The C-terminal spoT gene fragment (510 bp) was cloned into HindIII and BamHI sites of pUC18. | pUC18 |
| pYA4643 | The spoU' gene fragment (downstream sequence of spoT) was cloned into SacI and EcoRI sites of pYA4642. | pYA4642 |
| pYA4644 | The lacZ-D gene fragment (downstream sequence of lacZ) was cloned into SacI and EcoRI sites of pYA4642. | pYA4642 |
| pYA4645 | The 3xFlag::kan gene fragment was cloned into SacI and BamHI sites of pYA4643. | pYA4643 |
| pYA4646 | The 3xFlag::kan gene fragment was cloned into SacI and BamHI sites of pYA4644. | pYA4644 |
| pYA4647 | The pla-U fragment (upstream sequence of pla) was cloned into the EcoRI and PstI sites of pUC18. | pUC18 |
| pYA4648 | The pla-D fragment (downstream sequence of pla) was cloned into the SphI and PstI sites of pYA4647. | pYA4647 |
| pYA4649 | The cat cassette (including Flp recombination site) was cloned into the PstI site of pYA4648. | pYA4648 |

Plasmid Construction

All primers used are listed in Table 4. The original source for the tightly regulated araC $P_{BAD}$ in pYA3700 was *E. coli* K-12 strain χ289 [4]. For construction of the $P_{BAD}$ spoT insertion/deletion into lacZ, primer sets of LacZ1/LacZ2 and LacZ3/LacZ4 were used for amplifying lacZ-U (upstream gene sequence of lacZ), and lacZ-D (downstream gene sequence of lacZ) fragment, respectively. The lacZ-U and lacZ-D fragments were cloned into the SphI/PstI sites and SacI/EcoRI sites of pYA3700 to form pYA4573. The spoT gene fragment was amplified using SpoT-1 and SpoT-2 primers. The primer SpoT-1 containing the new SD sequence is shown Table 4. The spoT fragment was cloned into pYA4573 to construct pYA4574. Plasmid pYA4574 was digested with PstI, blunt ended with T4 DNA polymerase and dephosphorylated with shrimp alkaline phosphatase (Promega). The cat-sacB fragment was cut from pYA4373 using PstI and SacI restriction endonucleases and blunted by T4 DNA polymerase. Then, the cat-sacB fragment was ligated into PstI site of pYA4574 to form plasmid pYA4575.

TABLE 4

Oligonucleotides used in this work

| Name | Sequence | Seq. ID No. |
|---|---|---|
| LacZ1 [a] | 5' cgg<u>ctgcag</u>cccatcactccagcgcagaact 3' (PstI) | 1 |
| LacZ2 | 5' cgg<u>gcatgc</u>tccagcccattcaggcttat 3' (SphI) | 2 |
| LacZ3 | 5' cgg<u>gaattc</u>caaaggagcaatgcatgtatgg 3' (EcoRI) | 3 |
| LacZ4 | 5' cgg<u>gagctc</u>catgtgttgccaactggctg 3' (SacI) | 4 |
| LacZ5 | 5' ctaaattgttatctcttcgtag 3' | 5 |
| LacZ6 | 5' tgcagggagatgagttaacaatg 3' | 6 |
| SpoT-1 [a,b] | 5' cgg<u>ctcgag</u>GGAGTGaaacgTTGtacctgtttgaaagcct 3' (XhoI) | 7 |
| SpoT-2 [a] | 5' cgg<u>gagctc</u>ttaattgcgattacggctaactttaacc 3' (SacI) | 8 |
| Pla1 | 5' cgg<u>gaattc</u>agcaaaacagacaaacgcctgctgg 3' (EcoRI) | 9 |
| Pla2 | 5' cgg<u>ctgcag</u>tagacacccttaatctctctgcatg 3' (PstI) | 10 |
| Pla3 | 5' cgg<u>ctgcag</u>tacagatcatatctctcttttcatcctc 3' (PstI) | 11 |
| Pla4 | 5' cgg<u>gcatgc</u>ctggtgcgtatagctgaggatgaat 3' (SphI) | 12 |
| Pla5 | 5' gagataacgtgagcaaaacaaaatctggtcg 3' | 13 |
| Pla6 | 5' gagccttttatgcgttcgatccgattcg 3' | 14 |
| Cm1 | 5'cgga<u>ctgcag</u>atgggaattagccatggtcc 3' (PstI) | 15 |
| Cm2 | 5'cgg<u>ctgcag</u>tgtaggctggagctgcttcg 3' (PstI) | 16 |
| SpoTC-1 | 5' cgg<u>aagctt</u>atgagcgtagtggtggctaa 3' (HindIII) | 17 |
| SpoTC-2 | 5' cgg<u>ggatcc</u>attgcgattacggctaactt 3' (BamHI) | 18 |
| SpoTD-1 | 5'cgg<u>gagctc</u>taacgcctatgaatcctcaacgctatg 3' (SacI) | 19 |
| SpoTD-2 | 5' cgg<u>gaattc</u>tgtgtgtccgtttatacatc 3' (EcoRI) | 20 |
| Flag-1 | 5' cgg<u>ggatcc</u>gactacaaagaccatgacggtgatt 3' (BamHI) | 21 |
| Flag-2 | 5' cgg<u>gagctc</u>catatgaatatcctccttagttcctat 3' (SacI) | 22 |
| Cm-V | 5'gttgtccatattggccacgttta3' | 23 |
| SacB-V | 5' gcagaagagatattttaattgtggacg 3' | 24 |
| araC-V | 5'catccaccgatggataatcgggta3' | 25 |
| 16S rRNA primer1 | 5' aggcgacgatccctagctggtctga 3' | 26 |
| 16S rRNA primer2 | 5' cgtttacagcgtggactaccagggt 3' | 27 |
| IcrV primer1 | 5' tcctagcttattttctacccgagga 3' | 28 |
| IcrV primer2 | 5' ttaattcggcggtaagctcagctaa 3' | 29 |
| yopB primer1 | 5' tgtttcagtgctaacgaagtttacgc 3' | 30 |

TABLE 4-continued

Oligonucleotides used in this work

| Name | Sequence | Seq. ID No. |
|---|---|---|
| yopB primer2 | 5' acaatcactgaggctatggcgctga 3' | 31 |
| yopD primer1 | 5' tcttgttgttgctgttggaactggc 3' | 32 |
| yopD primer2 | 5' gttgttcgcggccagcaatattact 3' | 33 |
| yopE primer1 | 5' catttgctgcctgcgttagatcaac 3' | 34 |
| yopE primer2 | 5' gccaaaatacatgcagcagttgaat 3' | 35 |
| yopH primer1 | 5' tcgtcaggtatctcgattggtgcag 3' | 36 |
| yopH primer2 | 5' ccattgccgacacttcttaagtcat 3' | 37 |
| yopJ primer1 | 5' tcacgtatggatgtagaagtcatgc 3' | 38 |
| yopJ primer2 | 5' gttttttgtccttattgccagcatcg 3' | 39 |
| yopK primer1 | 5' gtgctttatgtaccgctcttgaaca 3' | 40 |
| yopK primer2 | 5' gtcaatatcgctgacatgttgccat 3' | 41 |
| yopM primer1 | 5' acgtcattcttctaatttaactgagatg 3' | 42 |
| yopM primer2 | 5' aagtgatttcaggctctgcggtaat 3' | 43 |
| yopT primer1 | 5' tcaaggatagcgtttaataattgatccag 3' | 44 |
| yopT primer2 | 5' tttatgtgcacattggatcaggagc 3' | 45 |

* a: the restriction endonuclease sites are underlined
b: the bold capital letters show the Shine-Dalgarno (SD) sequence and the TTG start codon To construct a spoT-3×-flag-kan fusion, a C-terminal spoT gene fragment (510 bp) was amplified using SpoTC-1 and SpoTC-2 primers and cloned into HindII and BamHI sites of pUC18 to construct pYA4642. The spoU' gene fragment (sequence downstream of spoT) and lacZ-D gene fragment (sequence downstream of lacZ) were amplified from genomic DNA using SpoTD-1/SpoTD-2 and LacZ3/LacZ4 primers, respectively. The spoU' and lacZ-D fragment were cloned into SacI and EcoRI sites of pYA4642 to form pYA4643 and pYA4644, respectively. Then the 3× flag-kan gene fragment amplified from pYA4045 was cloned into SacI and BamHI sites of pYA4643 and pYA4644 to construct pYA4645 and pYA4646.

To delete the pla gene from plasmid pPCP1, plasmids pYA4647, pYA4648, and pYA4649 were constructed. The pla-U fragment was amplified from total DNA of *Y. pestis* KIM6+ using Pla1 and Pla2 primers and cloned into the EcoRI and PstI sites of pUC18 to form pYA4647. The pla-D fragment was amplified using Pla3 and Pla4 primers. The pla-D fragment was cloned into pYA4647 to construct pYA4648. The cat cassette (including Flp recombination site) amplified using Cm1 and Cm2 primers was cloned into the PstI site of pYA4648 to form pYA4649.

Construction of *Y. Pestis* Mutant Strains

The construction of strains χ10003 and χ10004 using a two-step recombination method was previously described [5]. Strain χ10019 was constructed from strain χ10004 using similar methods. Briefly, plasmid pKD46 was introduced into χ10004 by electroporation. A linear lacZ-U-cat-sacB-TT araC $P_{BAD}$ spoT-lacZ-D fragment was purified from plasmid pYA4575 by digestion with EcoRI and SphI and transformed into χ10004 (pKD46) competent cells. Electroporants were isolated on TBA+Cm (10 μg/ml) plates. Integration of the lacZ-U-cat-sacB-TT araC $P_{BAD}$ spoT-lacZ-D fragment into the correct site of the chromosome was verified by PCR. Colonies with the correct PCR profile were streaked onto TBA+Cm (10 μg/ml)+5% Sucrose plates to verify sucrose sensitivity and onto HIB Congo Red+Cm (10 μg/ml) plates to confirm the presence of the pgm locus. To remove the cat-sac cassette from the chromosome, electrocompetent cells were prepared from a sucrose-sensitive isolate and electroporated with approximately 1 μg of a linear DNA (lacZ-U-TT araC) cut from pYA4574 using SphI and BamHI. Electroporants were selected on TBA+5% sucrose plates incubated at 30° C. Colonies were tested using PCR to validate that the cat-sacB cassette was eliminated. Plasmid pKD46 was cured from a single colony isolate of a sucrose-resistant, chloramphenicol-sensitive strain to yield χ10019.

To construct strains expressing spoT tagged with the Flag epitope [6], plasmid pKD46 was introduced into *Y. pestis* KIM6+ and χ10019. The resulting strains were electroporated with ~0.5 μg of spoTC-3× flag-kan-spoU' and spoTC-3× flag-kan-lacZ-D cut from pYA4645 and pYA4646, respectively. Electroporants were selected on TBA+Kan (20 μg/ml) plates at 37° C. The resulting colonies were verified using PCR to confirm that the 3× flag-kan fragment was correctly inserted into the chromosome. Plasmid pKD46 was cured from single colony isolates of *Y. pestis* KIM5+ or χ10019 derivatives to yield χ10021 and χ10022, respectively.

To construct Pla⁻ mutants, *Y. pestis* KIM6+ (pKD46), χ10003 (pKD46), χ10004 (pKD46) and χ10019 (pKD46) competent cells were electroporated with ~0.5 μg of PCR amplified, gel purified pla-U::cat:pla-D fragment obtained with primers Pla1 and Pla4 using plasmid pYA4649 as the template. Electroporants were selected on TBA+Cm (10 µg/ml) plates and were subsequently verified by PCR to confirm that pla was deleted. Plasmid pCP20 was introduced into the pla mutant strains and the $Cm^R$ cassette was removed by flip recombinase [7]. Plasmid pCP20 was cured from resulting single colony isolates to yield χ10023, χ10024, χ10025 and χ10026. Then, the pCD1Ap plasmid was transformed into *Y. pestis* KIM6+, χ10003, χ10004, χ10019, χ10023, χ10024, χ10025 and χ10026, respectively to form *Y. pestis* KIM5+, χ10003(pCD1Ap), χ10004(pCD1Ap), χ10019 (pCD1Ap), χ10023 (pCD1Ap), χ10024(pCD1Ap), χ10025 (pCD1Ap) and χ10026 (pCD1Ap) under BSL3 containment.

ppGpp Assay ppGpp was detected using a slight modification of previously described procedures [8,9]. To starve cells for amino acids, strains were grown overnight in HIB medium at 26° C. The cells were then harvested and washed three times with PBS and resuspended to an $OD_{620}$ of 0.15 in 1 ml of modified PMH2 medium lacking L-phenylalanine [9]. The culture was shaken at 250 rpm at 26° C. for approximately 5 h until the $OD_{620}$ reached 0.25, whereupon, [$^{32}$P] $H_3PO_4$ was added to 100 μCi/ml. Cells were incubated for an additional 1 h at 26° C. Following incubation, an equal amount of chilled 90% formic acid was added to the cell suspension. The ice-cold suspensions were then rigorously vortexed followed by three freeze-thaw cycles. The acid extracts were centrifuged in a minifuge set at the highest speed for 5 min, and 5 ml of supernatant was then applied to a polyethyleneimine-cellulose thin-layer chromatography plate (TLC). The TLC plates were developed at room temperature with 1.5 M $KH_2PO_4$ (pH 3.4). The developed plates were then air-dried and visualized by autoradiography using X-ray film at −70° C. To starve cells for carbon, strains were grown overnight in HIB medium. For strain χ10019, two cultures were grown, one with and one without the addition of 0.05% arabinose. The cells were harvested, washed three times using PBS and resuspended to an $OD_{620}$ of 0.15 in 1 ml of modified PMH2 medium without glucose or arabinose. Cultures were grown, labeled and evaluated by TLC as described above.

Analysis of Virulence Factor Transcription by RT-PCR

Total RNA was extracted from bacterial cells using TRIzol Reagent (Invitrogen) according to the manufacturer's recommendations. RNA samples were treated with DNase I for 10 min at 37° C. to degrade contaminating DNA followed by inactivation of DNase I with 2 mM EDTA and heating to 65° C. for 10 min. RNA was then precipitated with sodium acetate and ethanol and washed with 70% ethanol prior to performing RT-PCR. RNA samples of 200 ng were used for reverse transcription, using random hexamer primers and Superscript II reverse transcriptase as described by the manufacturer (Invitrogen). PCR amplification was performed using the lcrV yopB, yopD, yopE, yopH, yopJ, yopK, yopM, yopT or 16S rRNA primer pairs listed in Table 4. RNA samples were used as templates in PCR reactions for RT minus controls. Twenty cycles of amplification were performed using an annealing temperature of 58° C. Products were then separated on a 1% agarose gel, stained with ethidium bromide and imaged for visualization of appropriately sized PCR products. In all cases, reactions were performed in triplicate.

Protein Analysis

Secreted virulence factors were prepared by using a modification of previously described methods [10]. *Y. pestis* was grown in HIB medium overnight at 26° C. The cells were then harvested and washed three times using PMH2, inoculated to 40 ml of fresh PMH2 medium to an $OD_{600}$ of 0.05 and shaken overnight at 26° C. Cultures were shifted to 37° C. for 6 h with shaking to provide mild aeration. Bacterial cells were removed by centrifugation for RNA extraction. Secreted virulence factors from the culture supernatants were concentrated by precipitation with 10% (w/v) trichloroacetic acid overnight at 4° C. Precipitated proteins were collected by centrifugation, washed with ice-cold acetone, and dissolved in 0.05 M Tris-HCl buffer (pH 9.5). Insoluble materials were removed by centrifugation at 12 500 g for 15 min and the protein concentration in the supernatant was determined using the DC protein assay kit (Bio-Rad Laboratories, Hercules, Calif.). Samples containing 200 μg proteins were heated at 95° C. for 5 min in protein sample buffer containing 2-mercaptoethanol and analyzed by sodium dodecyl sulfate-polyacrylamide gel electrophoresis (SDS-PAGE) with 10% polyacrylamide. Proteins were transferred to nitrocellulose membranes. The membranes were blocked with 5% skim milk in PBS, incubated with rabbit polyclonal antibodies specific for the indicated Yop proteins or LcrV, and washed with PBS-Tween 20. Then alkaline phosphatase-conjugated goat anti-rabbit immunoglobulin G (IgG) (Sigma, St. Louis, Mo.) was added in PBS-Milk. Immunoreactive bands were detected by the addition of NBT/BCIP (Sigma, St. Louis, Mo.). The reaction was stopped after 5 min by washing with several large volumes of deionized water.

Two-Dimensional Gel Electrophoresis

Comparison of two dimensional protein profiles was carried out as previously described [11]. *Y. pestis* KIM5+ and χ10004(pCD1Ap) were grown at 26° C. or 37° C. in 5 ml of best-case-scenario (BCS) medium without $Ca2^+$. The cultures were harvested by centrifugation and washed once with low salt PBS (0.1×). Cells were resuspended in 1 ml lysis buffer containing 8M Urea, 0.05M DTT, 2% (w/v) CHAPS and 0.2% (w/v) ampholytes. Proteins were extracted by vortexing 1 ml cell samples in lysis buffer with 0.2 mm glass beads ten times for 30 s with cooling between vortexing. The samples were centrifuged at 2500 g for 5 min to remove the beads. The bead-free supernatant was centrifuged at 15000 g for 15 min at 4° C. to remove cellular debris. The cell-free lysates were immediately placed on ice and protease inhibitor was added. The lysates were retreated with a 2D protein cleanup kit (Bio-Rad, Hercules, Calif.) and protein concentration was determined using the Bio-Rad Protein Assay kit.

Protein lysates (300 μg) were mixed with rehydration buffer (Bio-Rad) in a total volume of 300 μl. Equal amounts (300 μg) of protein were isoelectrically focused using 17 cm pH 4-7 strips followed by 18.3×19.3 cm 8-16% SDS-PAGE using Midi-Protean II 2D cell (Bio-Rad). Gels were stained with Coomassie Brilliant Blue R-250 (Bio-Rad) and visualized using Gel Doc XR system (Bio-Rad). Protein expression levels from protein spots on gels were compared between the different samples. Gel analysis was performed using the PDQuest3 2-D Analysis Software (Bio-Rad) to determine differential expression. Differentially expressed protein spots were excised and were digested with In-Gel Tryptic Digestion Kit (Pierce, Rockford, Ill.). Peptide digests were analyzed using a Voyager DE STR MALDI-TOF mass spectrometer (Applied Biosystems, Framingham, Mass.). Data were searched in bacterial proteomics database using Aldente in ExPASy Proteomics Server. This experiment was performed four times with similar results.

Virulence Studies in Mice

Single colonies of each strain were used to inoculate HIB cultures and grown overnight at 26° C. To select for plasmid pCD1Ap, ampicillin was added into the medium at a concentration of 25 μg/ml. Bacteria were diluted into 10 ml of fresh HIB enriched with 0.2% xylose and 2.5 mM $CaCl_2$ to obtain an $OD_{620}$ of 0.1 and incubated at 26° C. for s.c. infections (bubonic plague) or at 37° C. for intranasal (i.n.) infections (pneumonic plague). Both cultures were grown to an $OD_{620}$ of 0.6. The cells were then harvested and the pellet resuspended in 1 ml of isotonic PBS. All animal procedures were approved by the Arizona State University Animal Care and Use Committee. Female 7-week-old Swiss Webster mice from Charles River Laboratories were inoculated by s.c. injection with 100 ml of bacterial suspension. Actual numbers of colony-forming units (CFU) inoculated were determined by plating serial dilutions onto TBA agar. To determine 50% lethal dose ($LD_{50}$), five groups of six mice were infected with serial dilutions of the bacterial suspension. For in vivo complementation of strain of χ10019(pCD1Ap), 120 mg of L-arabinose dissolved in PBS was intraperitoneally administered to mice on the day of inoculation and once a day thereafter [12]. Mice were monitored twice daily for 21 days, and the $LD_{50}$ was calculated as described [13].

For colonization/dissemination analysis, 3 mice per time point were infected by s.c. injection in the front of the neck. At the indicated times after infection, mice were euthanized, and samples of blood, lungs, spleen and liver were removed. The bacterial load for each organ was determined by plating dilutions of the homogenized tissues onto TBA with ampicillin plates and reported as CFU per gram of tissue or CFU per ml blood. Infections were repeated in at least two independent experiments.

Preparation of Bacterial Antigens

Bacterial antigens used for ELISA were prepared from fresh cells. Briefly, single colonies of *Y. pestis* KIM5+ were inoculated into HIB media and cultured overnight at 26° C. Cells were switched to 37° C. for 6 h. Bacterial cultures were centrifuged at 5,000×g for 10 min, the pellet was washed once with sterile PBS and resuspended in sterile PBS. Bacterial cells were broken using 0.2 mm glass beads 10 times for 60 s with cooling between vortexing (with 2 min incubation on ice between cycles). The whole bacterial lysate was sterilized by UV light and sterility was confirmed by TBA agar culture. The lysate was frozen at −80° C. until use. Protein content was determined by BCA analysis per manufacturer's instructions (Sigma).

Enzyme-Linked Immunosorbent Assay (ELISA)

Mice were lightly anesthetized using ketamine and xylazine mixture administered intramuscularly. Blood was collected by retro-orbital sinus puncture for the determination of antibody titers at different time points. ELISA was used to assay serum antibodies against the whole cell lysate of *Y. pestis* KIM5+. Sera were tested for IgG at a starting dilution of 1:1000, and for IgG1 and IgG2a at 1:100, respectively.

Polystyrene 96-well flat-bottom microtiter plates (Dynatech Laboratories Inc., Chantilly, Va.) were coated with 200 ng/well of *Y. pestis* whole cell lysates. Antigens suspended in sodium carbonate-bicarbonate coating buffer (pH 9.6) were applied in 100 μl volumes to each well. The coated plates were incubated overnight at 4° C. Free binding sites were blocked with a blocking buffer (phosphate-buffered saline [PBS; pH 7.4], 0.1% Tween 20, and 1% bovine serum albumin). A 100 μl volume of serially diluted sample was added to individual wells in triplicate and incubated for 1 h at 37° C. Plates were treated with biotinylated goat anti-mouse IgG, IgG1, or IgG2a (Southern Biotechnology Inc., Birmingham, Ala.). Wells were developed with streptavidin-horseradish peroxidase conjugate (Invitrogen, Carlsbad, Calif.), followed by 2,2-azino-bis-(3-ethylbenzthiazoline-6-sulfonic acid) (ABTS) (Sigma) in sodium citrate buffer containing 0.03% hydrogen peroxide ($H_2O_2$). After a 10 min incubation at 37° C. in the dark, color development (absorbance) was recorded at 405 nm using an automated ELISA plate reader (model EL311SX; Biotek, Winooski, Vt.). Absorbance readings that were 0.1 higher than PBS control values were considered positive.

In Vivo Cytokine Analysis

Cytokines were quantitated by a double-sandwich enzyme-linked immunosorbent assay (ELISA) as described previously [33]. Mice in groups of three were euthanized at intervals by terminal bleeding under anesthesia. Pooled blood was allowed to clot overnight at 4° C., and serum was separated by centrifugation at 10,000 g for 10 min. Sera were filtered once through a 0.22 μm syringe filter, cultured on TBA to confirm that bacteria had been removed and stored at −70° C. prior to assay for cytokines.

Commercial solid-phase enzyme immunoassays utilizing the multiple-antibody sandwich principal were used to determine cytokines in biological samples. In these experiments, IL-10, TNFα and IFN-γ were determined with Mouse IL-10, IFN-γ and TNF-α Ready-SET-Go kits (ebioscience), respectively. Concentrations of cytokines were measured by reading optical density at 450 nm and then calculated in reference to values obtained in standard curves generated for each assay. Assays of pooled sera were repeated three times.

Protective Efficacy

Two groups of Swiss Webster mice (10 mice/group) were immunized by s.c. injection with $2.5\times10^4$ CFU of χ10004 (pCD1Ap) cells in 100 μl of isotopic PBS on day 0. Two groups of mice (4 mice/group) were injected with 100 μl of PBS as controls. On day 35, animals were challenged by s.c. injection with 100 μl of virulent *Y. pestis* KIM5+ or lightly anesthetized with a 1:5 xylazine/ketamine mixture and challenged by the intranasal route with 20 μl of bacterial suspension. The challenge dose for s.c. injection was $1\times10^5$ CFU and for i.n. challenge was $2.0\times10^4$ CFU. Protective efficacy was determined by the number of surviving animals. All infected animals were observed over a 15-day period for the development of signs of plague infection.

Statistical Analysis

Data are expressed as means±SE. One-way analysis of variance with Student t-test was used for statistical analysis. A P-value of <0.05 was considered significant.

References for Examples 1-7

1. Straley S C, Bowmer W S (1986) Virulence genes regulated at the transcriptional level by $Ca^{2+}$ in *Yersinia pestis* include structural genes for outer membrane proteins. Infect Immun 51: 445-454.
2. Gong S, Bearden S W, Geoffroy V A, Fetherston J D, Perry R D (2001) Characterization of the *Yersinia pestis* Yfu ABC inorganic iron transport system. Infect Immun 69: 2829-2837.
3. Bertani G (1951) Studies on lysogenesis. I. The mode of phage liberation by lysogenic *Escherichia coli*. J Bacteriol 62: 293-300.
4. Kong W, Wanda S Y, Zhang X, Bollen W, Tinge S A, et al. (2008) Regulated programmed lysis of recombinant *Salmonella* in host tissues to release protective antigens and confer biological containment. Proc Natl Acad Sci USA 105:9361-9366.
5. Sun W, Wang S, Curtiss R, 3rd (2008) Highly efficient method for introducing successive multiple scarless gene deletions and markerless gene insertions into the *Yersinia pestis* chromosome. Appl Environ Microbiol 74: 4241-4245.

6. Uzzau S, Figueroa-Bossi N, Rubino S, Bossi L (2001) Epitope tagging of chromosomal genes in *Salmonella*. Proc Natl Acad Sci USA 98: 15264-15269.
7. Datsenko K A, Wanner B L (2000) One-step inactivation of chromosomal genes in *Escherichia coli* K-12 using PCR products. Proc Natl Acad Sci USA 97: 6640-6645.
8. Sarubbi E, Rudd K E, Xiao H, Ikehara K, Kalman M, et al. (1989) Characterization of the spoT gene of *Escherichia coli*. J Biol Chem 264:15074-15082.
9. Charnetzky W T, Brubaker R R (1982) RNA synthesis in *Yersinia pestis* during growth restriction in calcium-deficient medium. J Bacteriol 149: 1089-1095.
10. Zahorchak R J, Brubaker R R (1982) Effect of exogenous nucleotides on $Ca^{2+}$ dependence and V antigen synthesis in *Yersinia pestis*. Infect Immun 38: 953-959.
11. Chromy B A, Choi M W, Murphy G A, Gonzales A D, Corzett C H, et al. (2005) Proteomic characterization of *Yersinia pestis* virulence. J Bacteriol 187:8172-8180.
12. Loessner H, Endmann A, Leschner S, Westphal K, Rohde M, et al. (2007) Remote control of tumour-targeted *Salmonella enterica* serovar *Typhimurium* by the use of L-arabinose as inducer of bacterial gene expression in vivo. Cell Microbiol 9: 1529-1537.
13. Reed L J, Muench H (1938) A simple method of estimating fifty percent endpoints. Am J Hyg 27: 493-497.
14. Sheehan K C, Ruddle N H, Schreiber R D (1989) Generation and characterization of hamster monoclonal antibodies that neutralize murine tumor necrosis factors. J Immunol 142: 3884-3893.
15. Deng W, Burland V, Plunkett G 3rd, Boutin A, Mayhew G F, et al. (2002) Genome sequence of *Yersinia pestis* KIM. J Bacteriol 184: 4601-4611.
16. Blattner F R, Plunkett G 3rd, Bloch C A, Perna N T, Burland V, et al. (1997) The complete genome sequence of *Escherichia coli* K-12. Science 277: 1453-1474.
17. McClelland M, Sanderson K E, Spieth J, Clifton S W, Latreille P, et al. (2001) Complete genome sequence of *Salmonella enterica* serovar *Typhimurium* LT2. Nature 413: 852-856.
18. Aravind L, Koonin E V (1998) The HD domain defines a new superfamily of metal-dependent phosphohydrolases. Trends Biochem Sci 23: 469-472.
19. Wolf Y I, Aravind L, Grishin N V, Koonin E V (1999) Evolution of aminoacyl tRNA synthetases-analysis of unique domain architectures and phylogenetic trees reveals a complex history of horizontal gene transfer events. Genome Res 9: 689-710.
20. Chipman D M, Shaanan B (2001) The ACT domain family. Curr Opin Struct Biol 11: 694-700.
21. Battesti A, Bouveret E (2006) Acyl carrier protein/SpoT interaction, the switch linking SpoT-dependent stress response to fatty acid metabolism. Mol Microbiol 62: 1048-1063.
22. Gentry D R, Cashel M (1996) Mutational analysis of the *Escherichia coli* spoT gene identifies distinct but overlapping regions involved in ppGpp synthesis and degradation. Mol Microbiol 19: 1373-1384.
23. Xiao H, Kalman M, Ikehara K, Zemel S, Glaser G, et al. (1991) Residual guanosine 39,59-bispyrophosphate synthetic activity of relA null mutants can be eliminated by spoT null mutations. J Biol Chem 266: 5980-5990.
24. Viboud G I, Bliska J B (2005) *Yersinia* outer proteins: role in modulation of host cell signaling responses and pathogenesis. Annu Rev Microbiol 59: 69-89.
25. Brumell J H, Grinstein S (2004) *Salmonella* redirects phagosomal maturation. Curr Opin Microbiol 7: 78-84.
26. Thompson A, Rolfe M D, Lucchini S, Schwerk P, Hinton J C, et al. (2006) The bacterial signal molecule, ppGpp, mediates the environmental regulation of both the invasion and intracellular virulence gene programs of *Salmonella*. J Biol Chem 281: 30112-30121.
27. Sodeinde O A, Sample A K, Brubaker R R, Goguen J D (1988) Plasminogen activator/coagulase gene of *Yersinia pestis* is responsible for degradation of plasmid-encoded outer membrane proteins. Infect Immun 56: 2749-2752.
28. Une T, Brubaker R R (1984) In vivo comparison of avirulent $Vwa^-$ and $Pgm^-$ or Pstr phenotypes of *Yersiniae*. Infect Immun 43: 895-900.
29. Mehigh R J, Sample A K, Brubaker R R (1989) Expression of the low calcium response in *Yersinia pestis*. Microb Pathog 6: 203-217.
30. Gor D O, Rose N R, Greenspan N S (2003) TH1-TH2: a procrustean paradigm. Nat Immunol 4: 503-505.
31. Brubaker R R (2003) Interleukin-10 and inhibition of innate immunity to *Yersiniae:* roles of Yops and LcrV (V antigen). Infect Immun 71: 3673-3681.
32. Motin V L, Nakajima R, Smirnov G B, Brubaker R R (1994) Passive immunity to *Yersiniae* mediated by anti-recombinant V antigen and protein A-V antigen fusion peptide. Infect Immun 62: 4192-4201.
33. Nedialkov Y A, Motin V L, Brubaker R R (1997) Resistance to lipopolysaccharide mediated by the *Yersinia pestis* V antigen-polyhistidine fusion peptide: amplification of interleukin-10. Infect Immun 65: 1196-1203.

Introduction for Examples 8-13

In the Examples below, regulated delayed attenuation technology was applied to the crp gene in *Y. pestis* by constructing a strain in which crp expression is dependent on the presence of arabinose, a sugar that is not present in host tissues [43, 45]. Arabinose is provided during in vitro growth so the strain expresses crp, making it fully functional to interact with host tissues. Once it has invaded host cells, where free arabinose is not available, crp is no longer expressed and the strain becomes attenuated. We compare the virulence and immunogenicity of the regulated delayed attenuation strain with an isogenic Δcrp deletion strain of *Y. pestis.*

Example 8

Crp Synthesis and Growth of *Y. Pestis* Mutants

We constructed mutant *Y. pestis* strains χ10010 (Δcrp) and χ10017 (araC $P_{BAD}$ crp) (FIG. 13). In the araC $P_{BAD}$ crp mutant χ10017, crp expression is dependent on the presence of arabinose. Crp was not detected in either the Δcrp strain χ10010 or the araC $P_{BAD}$ crp strain χ10017 grown in the absence of arabinose (FIG. 14A). Upon arabinose addition, χ10017 synthesized roughly the same amount of Crp as wild-type *Y. pestis.*

Once we had confirmed that Crp synthesis was arabinose-regulated, we moved plasmid pCD1Ap into both mutants and examined their growth in liquid media. Strain χ10010 (pCD1Ap) and χ10017(pCD1Ap) without arabinose grew more slowly and did not reach the same final $OD_{620}$ as *Y. pestis* KIM5+ at 26° C. or 37° C. in HIB medium (FIG. 14B). When 0.05% arabinose was included in the growth medium, χ10017(pCD1Ap) grew at the same rate as wild type.

Example 9

LcrV Synthesis and Secretion in *Y. Pestis* KIM5+ and Mutant Derivatives

Crp is required for expression of the Ysc type 3 secretion system and other virulence factors in *Yersinia* and functional loss of crp diminishes Yop secretion by *Y. enterocolitica* and *Y. pestis* (8, 24, 39). However, the effect of a crp mutation on LcrV secretion has not been reported. Therefore we compared LcrV production in cells and supernatants from *Y. pestis* KIM5+, χ10010(pCD1Ap) and χ10017(pCD1Ap). We observed no difference in LcrV synthesis in whole cell lysates among strains (FIG. 15). There was a reduction in the amount of LcrV detected in supernatants between the wild type and strains χ10010(pCD1Ap) (Δcrp) and χ10017(pCD1Ap) (araC $P_{BAD}$ crp). Wild-type levels of secreted LcrV were restored when strain χ10017(pCD1Ap) was grown with 0.05% arabinose (FIG. 15).

Example 10

Virulence of *Y. Pestis* Mutants in Mice

To investigate the contribution of Crp to *Y. pestis* virulence, we infected Swiss Webster mice s.c. with *Y. pestis* KIM5+, χ10010(pCD1Ap) (Δcrp) or χ10017(pCD1Ap) (araC $P_{BAD}$ crp). Strain χ10017(pCD1Ap) was grown in the presence of arabinose prior to inoculation. The $LD_{50}$ of *Y. pestis* KIM5+ was <10 CFU, consistent with previous results [57]. The LD50 of the Δcrp mutant χ10010(pCD1Ap) was >3×10$^7$CFU. The $LD_{50}$ of strain χ10017(pCD1Ap) was 4.3×10$^5$CFU and the mean time to death was delayed 2-9 days compared to the wild type. The $LD_{50}$ of χ10017(pCD1Ap) was the same as KIM5+ ($LD_{50}$<10) when inoculated mice were injected with arabinose, indicating full complementation of the attenuation phenotype. In a preliminary experiment, we found that both the Δcrp and araC $P_{BAD}$ crp mutants were attenuated when administered by the intranasal route, with $LD_{50}$s>1×10$^4$ CFU. However, mice inoculated with 7-9×10$^3$CFU of either mutant were not protected from subsequent intranasal challenge with 5×10$^3$CFU of KIM5+ (data not shown) and therefore, we did not repeat those experiments.

We evaluated the ability of the *Y. pestis* mutants to disseminate systemically compared to *Y. pestis* KIM5+ by monitoring, over a 9-day period, the lungs, spleen, liver and blood of groups of mice injected with each of the strains. Because of the difference in $LD_{50}$ among the three strains, we inoculated mice with different doses of each. For this type of experiment, we typically choose a dose that is higher than the $LD_{50}$. However, since we were not able to establish an $LD_{50}$ value for the Δcrp strain (>1×10$^7$CFU), we chose a dose that matched the highest dose for which we had data. For the araC $P_{BAD}$ crp mutant, we chose a dose that was 10-fold above the $LD_{50}$. Thus, mice were inoculated with 1.5×10$^3$CFU of *Y. pestis* KIM5+, 4.2×10$^7$CFU of χ10010(pCD1Ap) or 3.8×10$^6$CFU of χ10017(pCD1Ap). The kinetics of infection was similar for both mutants. At 3 days post-infection (p.i.), the number of bacteria recovered from the blood, liver, and spleen were similar for all strains (FIG. 16). About half the number of χ10010 and χ10017 cells was recovered from lungs compared to the wild-type strain. The numbers of mutants recovered from all tissues decreased steadily on days 6 and 9. All mice inoculated with *Y. pestis* KIM5+ succumbed to the infection before day 9, and therefore we do not include any of those mice in our figure for that time point.

Example 11

Evaluation of Protective Immunity

Groups of mice were immunized with a single dose of χ10010(pCD1Ap) (Δcrp), 10017(pCD1Ap) (araC $P_{BAD}$ crp) or *Y. pestis* KIM5 (Pgm$^-$) and challenged 35 days later. For these experiments, we wanted to use the highest possible immunizing dose for each strain. We based our decision on immunizing doses for each strain on the $LD_{50}$ data, shown above. Therefore, we immunized with a dose of 3×10$^4$CFU of 10017(pCD1Ap), 3.8×10$^7$CFU of 10010(pCD1Ap) or 2.5×10$^7$CFU of *Y. pestis* KIM5 (Pgm$^-$), respectively. Our results after challenge show that a single s.c. dose of χ10010 (pCD1Ap) or *Y. pestis* KIM5 (Pgm$^-$) provided excellent protection against a 1×10$^7$$LD_{50}$ s.c. challenge (FIG. 17A). A single s.c. dose of χ10017(pCD1Ap) provided complete protection against a 10,000 $LD_{50}$ s.c. challenge without any symptoms (FIG. 17B). Immunization with strain χ10010 (pCD1Ap) delayed the time of death, but ultimately did not provide protection against a 100 $LD_{50}$ i.n. challenge. Immunization with the *Y. pestis* strain χ10017(pCD1Ap) or the pgm mutant strain KIM5 provided significant protection ($P<0.001$), protecting most of the mice against a 100 $LD_{50}$ i.n. challenge (FIG. 17C). None of the mice immunized with PBS survived challenge by either route (FIG. 17).

Example 12

Serum Immune Responses

Serum IgG responses to YpL and LcrV from immunized mice were measured by ELISA. High anti-YpL (FIG. 18A) titers were slower to develop for the arabinose-regulated crp mutant, χ10017(pCD1Ap) than for the Δcrp mutant, χ10010 (pCD1Ap), but by week 4, the titers were similar. Also by week 4, the anti-LcrV (FIG. 18B) serum IgG titers were somewhat higher in mice immunized with χ10017(pCD1Ap) than with χ10010(pCD1Ap). Titers against both antigens were boosted in mice challenged s.c. No boosting was observed in the mice immunized with χ10017(pCD1Ap) after i.n. challenge.

Th1 cells direct cell-mediated immunity and promote class switching to IgG2a, and Th2 cells provide potent help for B-cell antibody production and promote class switching to IgG1 [41]. The Δcrp strain χ10010(pCD1Ap) elicited a strong Th2 biased response against both antigens, with high IgG1 titers and low IgG2 titers (FIG. 19A, 19B). Strain χ10017(pCD1Ap) induced a more balanced Th1/Th2 response (FIG. 19C, 19D). Challenge did not have much effect on the IgG1/IgG2a ratios, except for the anti-LcrV response in mice immunized with χ10010(pCD1Ap), where the response became more balanced.

Example 13

Induction of Cytokines

Cytokines are critical to the development and functioning of both the innate and adaptive immune response. They are secreted by immune cells that have encountered pathogens, thereby activating and recruiting additional immune cells to respond to the infection. LcrV is an immunomodulator, inhibiting production of TNF-α and IFN-γ and inducing IL-10 in eukaryotic cells both in vivo and in vitro [35,47,49]. To evaluate the effect of reduced LcrV secretion in the two mutants (FIG. 15), we compared production of IL-10, INF-γ and TNF-α in infected mice. Groups of three Swiss-Webster mice were inoculated s.c. with 1,500 CFU of *Y. pestis* KIM5+, $4.2 \times 10^7$ CFU of χ10010(pCD1Ap), or $3.8 \times 10^6$ CFU of χ10017(pCD1Ap). A group of uninfected mice served as controls. Blood was collected via cardiac puncture at days 3 and 6 p.i. for cytokine analysis. We could detect IL-10, but not INF-γ or TNF-α in the sera of animals infected with *Y. pestis* KIM5+, but IL-10 and pro-inflammatory factors such as INF-γ and TNF-α were not detected in mice infected with χ10010(pCD1Ap) and χ10017(pCD1Ap) (data not shown).

Materials and Methods for Examples 8-13

Media and Reagents.

Tryptose blood agar (TBA) and heart infusion broth (HIB) were from Difco. *Y. pestis* strains were grown in HIB and on HIB Congo red agar plates at 30° C. to confirm the pigmentation (Pgm) phenotype of *Y. pestis* strains [54]. Ampicillin, chloramphenicol and L-arabinose were from Sigma (St. Louis, Mo.). Oligonucleotides were from IDT (Coralville, Iowa). Restriction endonucleases were from New England Biolabs. Taq DNA polymerase (New England Biolabs) was used in all PCR tests. Qiagen products (Hilden, Germany) were used to isolate plasmid DNA, gel-purify fragments or purify PCR products. T4 ligase, T4 DNA polymerase and shrimp alkaline phosphatase (SAP) were from Promega.

Bacterial Strains and Plasmids.

Strains and plasmids used are listed in Table 5. *E. coli* TOP10 was used for plasmid propagation. During screening for mutants, *Y. pestis* was grown on TBA agar plates with added chloramphenicol (10 g/ml) or 5% sucrose. *Y. pestis* was grown at 30° C. for 24 h with shaking (liquid media) or for 48 h (solid media) (47).

Plasmid Construction.

All primers used are listed in Table 6. Primer sets CRP-1/CRP-2 and CRP-3/CRP-4 were used for amplifying the y3957' (upstream of crp) and 'y3955 (downstream of crp) fragments, respectively. Complementarity between primers CRP-2 and CRP-3 are indicated by bold lettering. The 'y3955 and y3957' fragments were fused by overlapping PCR using primers CRP-1 and CRP-4. The resulting PCR product was digested with EcoRI and HindII and ligated pUC18 digested with the same enzymes to construct the plasmid pYA4597. Primer sets CRP-5/CRP-6 and CRP-7/CRP-8 were used for amplifying crp containing its original SD sequence (SD-crp), and y3957' (−110 to −660 bp upstream of crp) fragment, respectively. The SD-crp and y3957' fragments were cloned into the XhoI/EcoRI sites and PstI/HindIII sites of pYA3700, respectively to form pYA4581. Plasmid pYA4581 was PstI-digested, blunted by T4 DNA polymerase and dephosphorylated with SAP. The cat-sacB fragment was cut from pYA4373 using PstI and SacI restriction endonucleases and blunted by T4 DNA polymerase. The two fragments were ligated to form plasmid pYA4588. lcrV encoding a C-terminal 6×His was amplified from pCD1Ap using primers lcrV-1 and lcrV-2 and cloned into the EcoRI and HindIII sites of pYA3493 to form pYA4443.

TABLE 5

Bacterial strains and plasmids used in this study.

| Strain or plasmid Strains | Relevant genotype or annotation | Source, reference, or derivation |
|---|---|---|
| *E. coli* TOP10 | F⁻ mcrA Δ(mrr-hsdRMS-mcrBC) φ80lacZΔM15 ΔlacX74 recA1 araD139 Δ(ara-leu)7697 galU galK rpsL endA1 nupG | Invitrogen |
| χ6212 | asd⁻ DH5α derivative | (48) |
| *Y. pestis* KIM6+ | Pgm⁺ pMT1 pPCP1, cured of pCD1 | (40) |
| *Y. pestis* KIM5+ | Pgm⁺ pMT1 pPCP1 pCD1Ap | (40) |
| *Y. pestis* KIM5 | Pgm⁻ pMT1 pPCP1 pCD1Ap | (36) |
| χ10010 | Δcrp-18 *Y. pestis* KIM6+ | This study |
| χ10017 | ΔP$_{crp21}$::TT araC P$_{BAD}$ crp *Y. pestis* KIM6+ | This study |

| Plasmids | | Source |
|---|---|---|
| pUC18 | Ap$^r$ | Invitrogen |
| pKD46 | repA101(ts) ori λ Red recombinase expression plasmid | (39) |
| pYA3493 | Asd⁺ pBR ori β-lactamase signal sequence-based periplasmic secretion plasmid | (42) |
| pYA3700 TT | araC P$_{BAD}$ cassette plasmid, Ap$^r$ | (38) |
| pYA4373 | The cat-sacB cassette in the PstI and SacI sites of pUC18 | (56) |
| pYA4443 | The 6xHis tag in the C-terminal of lcrV gene was cloned into EcoRI and HindIII sites of pYA3493 | pYA3493 |
| pYA4579 | The y3957'-'y3955 fragment ligated by overlapping PCR cloned into EcoRI and HindIII sites of pUC18 | pUC18 |
| pYA4581 | The SD-crp and y3957' fragments cloned into the XhoI/EcoRI sites and PstI/HindIII sites of pYA3700 | pYA3700 |
| pYA4588 | The cat-sacB cassette from pYA4373 cloned into the PstI site of pYA4581 | pYA4581 |

TABLE 6

| Primers used in this study | | |
|---|---|---|
| NAME | SEQUENCE | SEQ. ID NO. |
| CRP-1[a] | 5' cggaagcttgagactgaaaatagcggcga 3' (HindIII) | 46 |
| CRP-2 | 5' gcgactgcaggctgccgagctcttccctctaaaaaccggcgtta 3' | 47 |
| CRP-3 | 5' gaagagctcggcagcctgcagtcgctgttatcctctgttgttatcg 3' | 48 |
| CRP-4[a] | 5' cgggaattcctttttgtaaaatagacacg 3' (EcoRI) | 49 |
| CRP-5[a] | 5' cgggaattcttaacgggtgccgtaaacga 3' (EcoRI) | 50 |
| CRP-6[a] | 5' cggctcgaggaggataacagcgaatggtt 3' (XhoI) | 51 |
| CRP-7[a] | 5' cggctgcaggccgaaaggtatagccaaggt 3' (PstI) | 52 |
| CRP-8[a] | 5' cggaagcttctgatagatcaactgcgcgc 3' (HindIII) | 53 |
| CRP-9 | 5' cgacttcgcgtacctcaaagct 3' | 54 |
| CRP-10 | 5' tacataaccggaaccacaaccag 3' | 55 |
| Cm-V | 5'gttgtccatattggccacgttta3' | 56 |
| SacB-V | 5' gcagaagagatatttttaattgtggacg 3' | 57 |
| araC-V | 5'catccaccgatggataatcgggta3' | 58 |
| IcrV-1 | cgggaattc atgattagagcctacgaaca (EcoRI) | 59 |
| IcrV-2 | cggaagctttcaatgatgatgatgatgatggtgtttaccagacgtgtcatctag (HindIII) | 60 |

* a: the restriction endonuclease sites are underlined
b: the bold letters show the reverse complementary region between CRP-3 and CRP-4

Preparation of LcrV Antiserum.

Full length his-tagged LcrV was expressed from *E. coli* χ6212 (pYA4443) and isolated by nickel chromatography. 150μg of His-tagged LcrV protein was emulsified with Freund's complete adjuvant, and injected into New Zealand female rabbits from Charles River Laboratories. The rabbits were immunized with two booster injections (in Freund's incomplete adjuvant) at 3 week intervals. Antiserum was collected 1 week after the last booster injection.

Strain Construction.

*Y. pestis* mutant strains χ10010 and χ10017 were constructed using the two-step recombination method [56]. The procedure was as follows: *Y. pestis* KIM6+ (pKD46) was electroporated with the linear y3957'-cat-sacB-TT araC $P_{BAD}$ SD-crp fragment excised from plasmid pYA4588 using EcoRI and Hind III. Electroporants were selected on TBA-Cm plates and verified by PCR. Colonies with the correct PCR profile were streaked onto TBA-Cm-sucrose plates to verify sucrose sensitivity and onto HIB Congo Red-Cm plates to confirm the presence of the pgm locus. This intermediate strain was used for all further constructions. To construct strain χ10017, the chromosomal cat-sac cassette was removed by electroporating with 1 g of linear DNA (y3957'-TT araC) cut from pYA4581 using HindIII and BamHI. The loss of the cat-sac cassette in sucrose-resistant colonies was confirmed by PCR. Strain χ10010 was constructed by electroporating the intermediate strain with a linear 'y3955-y3957' fragment cut from pYA4597 using HindIII and EcoRI to delete the entire crp gene. Plasmid pKD46 was cured from a single colony isolate of the above strains to yield χ10010 (Δcrp) and χ10017 (araC $P_{BAD}$ crp). Under BLS-3 containment, plasmid pCD1Ap was then introduced by electroporation into each, yielding χ10010(pCD1Ap) and χ10017 (pCD1Ap).

SDS-PAGE and Immunoblot Analyses.

Secreted proteins were prepared by using a modification of previously described methods [50]. *Y. pestis* was grown in HIB medium overnight at 26° C. Cells were harvested, washed three times in chemically defined medium PMH2 [40], used to inoculate 40 ml of fresh PMH2 medium to an $OD_{600}$ of 0.05 and shaken at 26° C. overnight. Cultures were shifted to 37° C. for 6 h with mild aeration. The $OD_{600}$ of cultures were measured, and bacterial cell pellets were collected by centrifugation. The pellets were suspended in SDS loading buffer. The volume of sample buffer was adjusted based on the $OD_{600}$ to normalize the amount loaded. Cells were lysed by heating at 95° C. for 5 min. Culture supernatants were concentrated by precipitation with 10% (w/v) trichloroacetic acid overnight at 4° C. and collected by centrifugation. Pellets were washed with ice-cold acetone and dissolved in 0.05 M Tris-HCl buffer (pH 9.5). Insoluble materials were removed by centrifugation at 12,500×g for 15 min and the soluble protein concentration was determined using a DC protein assay kit (Bio-Rad, Hercules, Calif.). Samples were heated at 95° C. for 5 min and separated by SDS-PAGE and blotted onto nitrocellulose membranes. The membranes were probed with rabbit anti-LcrV antibodies as described [34].

Virulence Analysis in Mice.

All animal procedures were conducted in ABSL-3 containment facilities and approved by the Arizona State University Animal Care and Use Committee. Single colonies of *Y. pestis* KIM5+ strains to be tested in mice were used to inoculate HIB broth containing 25 μg/ml ampicillin and grown at 26° C. overnight. Bacteria were diluted into 10 ml of fresh medium with 0.2% xylose and 2.5 mM $CaC1_2$ to an $OD_{620}$ of 0.1 and incubated at 26° C. for subcutaneous (s.c.) infections (bubonic plague) or incubated at 37° C. for intranasal (i.n.)

infections (pneumonic plague) and grown to an $OD_{620}$ of 0.6. The cells were harvested by centrifugation and suspended in 1 ml of isotonic PBS.

Female 7-week-old Swiss Webster mice from Charles River Laboratories were inoculated s.c. with 100 µl of the bacterial suspension. Actual numbers of colony-forming units (CFU) inoculated were determined by plating serial dilutions onto TBA agar. To determine the 50% lethal dose ($LD_{50}$), five groups of six mice/group were inoculated i.n. or s.c. with serial dilutions of bacteria. Mice were monitored twice daily for 21 days, and the $LD_{50}$ was calculated as described [52]. For in vivo complementation of strain χ10017 (pCD1Ap), 120 mg of L-arabinose dissolved in 100 µl PBS was intraperitoneally administered to mice on the day of inoculation and once a day thereafter [46].

For colonization/dissemination analysis, groups of mice were injected s.c. At the indicated times after infection, 3 mice per strain were euthanized, and samples of blood, lungs, spleen and liver were removed. The bacterial load for each organ was determined by plating dilutions of the homogenized tissues onto TBA plates containing 25 µg/ml ampicillin and reported as CFU per gram of tissue or CFU per ml blood. Infections were performed in at least two independent experiments.

Determination of Protective Efficacy.

*Y. pestis* strains were grown as described above. Two groups of Swiss Webster mice (10/group) were vaccinated s.c. with $3.8 \times 10^7$ CFU of χ10010(pCD1Ap) or $3 \times 10^4$ CFU of χ10017(pCD1Ap) cells in 100 µl of PBS on day 0. Another two groups of mice (4/group) were injected with 100 μl of PBS as controls. Blood was collected by retro-orbital sinus puncture at 2 and 4 weeks post immunization and 2 weeks after challenge for antibody measurement. Mice were lightly anesthetized using a ketamine and xylazine mixture administered intramuscularly before bleeding. On day 35, animals were challenged s.c. with *Y. pestis* KIM5+ at either $1.3\times10^5$CFU for χ10017(pCD1Ap) group or $1.3\times10^7$CFU for χ10010(pCD1Ap) group in 100 μl PBS or lightly anesthetized with a 1:5 xylazine/ketamine mixture and challenged i.n. with $1.4\times10^4$CFU in 20 μl PBS. Control groups were challenged with $1.3\times10^3$CFU by both routes. All infected animals were observed over a 15-day period for the development of signs of plague infection.

Enzyme-Linked Immunosorbent Assay (ELISA).

ELISA was used to assay serum IgG antibodies against *Yersinia* whole cell lysates (YpL) [55] and purified LcrV antigen of *Y. pestis* KIM5+. Polystyrene 96-well flat-bottom microtiter plates (Dynatech Laboratories Inc., Chantilly, Va.) were coated with 200 ng/well of YpL or purified LcrV protein. The procedures were same as those described previously [42].

Measurement of Cytokine Concentrations.

Cytokines were quantitated by a double-sandwich enzyme-linked immunosorbent assay (ELISA) as described previously [53]. Mice in groups of three were euthanized at intervals by terminal bleeding under anesthesia. Pooled blood was allowed to clot overnight at 4° C., and serum was separated by centrifugation at 10,000×g for 10 min. Sera were filtered once through a 0.22 μm syringe filter, cultured on TBA to confirm that bacteria had been removed and stored at −70° C. prior to assay.

Commercial solid-phase enzyme immunoassays utilizing the multiple-antibody sandwich principal were used to determine cytokines in biological samples. Levels of IL-10, TNF-α and IFN-γ were determined with mouse IL-10, IFN-γ and TNF-α Ready-SET-Go kits (ebioscience), respectively. Concentrations of cytokines were measured by reading optical density at 450 nm and then calculated in reference to values obtained in standard curves generated for each assay. Assays of pooled sera were repeated three times.

Statistical Analysis.

The log rank test was used for analysis of the survival curves. Data are expressed as means±SE. Student t-test was used for other statistical analyses. A P-value of <0.05 was considered significant.

References for Examples 8-13

34. Branger, C. G., J. D. Fetherston, R. D. Perry, and Curtiss, R. III. 2007. Oral vaccination with different antigens from *Yersinia pestis* KIM delivered by live attenuated *Salmonella typhimurium* elicits a protective immune response against plague. Adv Exp Med Biol 603:387-399.
35. Brubaker, R. R. 2003. Interleukin-10 and inhibition of innate immunity to *Yersiniae:* roles of Yops and LcrV (V antigen). Infect Immun 71:3673-3681.
36. Brubaker, R. R. 1983. The Vwa+ virulence factor of *Yersiniae:* the molecular basis of the attendant nutritional requirement for $Ca^{2+}$. Rev Infect Dis 5 Suppl 4:S748-758.
37. Cornelis, G. R., A. Boland, A. P. Boyd, C. Geuijen, M. Iriarte, C. Neyt, M. P. Sory, and I. Stainier. 1998. The virulence plasmid of *Yersinia*, an antihost genome. Microbiol Mol Biol Rev 62:1315-1352.
38. Curtiss, R. III, and Kong, W. 2006. Regulated bacterial lysis for gene vaccine vector delivery and antigen release. United States Patent 2006/0140975.
39. Datsenko, K. A., and B. L. Wanner. 2000. One-step inactivation of chromosomal genes in *Escherichia coli* K-12 using PCR products. Proc Natl Acad Sci USA 97:6640-6645.
40. Gong, S., S. W. Bearden, V. A. Geoffroy, J. D. Fetherston, and R. D. Perry. 2001. Characterization of the *Yersinia pestis* Yfu ABC inorganic iron transport system. Infect Immun 69:2829-2837.
41. Gor, D. O., N. R. Rose, and N. S. Greenspan. 2003. TH1-TH2: a procrustean paradigm. Nat Immunol 4:503-505.
42. Kang, H. *Y., J. Srinivasan, and Curtiss, R. III.* 2002. Immune responses to recombinant pneumococcal PspA antigen delivered by live attenuated *Salmonella enterica* serovar *Typhimurium* vaccine. Infect Immun 70:1739-1749.
43. Katzman, R. L., E. Lisowska, and R. W. Jeanloz. 1970. Invertebrate connective tissue. Isolation of D-arabinose from sponge acidic polysaccharide. Biochem J 119:17-19.
44. Kim, T. J., S. Chauhan, V. L. Motin, E. B. Goh, M. M. Igo, and G. M. Young. 2007. Direct transcriptional control of the plasminogen activator gene of *Yersinia pestis* by the cyclic AMP receptor protein. J Bacteriol 189:8890-8900.
45. Kong, W., S. Y. Wanda, X. Zhang, W. Bollen, S. A. Tinge, K. L. Roland, and Curtiss, R. III. 2008. Regulated programmed lysis of recombinant *Salmonella* in host tissues to release protective antigens and confer biological containment. Proc Natl Acad Sci USA 105:9361-9366.
46. Loessner, H., A. Endmann, S. Leschner, K. Westphal, M. Rohde, T. Miloud, G. Hammerling, K. Neuhaus, and S. Weiss. 2007. Remote control of tumour-targeted *Salmonella enterica* serovar *Typhimurium* by the use of L-arabinose as inducer of bacterial gene expression in vivo. Cell Microbiol 9:1529-1537.
47. Motin, V. L., R. Nakajima, G. B. Smirnov, and R. R. Brubaker. 1994. Passive immunity to *Yersiniae* mediated by anti-recombinant V antigen and protein A-V antigen fusion peptide. Infect Immun 62:4192-4201.

48. Nakayama, K., S. M. Kelly, and Curtiss, R., III. 1988. Construction of an asd+ expression-cloning vector: stable maintenance and high level expression of cloned genes in a *Salmonella* vaccine strain. Bio/Technology 6:693-697.
49. Nedialkov, Y. A., V. L. Motin, and R. R. Brubaker. 1997. Resistance to lipopolysaccharide mediated by the *Yersinia pestis* V antigen-polyhistidine fusion peptide: amplification of interleukin-10. Infect Immun 65:1196-1203.
50. Perry, R. D., A. G. Bobrov, O. Kirillina, H. A. Jones, L. Pedersen, J. Abney, and J. D. Fetherston. 2004. Temperature regulation of the hemin storage (Hms+) phenotype of *Yersinia pestis* is posttranscriptional. J Bacteriol 186:1638-1647.
51. Petersen, S., and G. M. Young. 2002. Essential role for cyclic AMP and its receptor protein in *Yersinia enterocolitica* virulence. Infect Immun 70:3665-3672.
52. Reed, L. J., and H. Muench. 1938. A simple method of estimating fifty percent endpoints. Am. J. Hyg. 27:493-497.
53. Sheehan, K. C., N. H. Ruddle, and R. D. Schreiber. 1989. Generation and characterization of hamster monoclonal antibodies that neutralize murine tumor necrosis factors. J Immunol 142:3884-3893.
54. Straley, S. C., and W. S. Bowmer. 1986. Virulence genes regulated at the transcriptional level by $Ca^{2+}$ in *Yersinia pestis* include structural genes for outer membrane proteins. Infect Immun 51:445-454.
55. Sun, W., K. L. Roland, C. G. Branger, X. Kuang, and Curtiss, R. III. 2009. The role of relA and spoT in *Yersinia pestis* KIM5+ pathogenicity. PLoS One 4:e6720.
56. Sun, W., S. Wang, and Curtiss, R. III. 2008. Highly efficient method for introducing successive multiple scarless gene deletions and markerless gene insertions into the *Yersinia pestis* chromosome. Appl Environ Microbiol 74:4241-4245.

57. Une, T., and R. R. Brubaker. 1984. In vivo comparison of avirulent Vwa- and Pgm- or Pstr phenotypes of *Yersiniae*. Infect Immun 43:895-900.

---

What is claimed is:

1. A recombinant *Yersinia pestis* bacterium, wherein the bacterium comprises the plasmid pCD1, and comprises a araC $P_{BAD}$ crp mutation such that the bacterium has regulated delayed attenuation.

2. The recombinant *Yersinia* pestis bacterium of claim 1, further comprising a regulated expression mutation.

3. A vaccine comprising a recombinant bacterium of claim 1.

4. The vaccine of claim 3, wherein the vaccine elicits a protective immune response against both pneumonic and bubonic plague.

5. The vaccine of claim 3, wherein the vaccine elicits an immune response against *Yersinia* and at least one additional pathogen.

6. The recombinant *Yersinia pestis* bacterium of claim 1, wherein the bacterium is infectious.

7. A recombinant *Yersinia pestis* bacterium, wherein the bacterium comprises:
   a) pCD1,
   b) a araC $P_{BAD}$ crp mutation such that the bacterium has regulated delayed attenuation
   (c) a mutation in relA such that ppGpp synthesis is decreased, and
   (d) a mutation in spoT such that ppGpp synthesis is decreased.

8. The recombinant bacterium of claim 7, wherein bacterium is infectious.

9. The recombinant bacterium of claim 1, wherein the bacterium comprises:
   a) pCD1,
   b) a araC $P_{BAD}$ crp mutation such that the bacterium has regulated delayed attenuation,
   (c) a mutation in relA such that ppGpp synthesis is decreased, and
   (d) a mutation in spoT such that ppGpp synthesis is decreased.

10. The recombinant bacterium of claim 1, wherein the bacterium comprises:
    a) pCD1,
    b) a araC $P_{BAD}$ crp mutation such that the bacterium has regulated delayed attenuation, and
    c) a second regulated attenuation mutation, such that the bacterium is capable of colonizing a host in a non-attenuated manner, and ppGpp synthesis is decreased.

11. A recombinant bacterium of claim 1, wherein the bacterium comprises:
    a) pCD1
    b) a relA inactivating mutation,
    c) a spoT inactivating mutation,
    d) a ΔlacZ::TT araC $P_{BAD}$ spoT mutation, and
    e) a araC $P_{BAD}$ crp mutation such that the bacterium has regulated delayed attenuation.

12. A method of inducing a protective immune response in a host, the method comprising administering an immunogenic amount of a bacterium of claim 1 to the host.

13. A method of inducing a protective immune response in a host, the method comprising administering an immunogenic amount of a bacterium of claim 7 to the host.

* * * * *

SEQUENCE LISTING

```
<160> NUMBER OF SEQ ID NOS: 60

<210> SEQ ID NO 1
<211> LENGTH: 31
<212> TYPE: DNA
<213> ORGANISM: Artificial Sequence
<220> FEATURE:
<223> OTHER INFORMATION: Yersinia pestis plague

<400> SEQUENCE: 1
cggctgcagc ccatcactcc agcgcagaac t                                   31

<210> SEQ ID NO 2
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 2
cgggcatgct ccagcccatt caggcttat                                      29

<210> SEQ ID NO 3
<211> LENGTH: 31
<212> TYPE: DNA
<213> ORGANISM: Artificial Sequence
<220> FEATURE:
<223> OTHER INFORMATION: Yersinia pestis plague

<400> SEQUENCE: 3
cgggaattcc aaaggagcaa tgcatgtatg g                                   31

<210> SEQ ID NO 4
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 4
cgggagctcc atgtgttgcc aactggctg                                      29

<210> SEQ ID NO 5
<211> LENGTH: 22
<212> TYPE: DNA
```

```
<213> ORGANISM: Artificial Sequence
<220> FEATURE:
<223> OTHER INFORMATION: Yersinia pestis plague

<400> SEQUENCE: 5
ctaaattgtt atctcttcgt ag                                              22

<210> SEQ ID NO 6
<211> LENGTH: 23
<212> TYPE: DNA
<213> ORGANISM: Artificial Sequence
<220> FEATURE:
<223> OTHER INFORMATION: Yersinia pestis plague

<400> SEQUENCE: 6
tgcagggaga tgagttaaca atg                                             23

<210> SEQ ID NO 7
<211> LENGTH: 40
<212> TYPE: DNA
<213> ORGANISM: Artificial Sequence
<220> FEATURE:
<223> OTHER INFORMATION: Yersinia pestis plague

<400> SEQUENCE: 7
cggctcgagg gagtgaaacg ttgtacctgt ttgaaagcct                            40

<210> SEQ ID NO 8
<211> LENGTH: 37
<212> TYPE: DNA
<213> ORGANISM: Artificial Sequence
<220> FEATURE:
<223> OTHER INFORMATION: Yersinia pestis plague

<400> SEQUENCE: 8
cgggagctct taattgcgat tacggctaac tttaacc                               37

<210> SEQ ID NO 9
<211> LENGTH: 34
<212> TYPE: DNA
<213> ORGANISM: Artificial Sequence
<220> FEATURE:
<223> OTHER INFORMATION: Yersinia pestis plague

<400> SEQUENCE: 9
cgggaattca gcaaaacaga caaacgcctg ctgg                                  34

<210> SEQ ID NO 10
<211> LENGTH: 34
<212> TYPE: DNA
<213> ORGANISM: Artificial Sequence
<220> FEATURE:
<223> OTHER INFORMATION: Yersinia pestis plague

<400> SEQUENCE: 10
cggctgcagt agacacccett aatctctctg catg                                 34

<210> SEQ ID NO 11
<211> LENGTH: 37
<212> TYPE: DNA
<213> ORGANISM: Artificial Sequence
<220> FEATURE:
<223> OTHER INFORMATION: Yersinia pestis plague

<400> SEQUENCE: 11
cggctgcagt acagatcata tctctctttt catcctc                               37
```

<210> SEQ ID NO 12
<211> LENGTH: 34
<212> TYPE: DNA
<213> ORGANISM: Artificial Sequence
<220> FEATURE:
<223> OTHER INFORMATION: Yersinia pestis plague

<400> SEQUENCE: 12
cgggcatgcc tggtgcgtat agctgaggat gaat                               34

<210> SEQ ID NO 13
<211> LENGTH: 31
<212> TYPE: DNA
<213> ORGANISM: Artificial Sequence
<220> FEATURE:
<223> OTHER INFORMATION: Yersinia pestis plague

<400> SEQUENCE: 13
gagataacgt gagcaaaaca aaatctggtc g                                  31

<210> SEQ ID NO 14
<211> LENGTH: 28
<212> TYPE: DNA
<213> ORGANISM: Artificial Sequence
<220> FEATURE:
<223> OTHER INFORMATION: Yersinia pestis plague

<400> SEQUENCE: 14
gagcctttta tgcgttcgat ccgattcg                                      28

<210> SEQ ID NO 15
<211> LENGTH: 31
<212> TYPE: DNA
<213> ORGANISM: Artificial Sequence
<220> FEATURE:
<223> OTHER INFORMATION: Yersinia pestis plague

<400> SEQUENCE: 15
cggaactgca gatgggaatt agccatggtc c                                  31

<210> SEQ ID NO 16
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 16
cggctgcagt gtaggctgga gctgcttcg                                     29

<210> SEQ ID NO 17
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 17
cggaagctta tgagcgtagt ggtggctaa                                     29

<210> SEQ ID NO 18
<211> LENGTH: 29
<212> TYPE: DNA
<213> ORGANISM: Artificial Sequence
<220> FEATURE:

<223> OTHER INFORMATION: Yersinia pestis plague

<400> SEQUENCE: 18
cggggatcca ttgcgattac ggctaactt                                         29

<210> SEQ ID NO 19
<211> LENGTH: 36
<212> TYPE: DNA
<213> ORGANISM: Artificial Sequence
<220> FEATURE:
<223> OTHER INFORMATION: Yersinia pestis plague

<400> SEQUENCE: 19
cgggagctct aacgcctatg aatcctcaac gctatg                                 36

<210> SEQ ID NO 20
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 20
cgggaattct gtgtgtccgt ttatacatc                                         29

<210> SEQ ID NO 21
<211> LENGTH: 34
<212> TYPE: DNA
<213> ORGANISM: Artificial Sequence
<220> FEATURE:
<223> OTHER INFORMATION: Yersinia pestis plague

<400> SEQUENCE: 21
cggggatccg actacaaaga ccatgacggt gatt                                   34

<210> SEQ ID NO 22
<211> LENGTH: 36
<212> TYPE: DNA
<213> ORGANISM: Artificial Sequence
<220> FEATURE:
<223> OTHER INFORMATION: Yersinia pestis plague

<400> SEQUENCE: 22
cgggagctcc atatgaatat cctccttagt tcctat                                 36

<210> SEQ ID NO 23
<211> LENGTH: 23
<212> TYPE: DNA
<213> ORGANISM: Artificial Sequence
<220> FEATURE:
<223> OTHER INFORMATION: Yersinia pestis plague

<400> SEQUENCE: 23
gttgtccata ttggccacgt tta                                               23

<210> SEQ ID NO 24
<211> LENGTH: 28
<212> TYPE: DNA
<213> ORGANISM: Artificial Sequence
<220> FEATURE:
<223> OTHER INFORMATION: Yersinia pestis plague

<400> SEQUENCE: 24
gcagaagaga tattttaat tgtggacg                                           28

```
<210> SEQ ID NO 25
<211> LENGTH: 24
<212> TYPE: DNA
<213> ORGANISM: Artificial Sequence
<220> FEATURE:
<223> OTHER INFORMATION: Yersinia pestis plague

<400> SEQUENCE: 25
catccaccga tggataatcg ggta                                                24

<210> SEQ ID NO 26
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 26
aggcgacgat ccctagctgg tctga                                               25

<210> SEQ ID NO 27
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 27
cgtttacagc gtggactacc agggt                                               25

<210> SEQ ID NO 28
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 28
tcctagctta ttttctaccc gagga                                               25

<210> SEQ ID NO 29
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 29
ttaattcggc ggtaagctca gctaa                                               25

<210> SEQ ID NO 30
<211> LENGTH: 26
<212> TYPE: DNA
<213> ORGANISM: Artificial Sequence
<220> FEATURE:
<223> OTHER INFORMATION: Yersinia pestis plague

<400> SEQUENCE: 30
tgtttcagtg ctaacgaagt ttacgc                                              26

<210> SEQ ID NO 31
<211> LENGTH: 25
<212> TYPE: DNA
<213> ORGANISM: Artificial Sequence
<220> FEATURE:
<223> OTHER INFORMATION: Yersinia pestis plague
```

<400> SEQUENCE: 31
acaatcactg aggctatggc gctga                                    25

<210> SEQ ID NO 32
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 32
tcttgttgtt gctgttggaa ctggc                                    25

<210> SEQ ID NO 33
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 33
gttgttcgcg gccagcaata ttact                                    25

<210> SEQ ID NO 34
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 34
catttgctgc ctgcgttaga tcaac                                    25

<210> SEQ ID NO 35
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 35
gccaaaatac atgcagcagt tgaat                                    25

<210> SEQ ID NO 36
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 36
tcgtcaggta tctcgattgg tgcag                                    25

<210> SEQ ID NO 37
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 37
ccattgccga cacttcttaa gtcat                                    25

<210> SEQ ID NO 38
<211> LENGTH: 25

```
<212> TYPE: DNA
<213> ORGANISM: Artificial Sequence
<220> FEATURE:
<223> OTHER INFORMATION: Yersinia pestis plague

<400> SEQUENCE: 38
tcacgtatgg atgtagaagt catgc                                    25

<210> SEQ ID NO 39
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 39
gtttttgtcc ttattgccag catcg                                    25

<210> SEQ ID NO 40
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 40
gtgctttatg taccgctctt gaaca                                    25

<210> SEQ ID NO 41
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 41
gtcaatatcg ctgacatgtt gccat                                    25

<210> SEQ ID NO 42
<211> LENGTH: 28
<212> TYPE: DNA
<213> ORGANISM: Artificial Sequence
<220> FEATURE:
<223> OTHER INFORMATION: Yersinia pestis plague

<400> SEQUENCE: 42
acgtcattct tctaatttaa ctgagatg                                 28

<210> SEQ ID NO 43
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 43
aagtgatttc aggctctgcg gtaat                                    25

<210> SEQ ID NO 44
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 44
```
tcaaggatag cgtttaataa ttgatccag                                    29

<210> SEQ ID NO 45
<211> LENGTH: 25
<212> TYPE: DNA
<213> ORGANISM: Artificial Sequence
<220> FEATURE:
<223> OTHER INFORMATION: Yersinia pestis plague

<400> SEQUENCE: 45
tttatgtgca cattggatca ggagc                                        25

<210> SEQ ID NO 46
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 46
cggaagcttg agactgaaaa tagcggcga                                    29

<210> SEQ ID NO 47
<211> LENGTH: 44
<212> TYPE: DNA
<213> ORGANISM: Artificial Sequence
<220> FEATURE:
<223> OTHER INFORMATION: Yersinia pestis plague

<400> SEQUENCE: 47
gcgactgcag gctgccgagc tcttccctct aaaaaccggc gtta                   44

<210> SEQ ID NO 48
<211> LENGTH: 46
<212> TYPE: DNA
<213> ORGANISM: Artificial Sequence
<220> FEATURE:
<223> OTHER INFORMATION: Yersinia pestis plague

<400> SEQUENCE: 48
gaagagctcg gcagcctgca gtcgctgtta tcctctgttg ttatcg                 46

<210> SEQ ID NO 49
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 49
cgggaattcc ttttgtaaa atagacacg                                     29

<210> SEQ ID NO 50
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 50
cgggaattct taacgggtgc cgtaaacga                                    29

<210> SEQ ID NO 51
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 51
cggctcgagg aggataacag cgaatggtt                                    29

<210> SEQ ID NO 52
<211> LENGTH: 30
<212> TYPE: DNA
<213> ORGANISM: Artificial Sequence
<220> FEATURE:
<223> OTHER INFORMATION: Yersinia pestis plague

<400> SEQUENCE: 52
cggctgcagg ccgaaaggta tagccaaggt                                   30

<210> SEQ ID NO 53
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 53
cggaagcttc tgatagatca actgcgcgc                                    29

<210> SEQ ID NO 54
<211> LENGTH: 22
<212> TYPE: DNA
<213> ORGANISM: Artificial Sequence
<220> FEATURE:
<223> OTHER INFORMATION: Yersinia pestis plague

<400> SEQUENCE: 54
cgacttcgcg tacctcaaag ct                                           22

<210> SEQ ID NO 55
<211> LENGTH: 23
<212> TYPE: DNA
<213> ORGANISM: Artificial Sequence
<220> FEATURE:
<223> OTHER INFORMATION: Yersinia pestis plague

<400> SEQUENCE: 55
tacataaccg gaaccacaac cag                                          23

<210> SEQ ID NO 56
<211> LENGTH: 23
<212> TYPE: DNA
<213> ORGANISM: Artificial Sequence
<220> FEATURE:
<223> OTHER INFORMATION: Yersinia pestis plague

<400> SEQUENCE: 56
gttgtccata ttggccacgt tta                                          23

<210> SEQ ID NO 57
<211> LENGTH: 28
<212> TYPE: DNA
<213> ORGANISM: Artificial Sequence
<220> FEATURE:
<223> OTHER INFORMATION: Yersinia pestis plague

<400> SEQUENCE: 57
gcagaagaga tattttaat tgtggacg                                      28

```
<210> SEQ ID NO 58
<211> LENGTH: 24
<212> TYPE: DNA
<213> ORGANISM: Artificial Sequence
<220> FEATURE:
<223> OTHER INFORMATION: Yersinia pestis plague

<400> SEQUENCE: 58
catccaccga tggataatcg ggta                                        24

<210> SEQ ID NO 59
<211> LENGTH: 29
<212> TYPE: DNA
<213> ORGANISM: Artificial Sequence
<220> FEATURE:
<223> OTHER INFORMATION: Yersinia pestis plague

<400> SEQUENCE: 59
cgggaattca tgattagagc ctacgaaca                                   29

<210> SEQ ID NO 60
<211> LENGTH: 51
<212> TYPE: DNA
<213> ORGANISM: Artificial Sequence
<220> FEATURE:
<223> OTHER INFORMATION: Yersinia pestis plague

<400> SEQUENCE: 60
cggaagcttt caatgatgat gatgatggtg tttaccagac gtgtcatcta g           51
```